(12) United States Patent
Oh et al.

(10) Patent No.: US 11,605,781 B2
(45) Date of Patent: Mar. 14, 2023

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Hong-Se Oh, Gyeonggi-do (KR); Tae-Jin Lee, Gyeonggi-do (KR); Jeong-Eun Yang, Gyeonggi-do (KR); Yeon-Gun Lee, Gyeonggi-do (KR)

(73) Assignee: Rohm and Haas Electronic Materials Korea Ltd.

(*) Notice: Subject to any disclaimer, the term of this patent is extended or adjusted under 35 U.S.C. 154(b) by 0 days.

(21) Appl. No.: 16/757,778

(22) PCT Filed: Nov. 21, 2018

(86) PCT No.: PCT/KR2018/014300
§ 371 (c)(1),
(2) Date: Apr. 21, 2020

(87) PCT Pub. No.: WO2019/107822
PCT Pub. Date: Jun. 6, 2019

(65) Prior Publication Data
US 2021/0193925 A1 Jun. 24, 2021

(30) Foreign Application Priority Data
Nov. 28, 2017 (KR) ........................ 10-2017-0160254

(51) Int. Cl.
*H01L 51/00* (2006.01)
*C07C 211/61* (2006.01)
*C09K 11/06* (2006.01)
*H01L 51/50* (2006.01)

(52) U.S. Cl.
CPC .......... *H01L 51/006* (2013.01); *C07C 211/61* (2013.01); *C09K 11/06* (2013.01); *C07C 2603/18* (2017.05); *C07C 2603/52* (2017.05); *C09K 2211/1007* (2013.01); *C09K 2211/1011* (2013.01); *C09K 2211/1014* (2013.01); *H01L 51/0055* (2013.01); *H01L 51/0058* (2013.01); *H01L 51/5056* (2013.01)

(58) Field of Classification Search
CPC ............... H01L 51/006; H01L 51/0055; H01L 51/0058; H01L 51/5056; C09K 11/06; C09K 2211/1007; C09K 2211/1011; C09K 2211/1014; C07C 211/61; C07C 2603/52; C07C 2603/18
See application file for complete search history.

(56) References Cited

U.S. PATENT DOCUMENTS

| | | | |
|---|---|---|---|
| 2020/0013965 A1* | 1/2020 | Yang | C07D 209/56 |
| 2020/0207712 A1* | 7/2020 | Yang | C07D 409/04 |
| 2021/0013418 A1* | 1/2021 | Kim | H01L 51/0055 |
| 2021/0043848 A1* | 2/2021 | Kim | C09K 11/02 |
| 2021/0151693 A1* | 5/2021 | Lee | C07D 487/16 |
| 2021/0257556 A1* | 8/2021 | Lee | H01L 51/0059 |
| 2022/0109110 A1* | 4/2022 | Park | C07D 401/04 |

FOREIGN PATENT DOCUMENTS

| | | | |
|---|---|---|---|
| KR | 20090114716 A | | 11/2009 |
| KR | 20150121337 A | | 10/2015 |
| KR | 20150121337 A | * | 10/2015 |

OTHER PUBLICATIONS

X. Li et al, Asian Journal of Organic Chemistry, 1876-1884 (2017) (Year: 2017).*
CAS Abstract and Indexed Compounds J. Jang et al., KR 2015121337 (2015) (Year: 2017).*
Li, X. et al., "Palladium-Catalyzed Double Suzuki Reactions: Synthesis of Dibenzo[4,5:6,7]cyclohepta[1,2,3-de] naphthalenes", Asian Journal of Organic Chemistry, 1st published Sep. 26, 2017, vol. 6, pp. 1876-1884.
Zahradnik, R. et al., "Tables of Quantum Chemical Data, II. Energy Characteristics of Some Non-Alternant Hydrocarbons", Collect. Czech. Chem. Commun., 1964, vol. 29, pp. 1932-1944 (p. 1932 is only available).
Gisin, M. et al., "Biradicaloid Intermediates in Photochemistry: Spectroscopic and Kinetic Study of 1,4-Perinaphthadiyl and Related 1,8-Naphthoquinodimethanes", Journal of the American Chemical Society, 1979, vol. 101, No. 8, pp. 2216-2218.

* cited by examiner

*Primary Examiner* — Alexander R Pagano
(74) *Attorney, Agent, or Firm* — G. Creston Campbell

(57) ABSTRACT

The present disclosure relates to an organic electroluminescent compound and an organic electroluminescent device comprising the same. By using the organic electroluminescent compound of the present disclosure, an organic electroluminescent device having high luminous efficiency and/or long lifespan properties can be provided compared to conventional organic electroluminescent devices.

9 Claims, 1 Drawing Sheet

[Fig. 1]
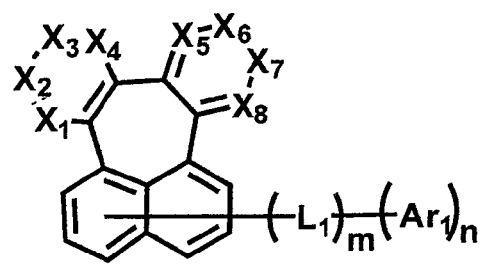
[Fig. 2]
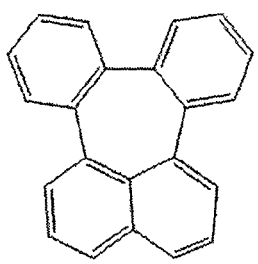
[Fig. 3]
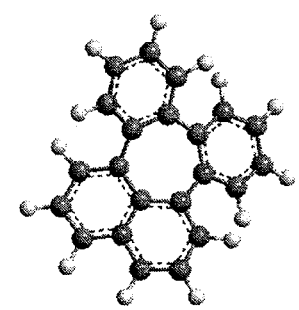
[Fig. 4]
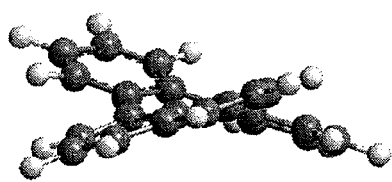

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

A small molecular green organic electroluminescent device (OLED) was first developed by Tang, et al., of Eastman Kodak in 1987 by using TPD/Alq3 bi-layer consisting of a light-emitting layer and a charge transport layer. Thereafter, the development of OLEDs was rapidly effected and OLEDs have been commercialized. An OLED changes electric energy into light by applying electricity to an organic light-emitting material, and commonly comprises an anode, a cathode, and an organic layer between the two electrodes. In order to enhance the efficiency and stability of an OLED, it has a multilayer structure comprising a hole transport zone, a light-emitting layer, an electron transport zone, etc.

In addition, the performance of the OLED is strongly dependent on the compounds comprised in each zone or layer. Hence, a study of new compounds which can enhance the performance of the OLED is vigorously conducted.

For example, in the OLED, copper phthalocyanine (CuPc), 4,4'-bis[N-(1-naphthyl)-N-phenylamino]biphenyl (NPB), N,N'-diphenyl-N,N'-bis(3-methylphenyl)-(1,1'-biphenyl)-4,4'-diamine(TPD), 4,4',4"-tris(3-methylphenylphenylamino)triphenylamine (MTDATA), etc., were used as a compound contained in the hole transport zone. However, an OLED using these materials is problematic in deteriorating quantum efficiency and lifespan. It is because, when an OLED is driven under high current, thermal stress occurs between an anode and a hole injection layer, and the thermal stress significantly reduces the lifespan of the device. Further, since the organic material used in the hole transport zone has very high hole mobility, the hole-electron charge balance may be broken and quantum efficiency (cd/A) may decrease. Hence, a new compound which can substitute conventional compounds used for a hole transport zone is desired.

Also, a study of various materials and devices for improving luminous efficiency, driving voltage, and/or lifespan characteristics of an OLED is continuously conducted.

DISCLOSURE OF INVENTION

Technical Problem

The objective of the present disclosure is to provide an organic electroluminescent compound which can be effectively used to produce an organic electroluminescent device having high luminous efficiency and/or long lifespan properties.

Solution to Problem

The present inventors found that the above objective can be achieved by an organic electroluminescent compound represented by the following formula 1, which is a 7-membered ring compound based on a dibenzo[4,5:6,7]cyclohepta[1,2,3-di]naphthalene moiety compound:

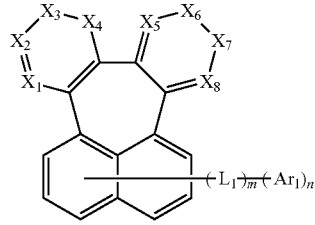

(1)

wherein $X_1$ to $X_8$ each independently represent N or $CR_1$;

$R_1$ represents hydrogen or

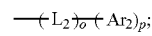

$L_1$ and $L_2$ each independently represent a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

$Ar_1$ and $Ar_2$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or

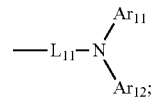

or may be linked to an adjacent substituent to form a substituted or unsubstituted (3- to 30-membered) mono- or polycyclic ring;

$L_{11}$ represents a single bond, a substituted or unsubstituted (C6-C30)arylene, or a substituted or unsubstituted (3- to 30-membered)heteroarylene;

$Ar_{11}$ and $Ar_{12}$ each independently represent a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl; and m, n, o, and p each independently represent an integer of 0 to 2.

Advantageous Effects of Invention

By using the organic electroluminescent compound of the present disclosure, an organic electroluminescent device having high luminous efficiency and/or long lifespan properties can be provided.

BRIEF DESCRIPTION OF DRAWINGS

FIG. 1 is the representative formula of the organic electroluminescent compound of the present disclosure.

FIG. 2 is the basic structure of the organic electroluminescent compound of the present disclosure.

FIG. 3 is the basic structure of the organic electroluminescent compound of the present disclosure in 3D molecular structure.

FIG. 4 is the basic structure of the organic electroluminescent compound of the present disclosure in 3D molecular structure.

MODE FOR THE INVENTION

Hereinafter, the present disclosure will be described in detail. However, the following description is intended to explain the disclosure, and is not meant in any way to restrict the scope of the disclosure.

An organic electroluminescent device of the present disclosure comprises a first electrode; a second electrode facing the first electrode; and a light-emitting layer between the first electrode and the second electrode. A hole transport zone may be comprised between the first electrode and the light-emitting layer, and an electron transport zone may be comprised between the light-emitting layer and the second electrode. One of the first and second electrodes may be an anode, and the other may be a cathode.

The term "organic electroluminescent compound" in the present disclosure means a compound that may be used in an organic electroluminescent device, and may be comprised in any material layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

The term "hole transport zone" in the present disclosure means an area in which holes move between the first electrode and the light-emitting layer, and may comprise, for example, at least one of a hole injection layer, a hole transport layer, a hole auxiliary layer, a light-emitting auxiliary layer, and an electron blocking layer. The hole injection layer, the hole transport layer, the hole auxiliary layer, the light-emitting auxiliary layer, and the electron blocking layer may be, respectively, a single layer, or a multi-layer in which two or more layers are stacked. According to one embodiment of the present disclosure, the hole transport zone may comprise a first hole transport layer and a second hole transport layer. The second hole transport layer may be one or more layers among the plural hole transport layers, and may comprise at least one of a hole auxiliary layer, a light-emitting auxiliary layer, and an electron blocking layer. In addition, according to another embodiment of the present disclosure, the hole transport zone may comprise a first hole transport layer and a second hole transport layer, and the first hole transport layer may be placed between the first electrode and the light-emitting layer, the second hole transport layer may be placed between the first hole transport layer and the light-emitting layer, and the second hole transport layer may be a layer which plays a role of a hole transport layer, a light-emitting auxiliary layer, a hole auxiliary layer, and/or an electron blocking layer.

The hole transport layer may be placed between the anode (or the hole injection layer) and the light-emitting layer, enables holes transferred from the anode to smoothly move to the light-emitting layer, and may block the electrons transferred from the cathode to confine electrons within the light-emitting layer. The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled.

Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a light-emitting auxiliary layer, a hole auxiliary layer, or an electron blocking layer. The light-emitting auxiliary layer, the hole auxiliary layer, and/or the electron blocking layer may have an effect of improving the luminous efficiency and/or the lifespan of the organic electroluminescent device.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is meant to be a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is meant to be a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "(3- to 7-membered)heterocycloalkyl" is meant to be a cycloalkyl having at least one heteroatom selected from the group consisting of B, N, O, S, Si, and P, preferably O, S, and N, and 3 to 7 ring backbone atoms, preferably 5 to 7 ring backbone atoms, and includes tetrahydrofuran, pyrrolidine, thiolan, tetrahydropyran, etc. "(C6-C30)aryl" is meant to be a monocyclic or fused ring radical derived from an aromatic hydrocarbon having 6 to 30 ring backbone carbon atoms, which may be partially saturated and may have a spiro structure, in which the number of ring backbone carbon atoms is preferably 6 to 25, more preferably 6 to 18, and includes phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "(3- to 30-membered) heteroaryl" is meant to be an aryl group having at least one, preferably 1 to 4 heteroatoms selected from the group consisting of B, N, O, S, Si, and P, and 3 to 30 ring backbone atoms, which is a monocyclic ring, or a fused ring condensed with at least one benzene ring; may be partially saturated; may be one formed by linking at least one heteroaryl or aryl group to a heteroaryl group via a single bond(s); may have a spiro structure; and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, etc. "Halogen" includes F, Cl, Br, and I.

Herein, "substituted" in the expression "substituted or unsubstituted" means that a hydrogen atom in a certain functional group is replaced with another atom or functional group, i.e., a substituent. The substituents of the substituted (C1-C30)alkyl(ene), the substituted (C6-C30)aryl(ene), the substituted (3- to 30-membered)heteroaryl(ene), the substituted (C3-C30)cycloalkyl(ene), the substituted (C1-C30) alkoxy, the substituted tri(C1-C30)alkylsilyl, the substituted di(C1-C30)alkyl(C6-C30)arylsilyl, the substituted (C1-C30) alkyldi(C6-C30)arylsilyl, the substituted tri(C6-C30)arylsilyl, and the substituted (3- to 30-membered) mono- or polycyclic ring in $Ar_1$, $Ar_2$, $L_1$, $L_2$, $L_{11}$, $Ar_{11}$, and $Ar_{12}$ in formula 1, etc., each independently are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthio, a (3- to 30-membered)heteroaryl unsubstituted or substituted with a (C6-C30)aryl, a (C6-C30)aryl unsubstituted or substituted with a (3- to 30-membered)heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30) arylamino unsubstituted or substituted with a (C1-C30) alkyl(s), a (C1-C30)alkyl(C6-C30)arylamino, a (C1-C30) alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl (C1-C30)alkyl, and a (C1-C30)alkyl(C6-C30)aryl. According to one embodiment of the present disclosure, the substituents are each independently a (C1-C20)alkyl(s) and/or a (C6-C25)aryl(s). According to another embodiment of the present disclosure, the substituents are each independently a (C1-C10)alkyl(s) and/or a (C6-C18)aryl(s), and for example, each independently, at least one selected from the group consisting of a methyl, a phenyl, and a biphenyl.

In formula 1 above, $X_1$ to $X_8$ each independently represent N or $CR_1$; and $R_1$ represents hydrogen or

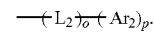

In formula 1 above, $L_1$ and $L_2$ each independently represent a single bond, a substituted or unsubstituted (C1-C30) alkylene, a substituted or unsubstituted (C6-C30)arylene, a substituted or unsubstituted (3- to 30-membered)heteroarylene, or a substituted or unsubstituted (C3-C30)cycloalkylene; according to one embodiment of the present disclosure, $L_1$ and $L_2$ each independently represent a single bond, a substituted or unsubstituted (C6-C25)arylene, or a substituted or unsubstituted (5- to 25-membered)heteroarylene; and according to another embodiment of the present disclosure, $L_1$ and $L_2$ each independently represent a single bond, an unsubstituted (C6-C18)arylene, or an unsubstituted (5- to 18-membered)heteroarylene. For example, $L_1$ and $L_2$ may each independently represent a single bond, a phenylene, a triazinylene, a quinazolinylene, a quinoxalinylene, a benzoquinazolinylene, a benzoquinoxalinylene, or a pyridylene.

In formula 1 above, $Ar_1$ and $Ar_2$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30) alkylsilyl, a substituted or unsubstituted di(C1-C30)alkyl (C6-C30)arylsilyl, a substituted or unsubstituted (C1-C30) alkyldi(C6-C30)arylsilyl, a substituted or unsubstituted tri (C6-C30)arylsilyl, or

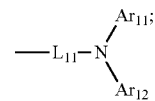

or may be linked to an adjacent substituent to form a substituted or unsubstituted (3- to 30-membered) mono- or polycyclic ring; according to one embodiment of the present disclosure, $Ar_1$ and $Ar_2$ each independently represent hydrogen, a substituted or unsubstituted (C6-C25)aryl, a substituted or unsubstituted (5- to 25-membered)heteroaryl, or

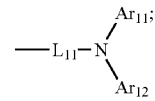

and according to another embodiment of the present disclosure, $Ar_1$ and $Ar_2$ each independently represent hydrogen, an unsubstituted (C6-C18)aryl, a (5- to 20-membered)heteroaryl unsubstituted or substituted with a (C6-C18)aryl(s), or

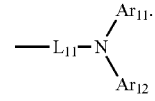

For example, Ar$_1$ and Ar$_2$ may each independently represent hydrogen, a phenyl, a biphenyl, a diphenyltriazinyl, a phenylbiphenyltriazinyl, a quinazolinyl, a quinoxalinyl, a benzoquinazolinyl, a benzoquinoxalinyl, a dimethylfluorenyl, a dibenzofuranyl, a dibenzothiophenyl, etc.

L$_{11}$ represents a single bond, a substituted or unsubstituted (C6-C30)arylene, or a substituted or unsubstituted (3- to 30-membered)heteroarylene; according to one embodiment of the present disclosure, L$_{11}$ represents a single bond, a substituted or unsubstituted (C6-C25)arylene, or a substituted or unsubstituted (3- to 25-membered)heteroarylene; and according to another embodiment of the present disclosure, L$_{11}$ represents a single bond, an unsubstituted (C6-C18)arylene, or an unsubstituted (5- to 18-membered)heteroarylene. For example, L$_{11}$ represents a single bond.

Ar$_{11}$ and Ar$_{12}$ each independently represent a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl; according to one embodiment of the present disclosure, Ar$_{11}$ and Ar$_{12}$ each independently represent a substituted or unsubstituted (C6-C25)aryl, or a substituted or unsubstituted (5- to 25-membered)heteroaryl; and according to another embodiment of the present disclosure, Ar$_{11}$ and Ar$_{12}$ each independently represent a (C6-C18)aryl unsubstituted or substituted with a (C1-C6)alkyl(s), or a (5- to 20-membered)heteroaryl unsubstituted or substituted with a (C6-C18)aryl(s). For example, Ar$_{11}$ and Ar$_{12}$ may each independently represent a phenyl, a biphenyl, a dimethylfluorenyl, a naphthylphenyl, a terphenyl, a dibenzofuranyl, a dibenzothiophenyl, or a phenylcarbazolyl. In addition, Ar$_{11}$ and Ar$_{12}$ may be the same or different.

In formula 1 above, m, n, o, and p each independently represent an integer of 0 to 2.

According to one embodiment of the present disclosure, formula 1 may be represented by any one of the following formulas 1-1 to 1-3:

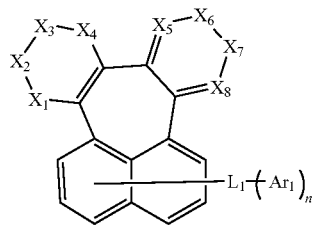

(1-1)

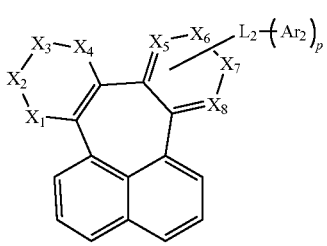

(1-2)

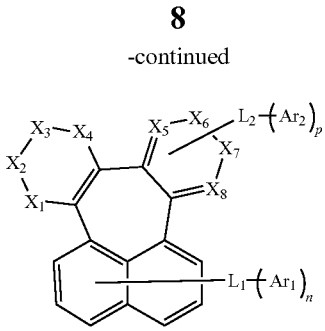

(1-3)

wherein X$_1$ to X$_8$ each independently represent N or CH; and L$_1$, L$_2$, Ar$_1$, Ar$_2$, n, and p are as defined in formula 1.

According to one embodiment of the present disclosure, formula 1 may be represented by the following formula 2-1 or 2-2:

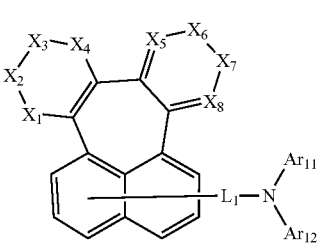

(2-1)

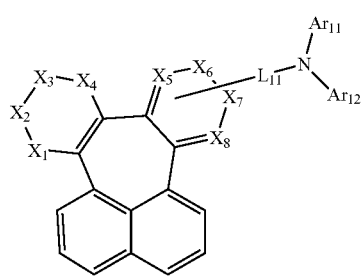

(2-2)

wherein X$_1$ to X$_8$ each independently represent N or CH; and L$_{11}$, Ar$_{11}$, and Ar$_{12}$ are as defined in formula 1.

According to one embodiment of the present disclosure, formula 1 may be represented by the following formula 3-1 or 3-2:

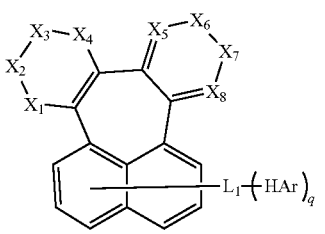

(3-1)

-continued

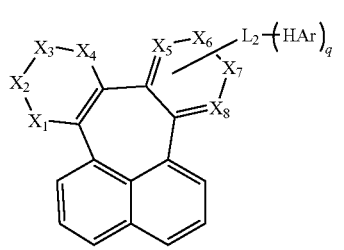

(3-2)

wherein HAr represents a substituted or unsubstituted electron-rich (3- to 30-membered)heteroaryl, according to one embodiment of the present disclosure, HAr represents a substituted or unsubstituted (3- to 30-membered)heteroaryl, according to another embodiment of the present disclosure, HAr represents a substituted or unsubstituted (5- to 25-membered)heteroaryl, and according to yet another embodiment of the present disclosure, HAr represents a (5- to 18-membered)heteroaryl unsubstituted or substituted with a (C6-C18)aryl(s). For example, HAr represents a diphenyltriazinyl, a phenylbiphenyltriazinyl, a quinazolinyl, a quinoxalinyl, a benzoquinazolinyl, a benzoquinoxalinyl, a dibenzofuranyl, a dibenzothiophenyl, etc.

In formulas 3-1 and 3-2 above, $X_1$ to $X_8$ each independently represent N or CH, q represents an integer of 0 to 2, and $L_1$ and $L_2$ are each independently as defined in formula 1.

In the formula of the present disclosure, the heteroaryl (ene) may contain at least one heteroatom selected from B, N, O, S, Si, and P. The heteroatom may be bonded with at least one substituent selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

The compound represented by formula 1 may be selected from the following compounds, but is not limited thereto:

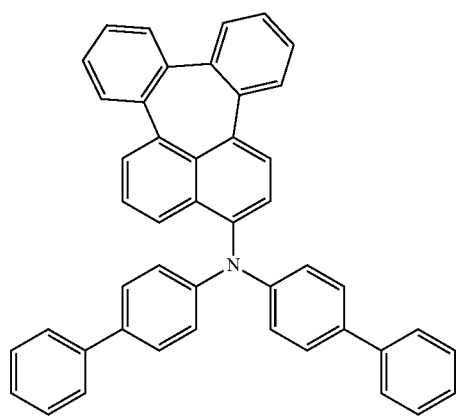

A-1

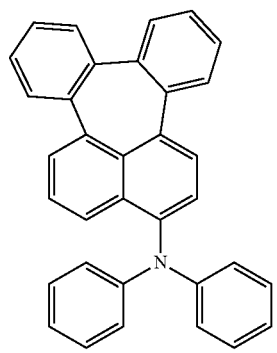

A-2

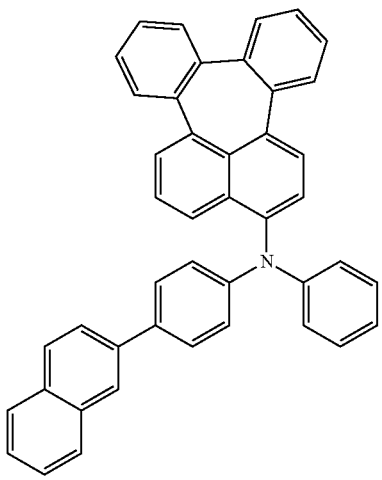

A-3

A-4

A-5
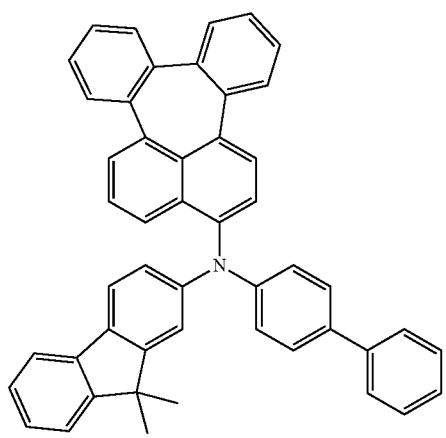
A-6
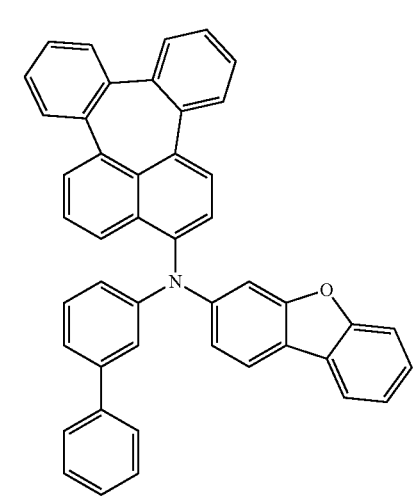
A-7
A-8
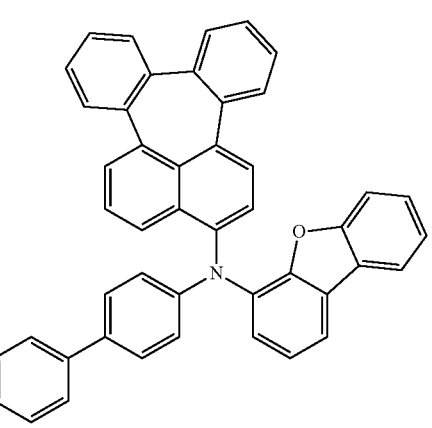
A-9
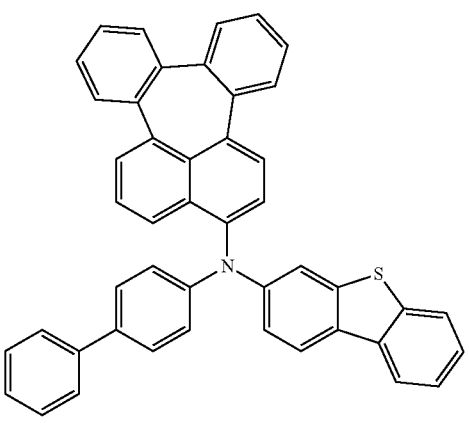
A-10
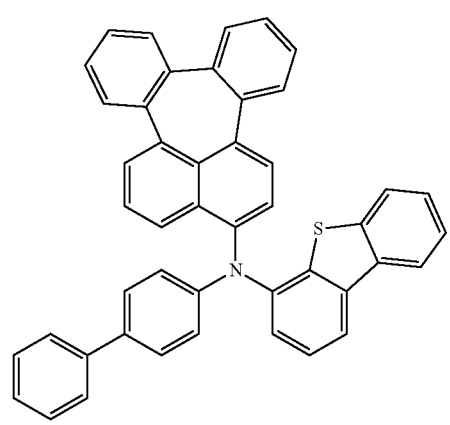

A-11
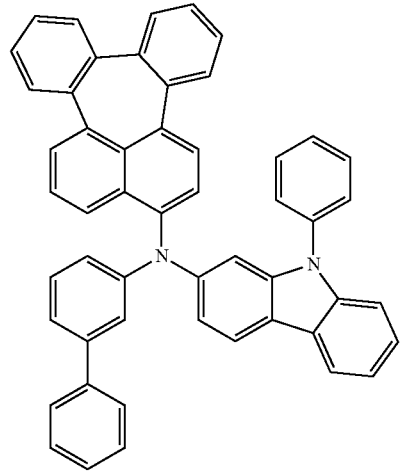
A-14
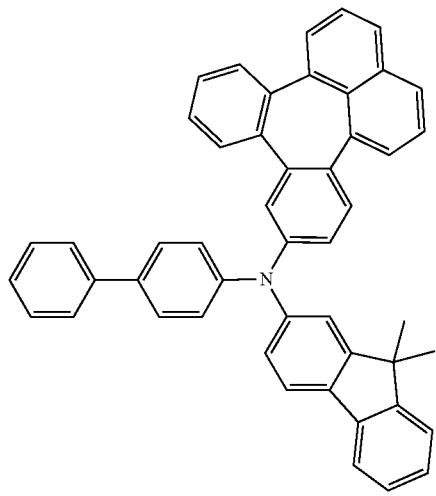
A-12
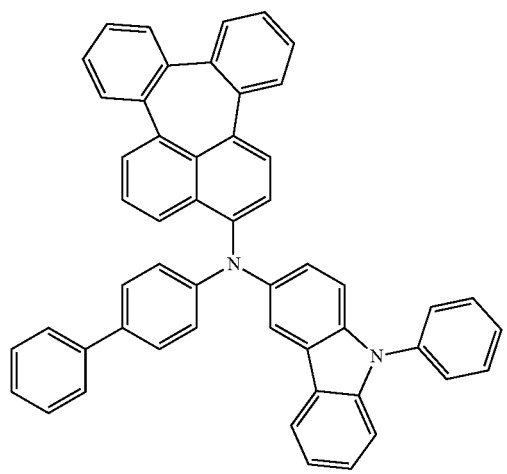
A-15
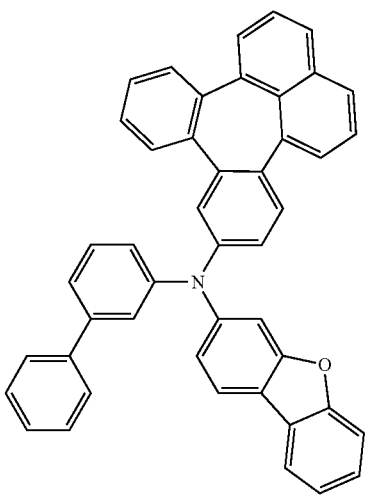
A-13
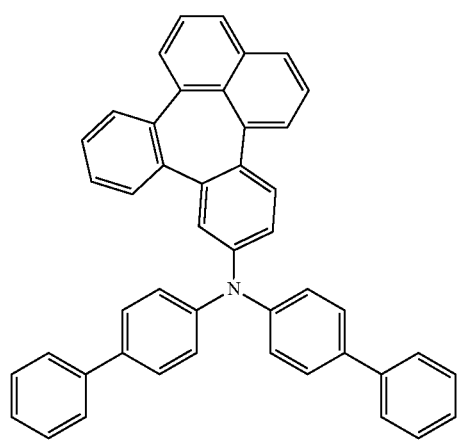
A-16
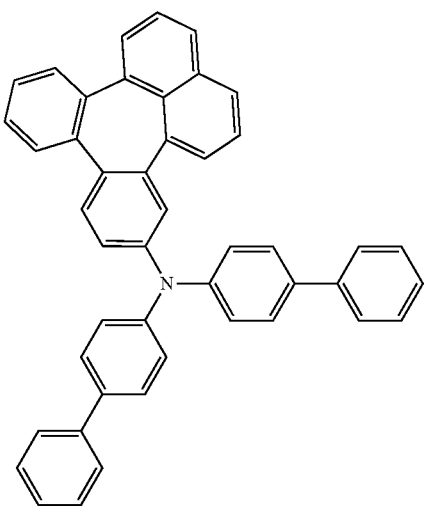

A-17
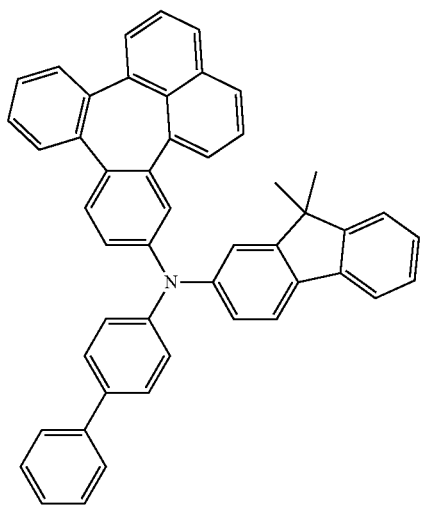
A-18
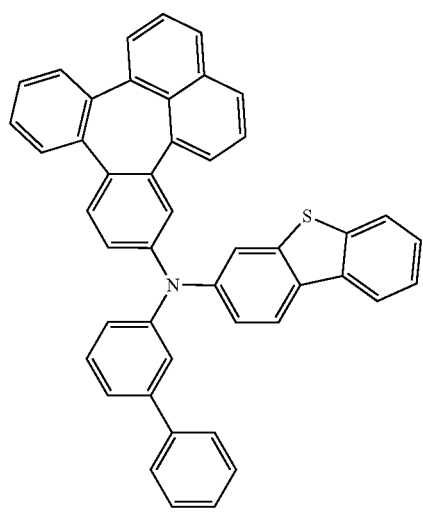
A-19
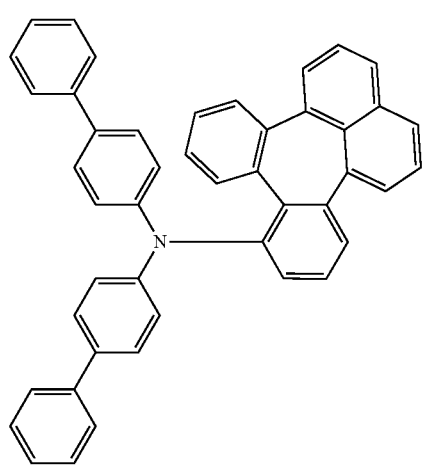
A-20
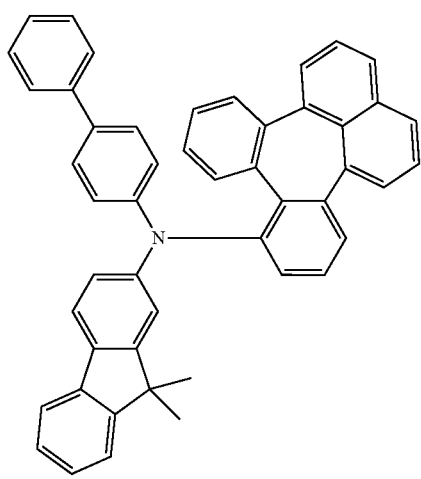
A-21
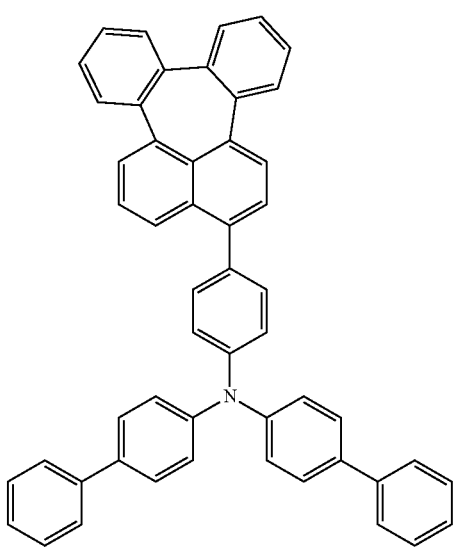
A-22
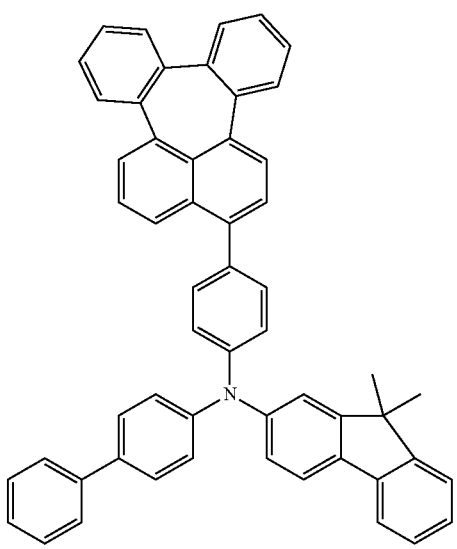

A-23
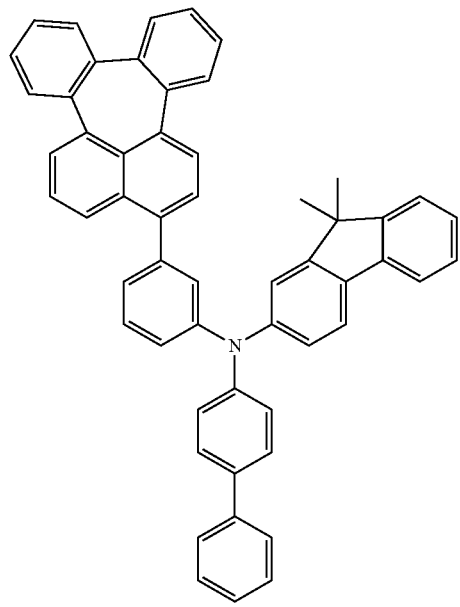
A-24
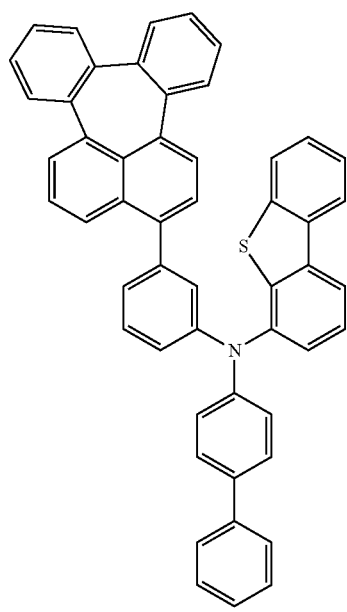
A-25
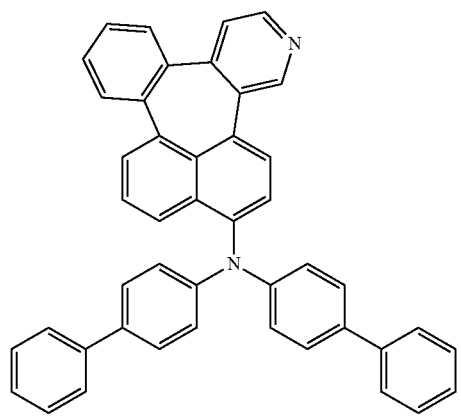
A-26
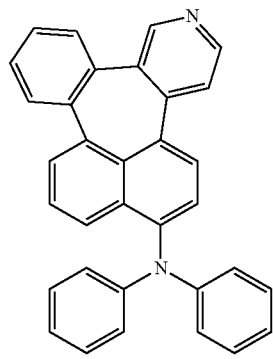
A-27
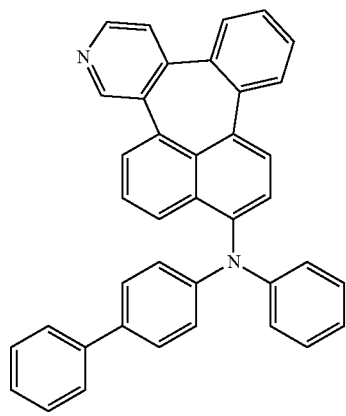
A-28
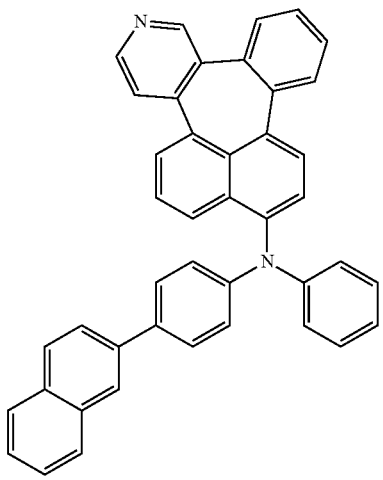

A-29
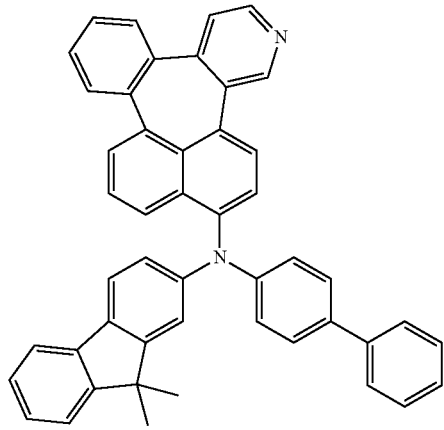
A-32
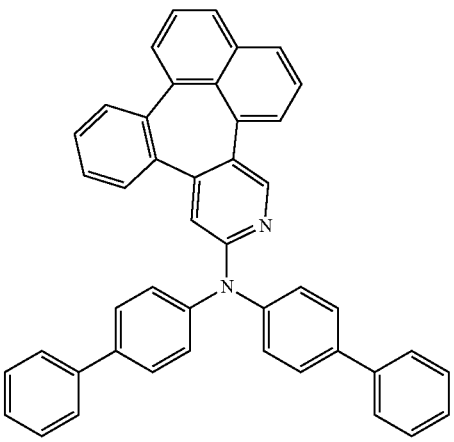
A-30
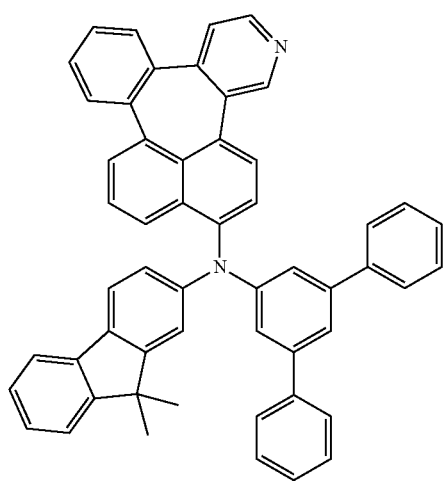
A-33
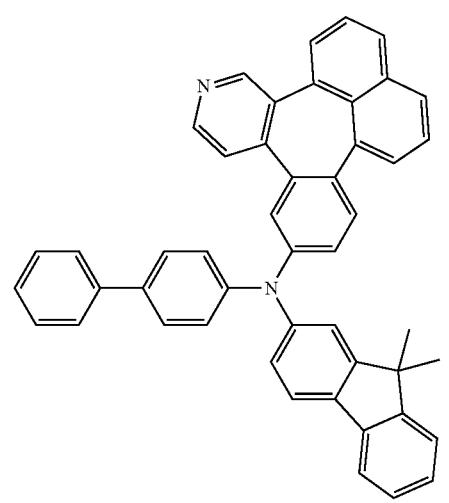
A-31
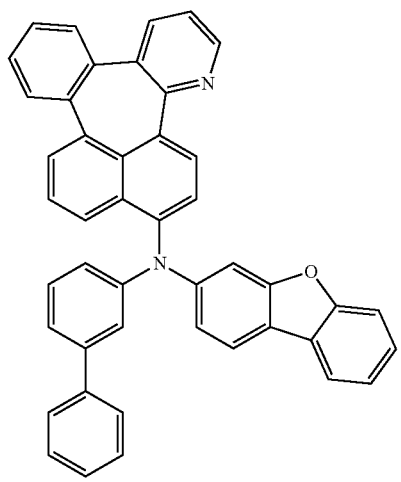
A-34
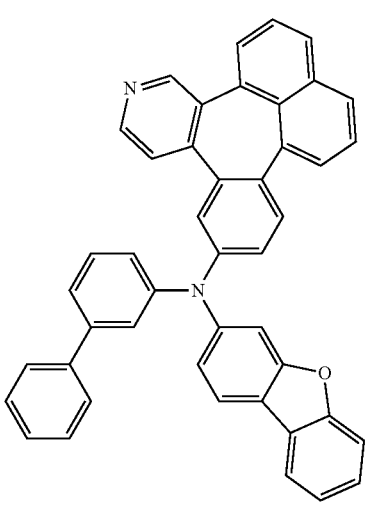

A-35
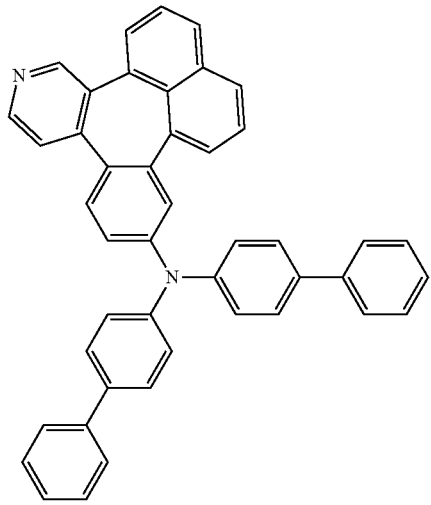
A-36
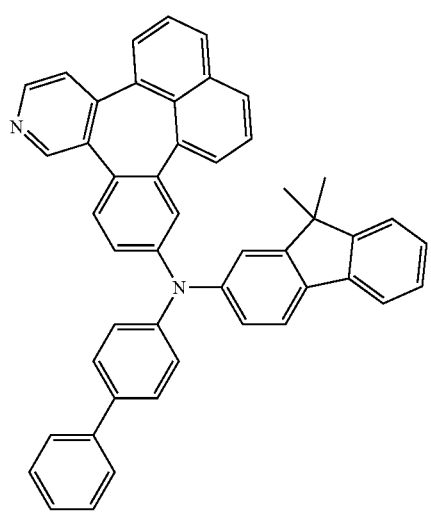
A-37
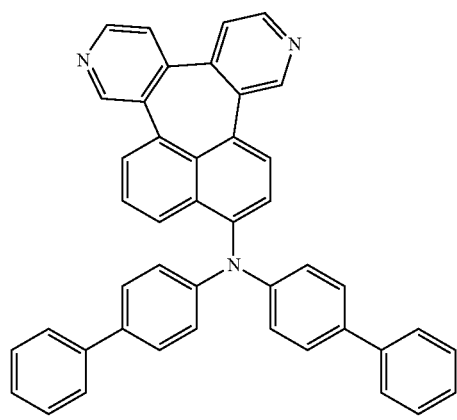
A-38
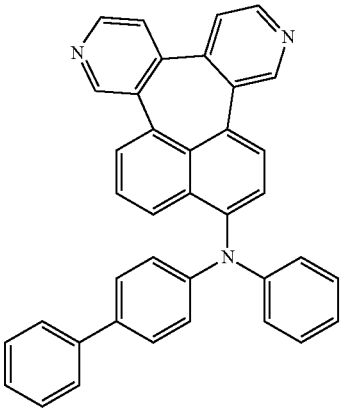
A-39
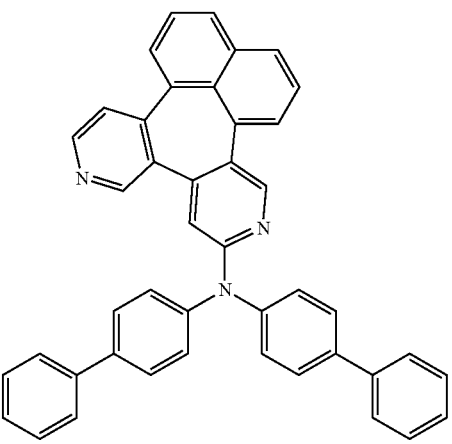
A-40
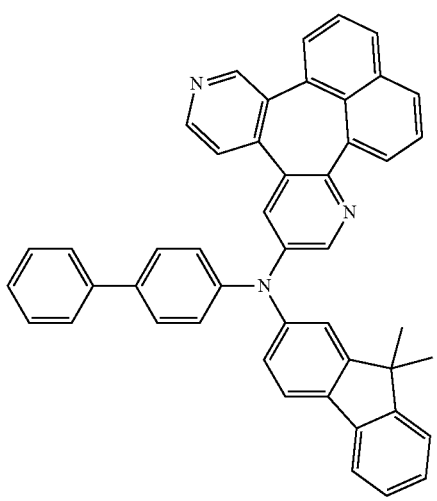

A-41
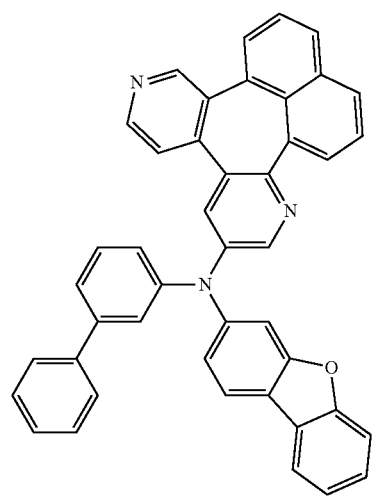
A-44
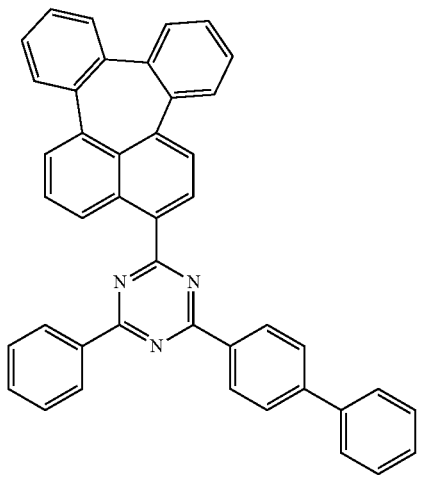
A-42
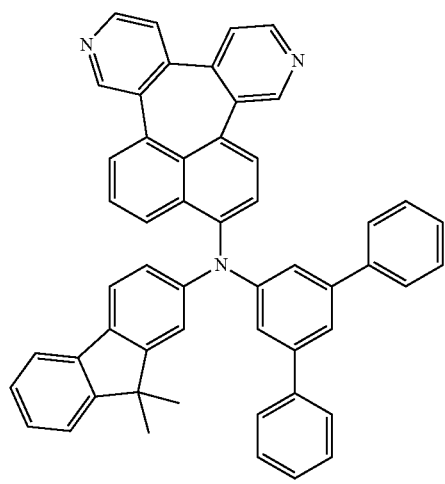
A-45
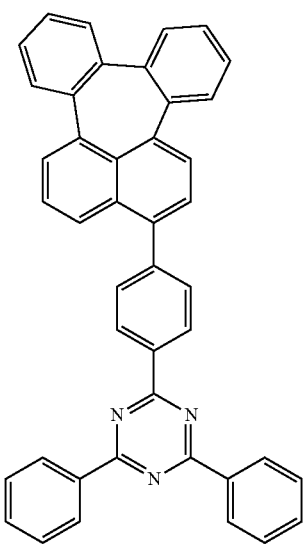
A-43
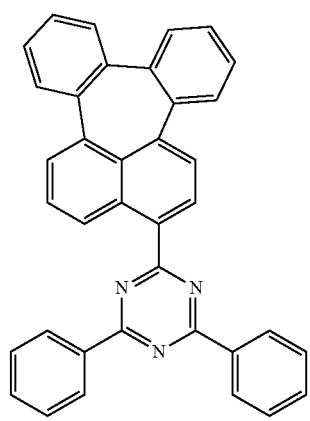
A-46
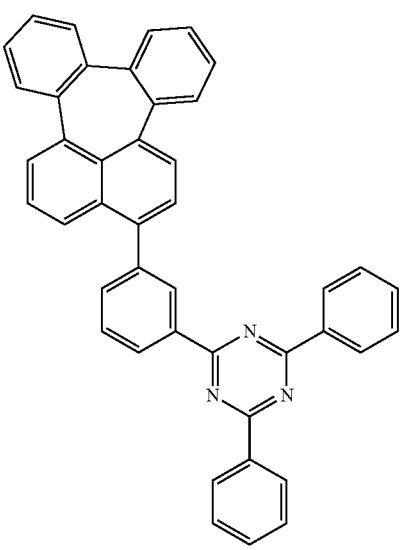

A-47
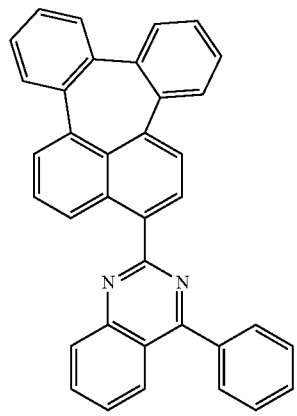
A-48
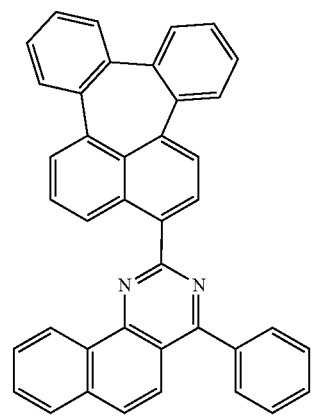
A-49
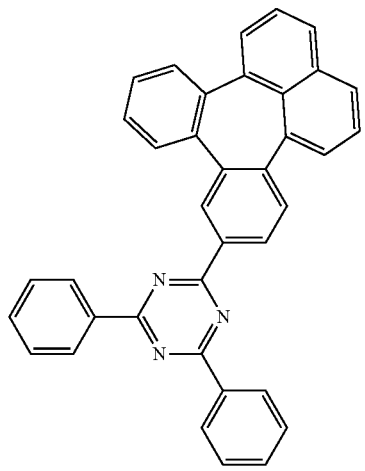
A-50
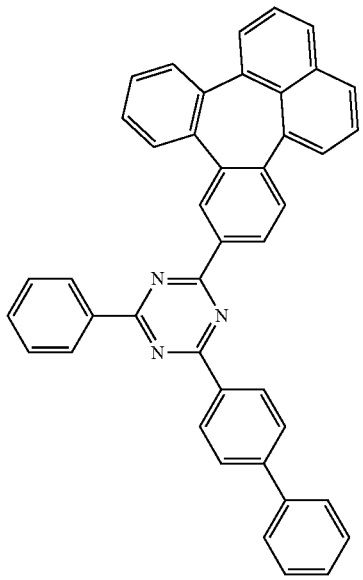
A-51
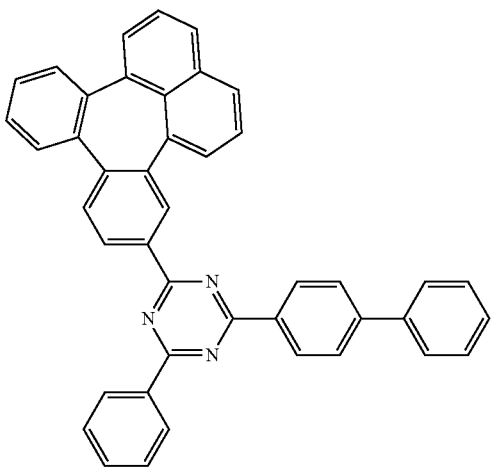
A-52
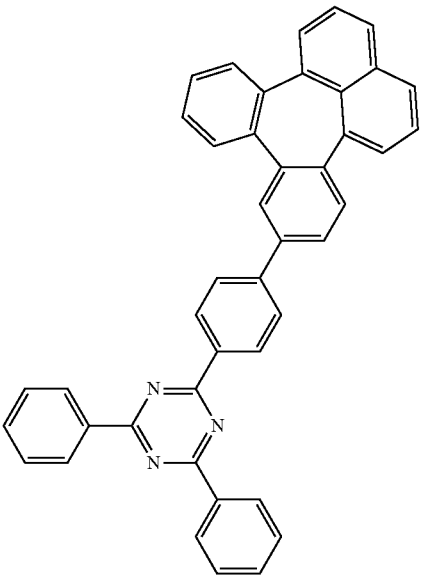

A-53
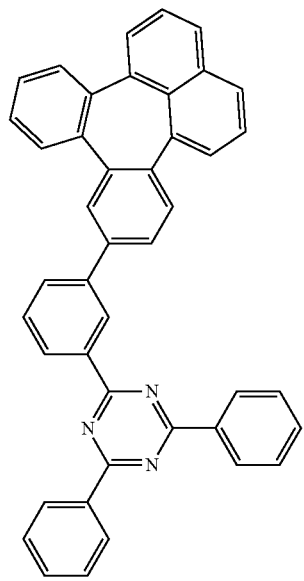
A-54
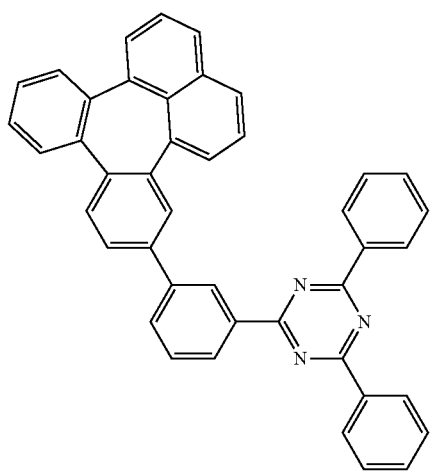
A-55
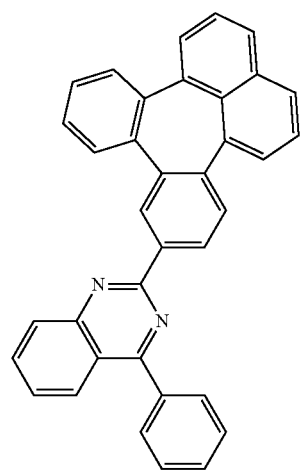
A-56
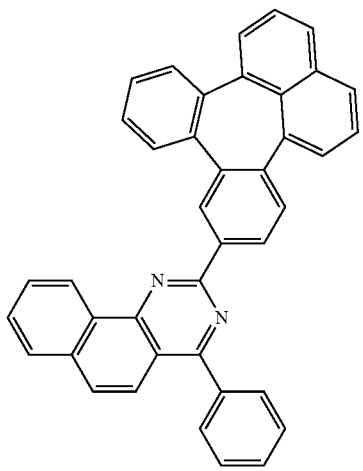
A-57
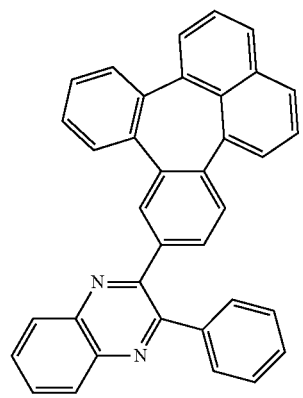
A-58
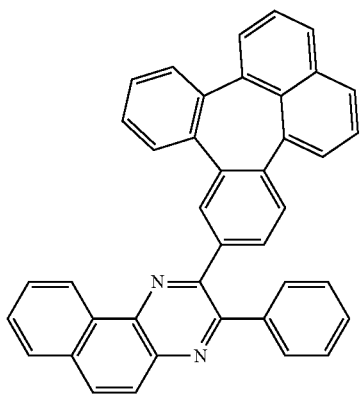

A-59
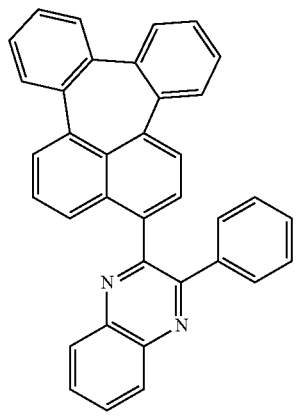
A-60
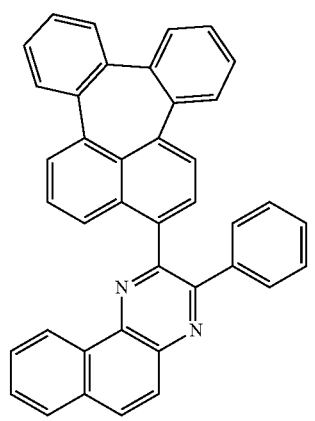
A-61
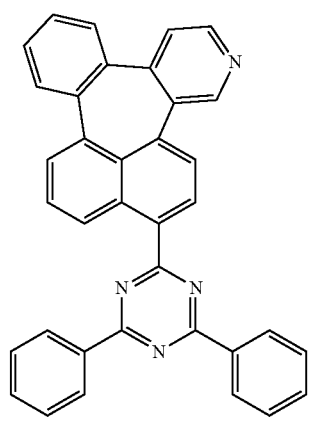
A-62
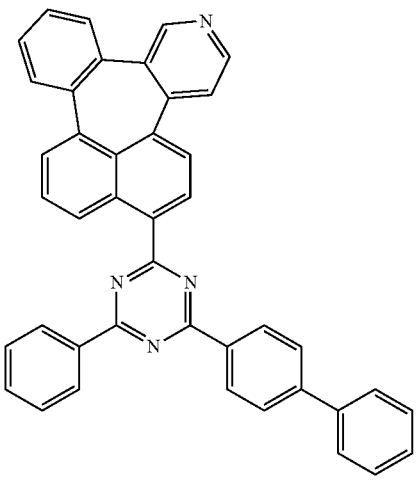
A-63
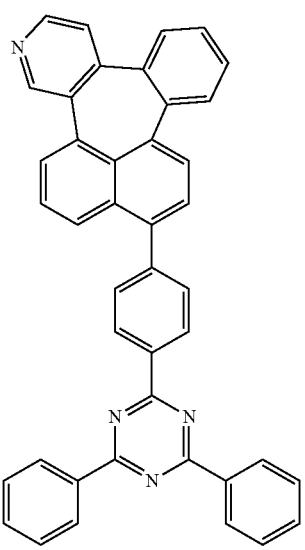
A-64
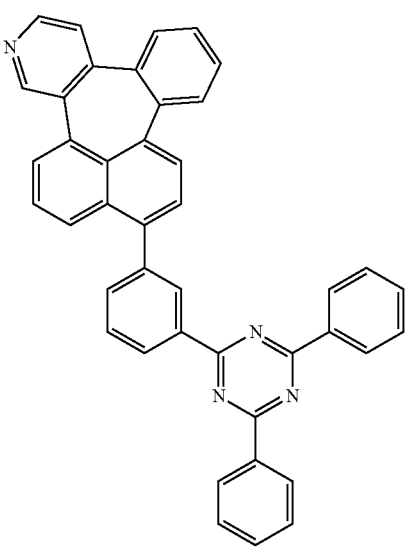

A-65
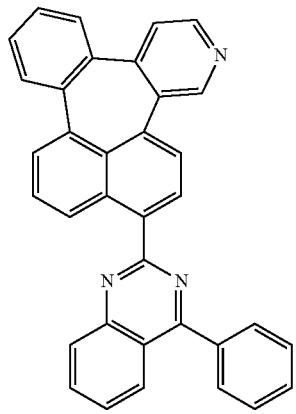
A-66
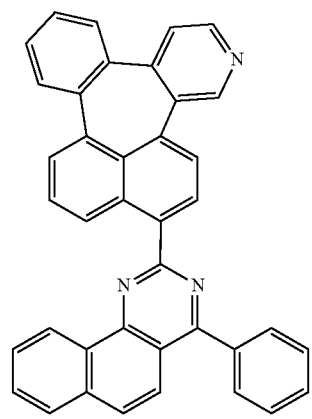
A-67
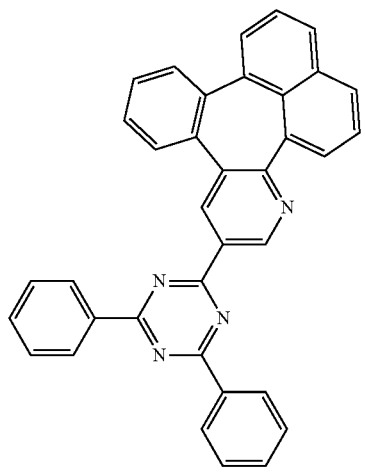
A-68
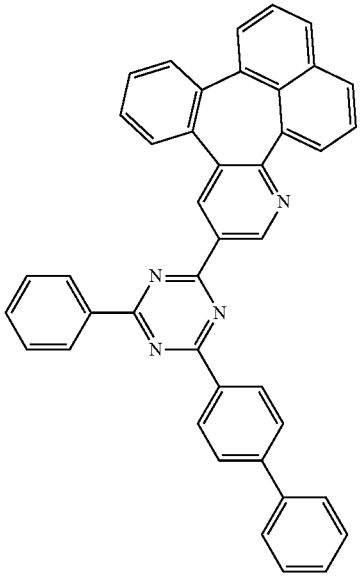
A-69
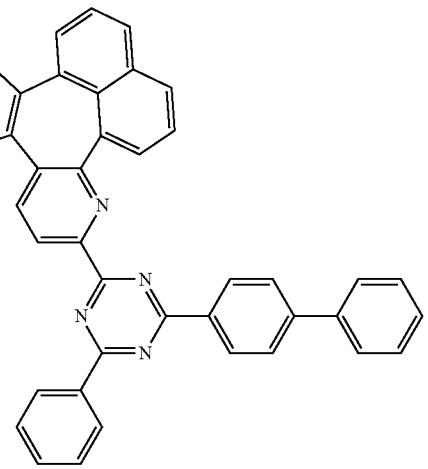
A-70
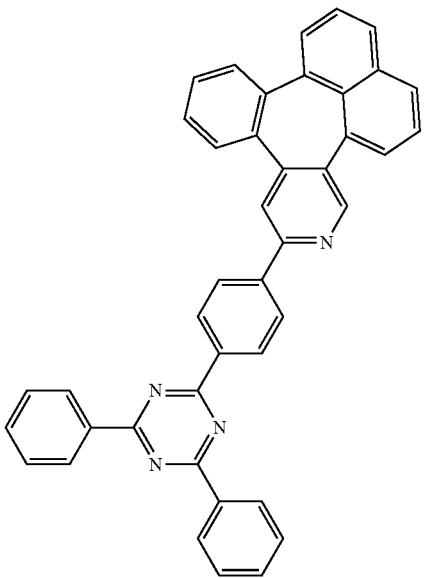

A-71
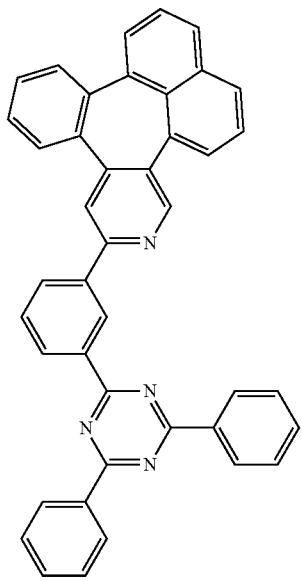
A-72
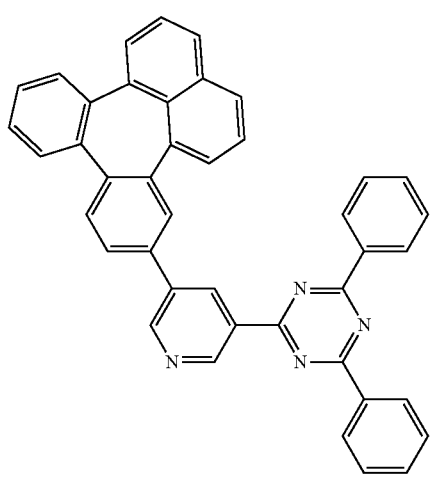
A-73
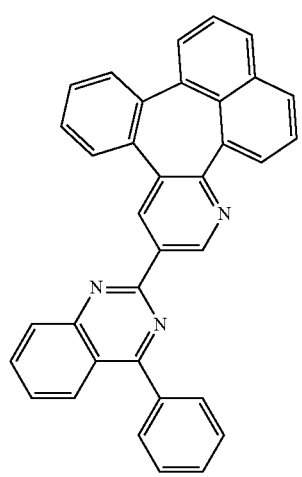
A-74
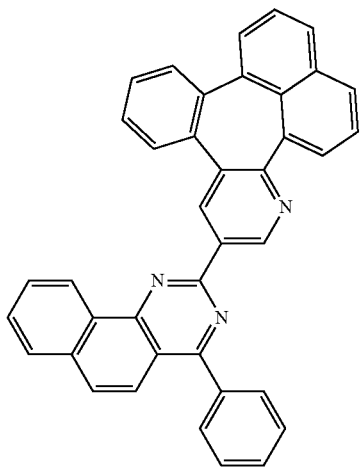
A-75
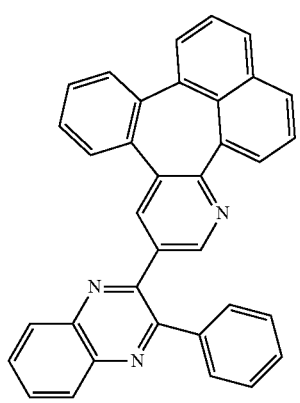
A-76
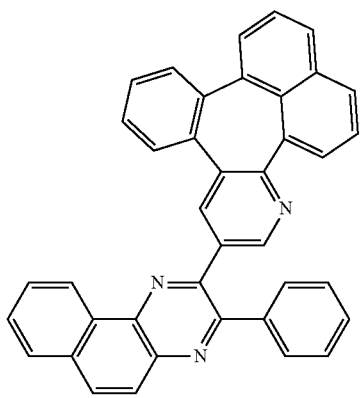

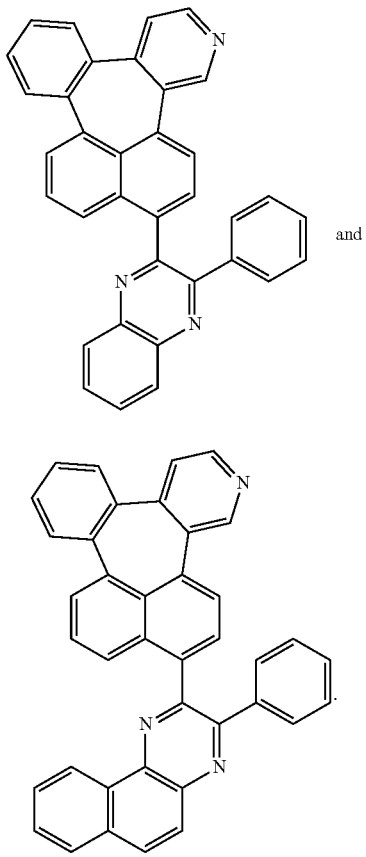

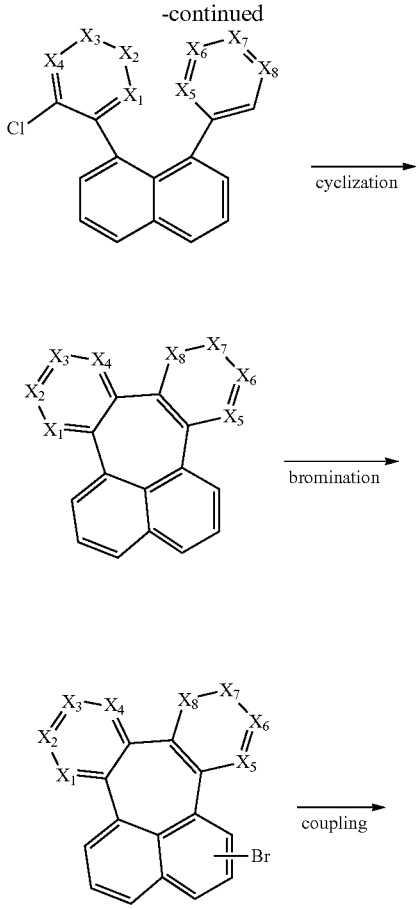

The compound of formula (1) according to the present disclosure can be prepared by a synthetic method known to a person skilled in the art. For example, the compound of formula (1) can be prepared according to the following reaction scheme 1, but is not limited thereto:

[Reaction Scheme 1]

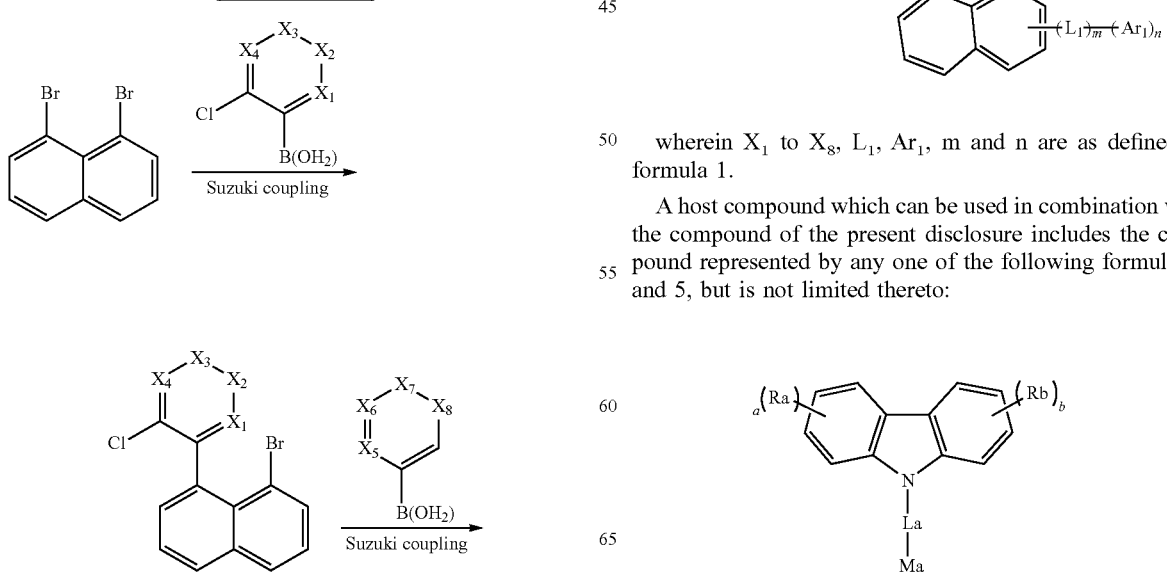

wherein $X_1$ to $X_8$, $L_1$, $Ar_1$, m and n are as defined in formula 1.

A host compound which can be used in combination with the compound of the present disclosure includes the compound represented by any one of the following formulas 4 and 5, but is not limited thereto:

-continued

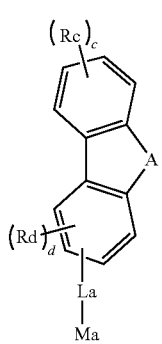

(5)

wherein

Ma represents a substituted or unsubstituted (C6-C30) aryl, a substituted or unsubstituted mono- or di-(C6-C30) arylamino, or a substituted or unsubstituted (3- to 30-membered)heteroaryl;

La represents a single bond, a substituted or unsubstituted (C6-C30)arylene, or a substituted or unsubstituted (3- to 30-membered)heteroarylene;

A represents S, O, $NR_7$, or $CR_8R_9$;

Ra to Rd each independently represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted (C1-C30)alkyl(C6-C30)arylamino, or a substituted or unsubstituted mono- or di-(C6-C30)arylamino; or are linked to an adjacent substituent(s) to form a substituted or unsubstituted, mono- or polycyclic, (3- to 30-membered) alicyclic or aromatic ring, or a combination thereof, in which the carbon atom of the formed ring may be substituted to at least one heteroatom selected from nitrogen, oxygen, and sulfur;

$R_7$ to $R_9$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or $R_8$ and $R_9$ are linked to each other to form a substituted or unsubstituted, mono- or polycyclic, (3- to 30-membered) alicyclic or aromatic ring, or a combination thereof, in which the carbon atom of the formed ring may be substituted to at least one heteroatom selected from nitrogen, oxygen, and sulfur; and a to c each independently represent an integer of 1 to 4, and d represents an integer of 1 to 3.

The compound represented by any one of formulas 4 and 5 includes the following compounds, but is not limited thereto:

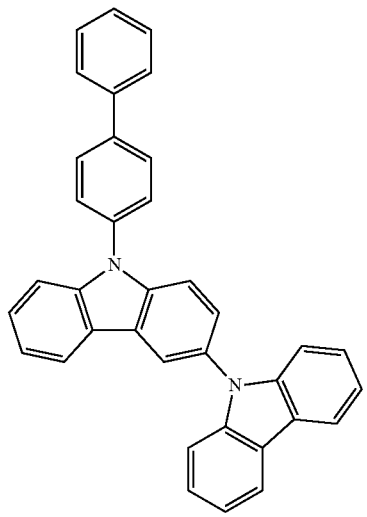

H-1

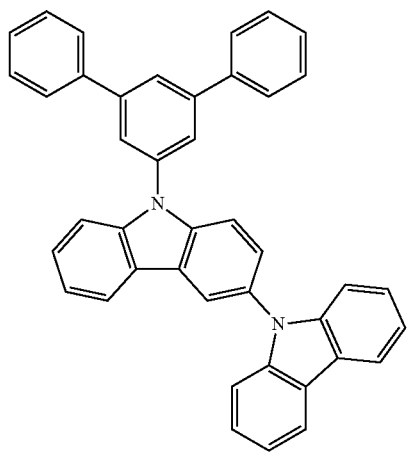

H-2

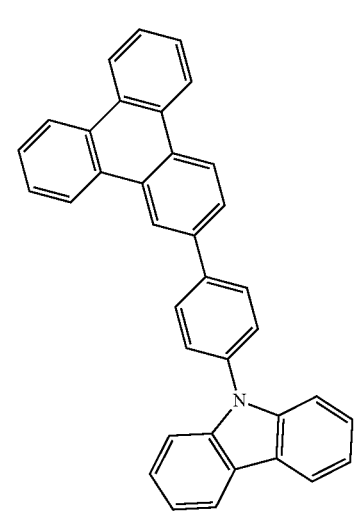

H-3

H-4
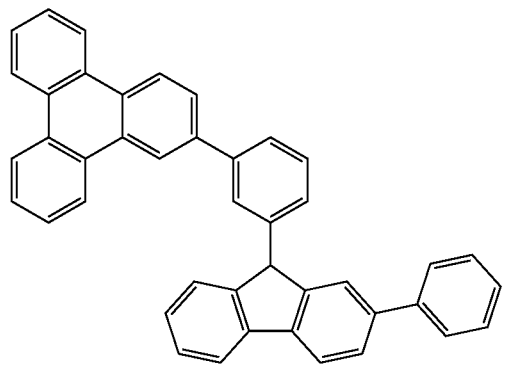
H-5
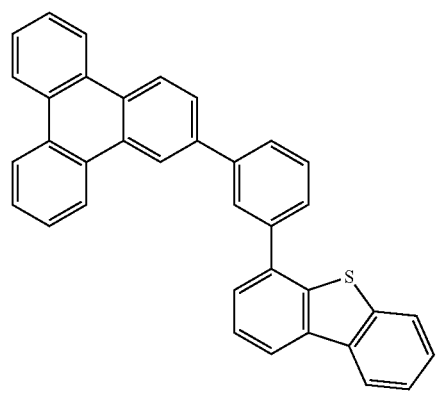
H-6
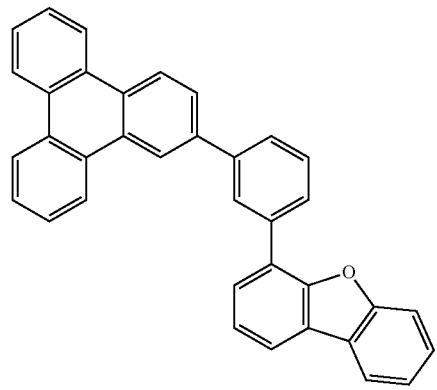
H-7
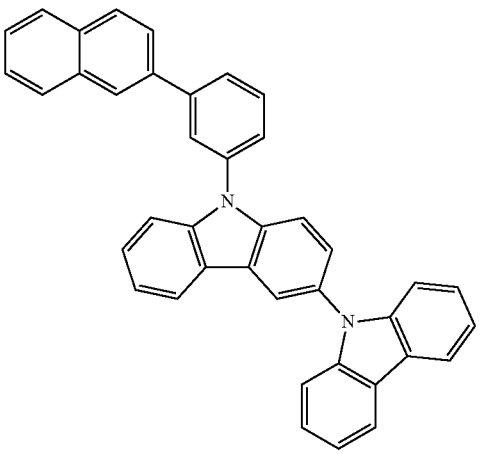
H-8
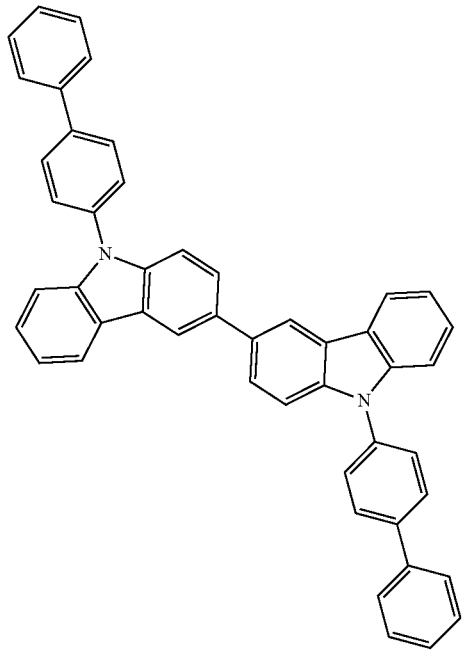
H-9
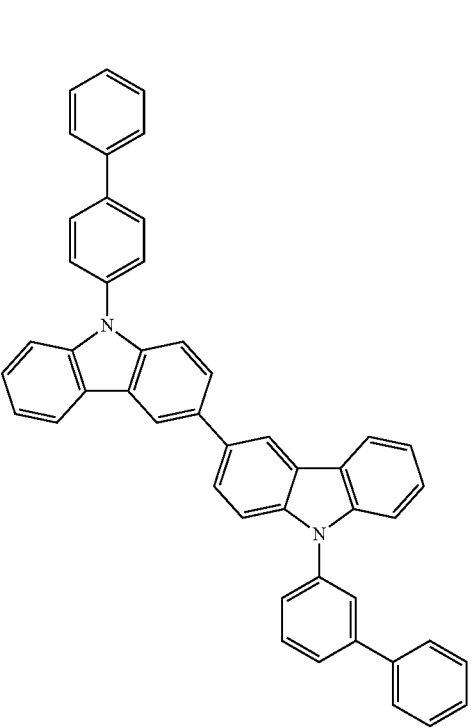

-continued
H-10
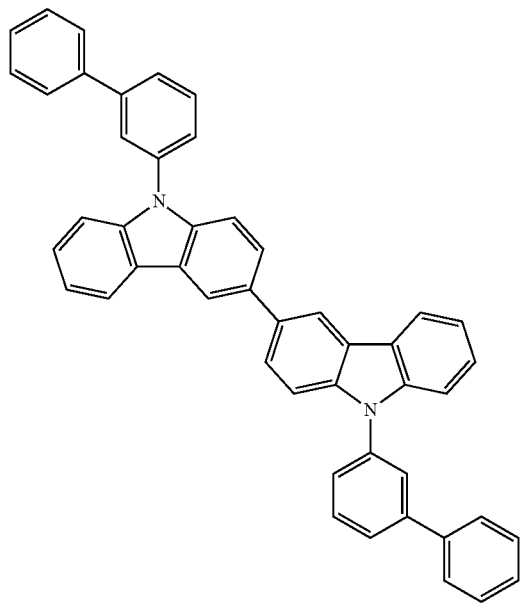
H-11
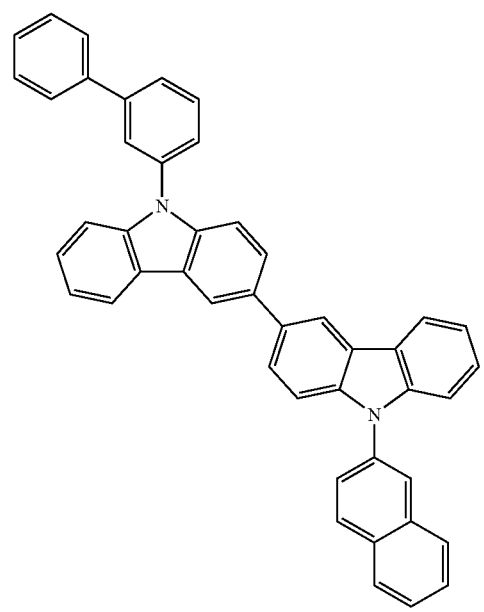
H-12
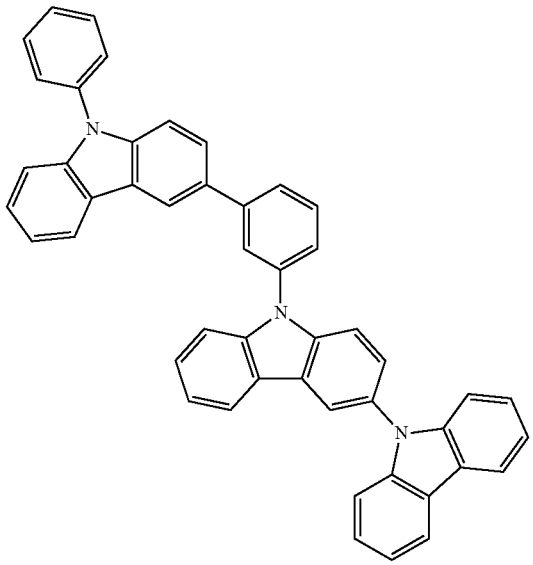
H-13
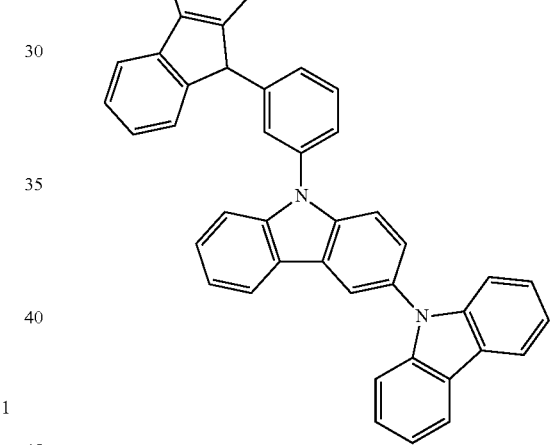
H-14
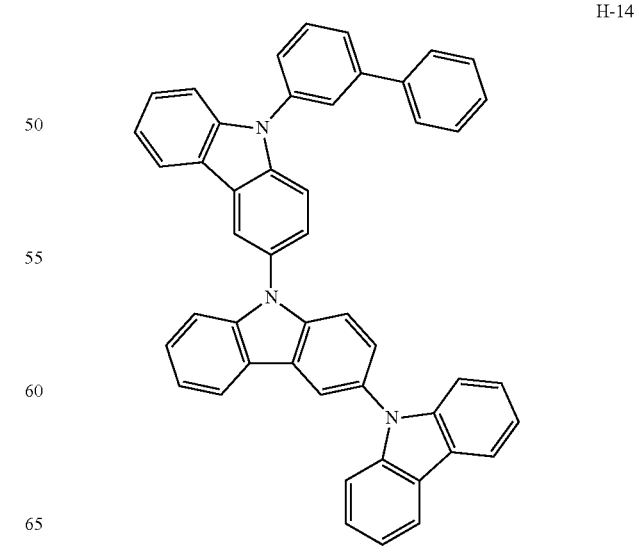

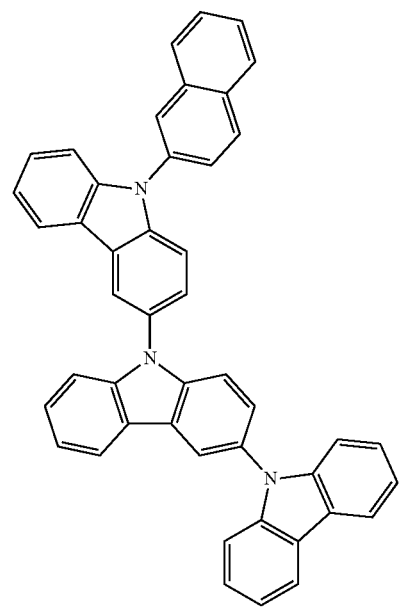
H-15
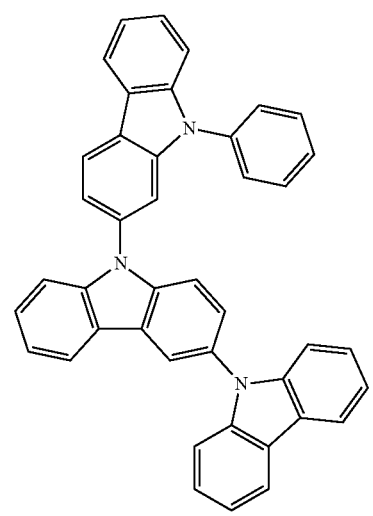
H-16
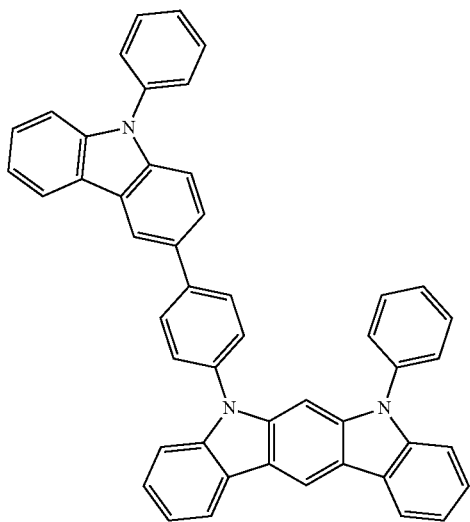
H-17
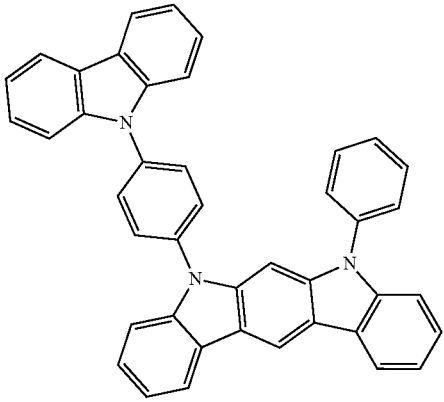
H-18
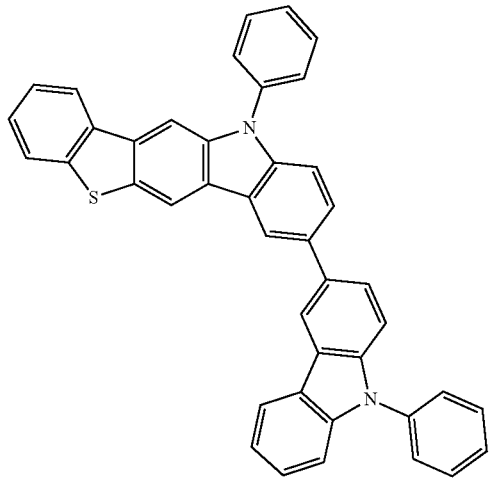
H-19
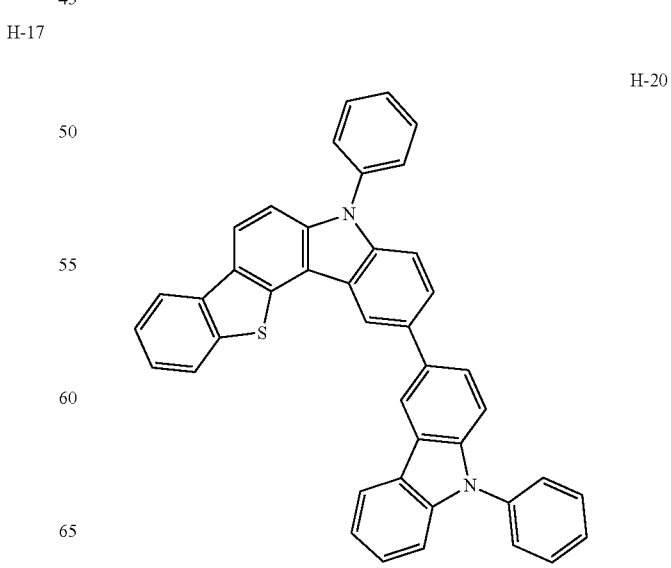
H-20

-continued
H-21
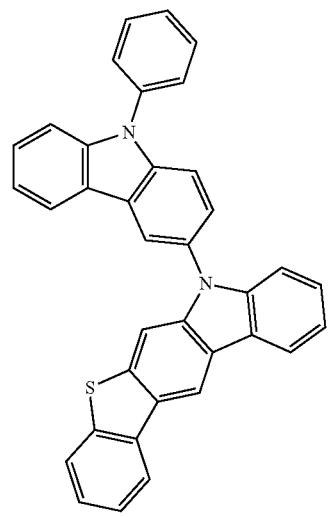
H-22
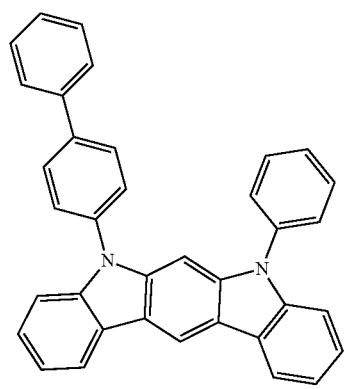
H-23
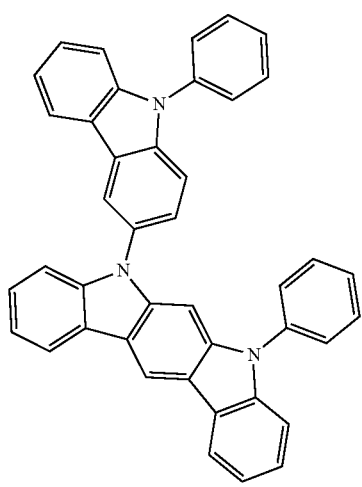
-continued
H-24
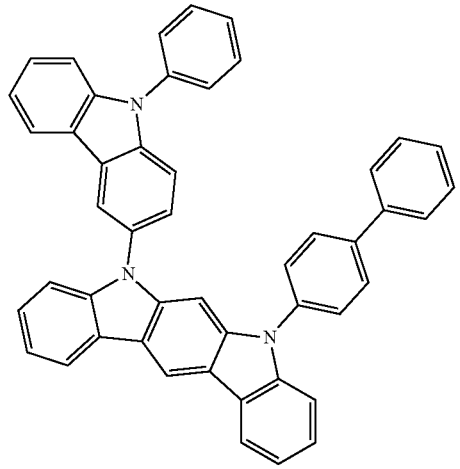
H-25
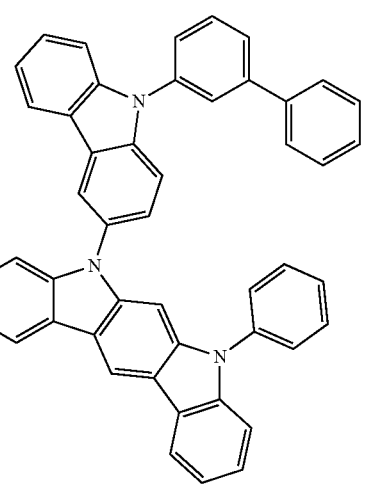
H-26
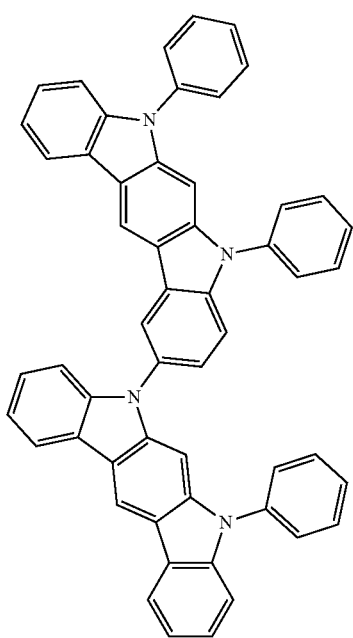

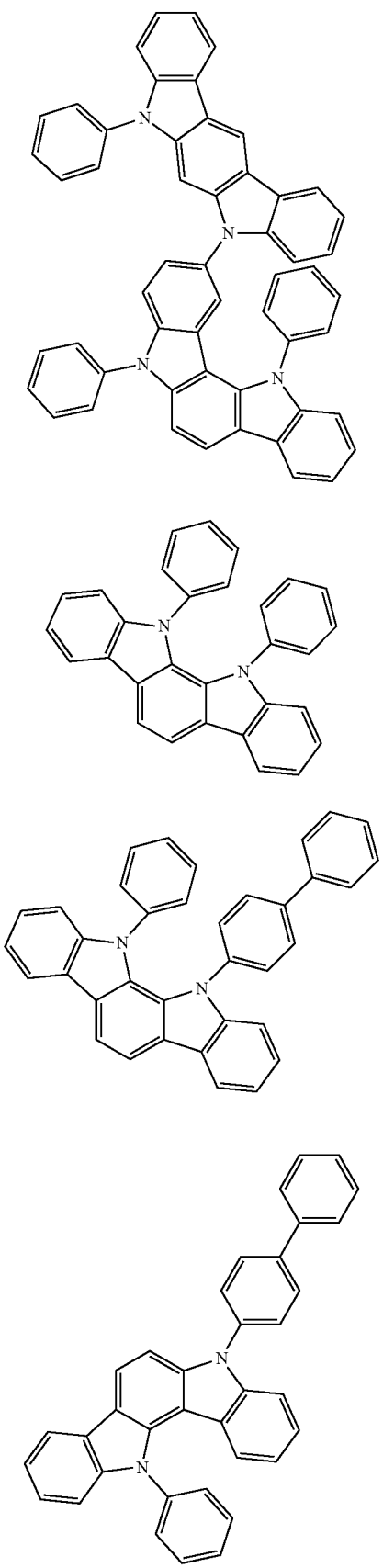
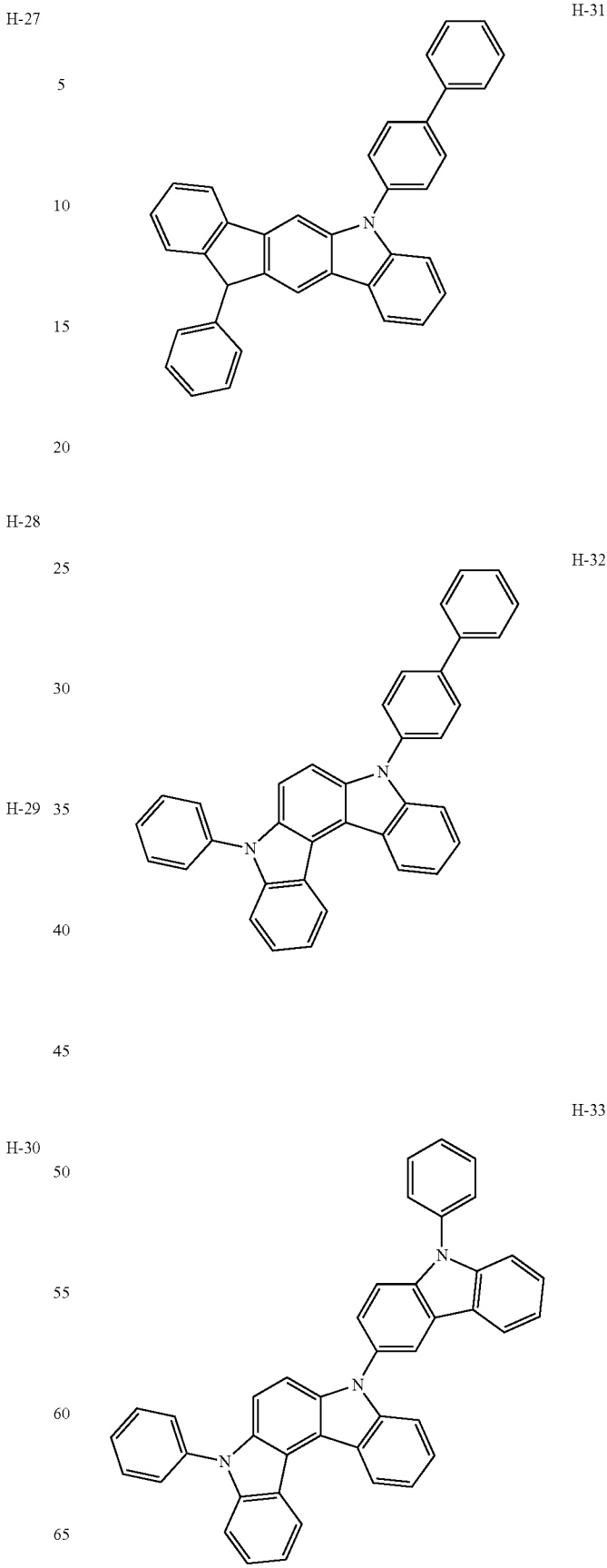

-continued
H-34
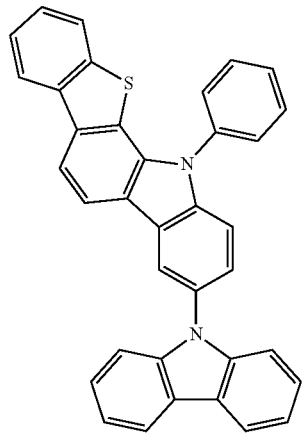
H-37
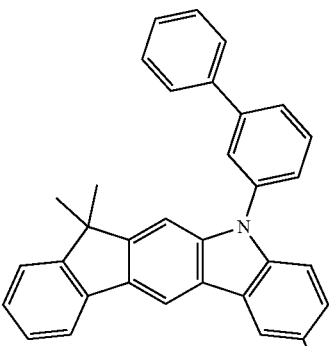
H-35
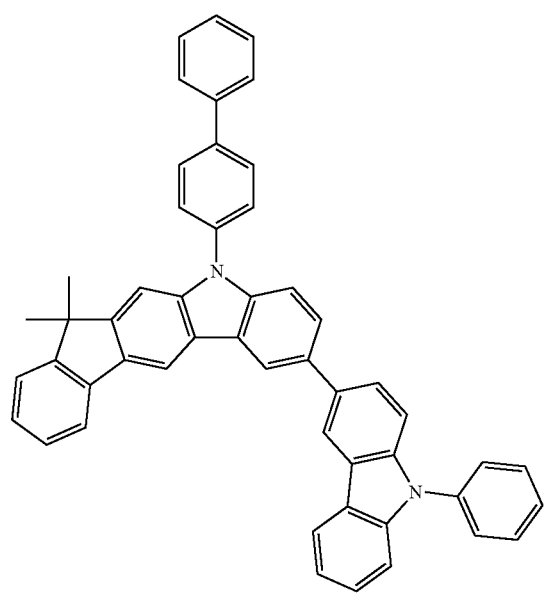
H-38
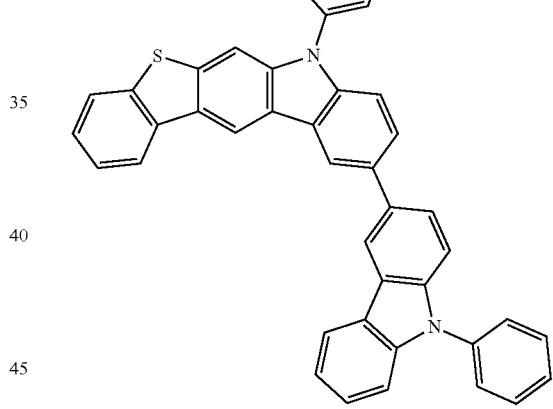
H-36
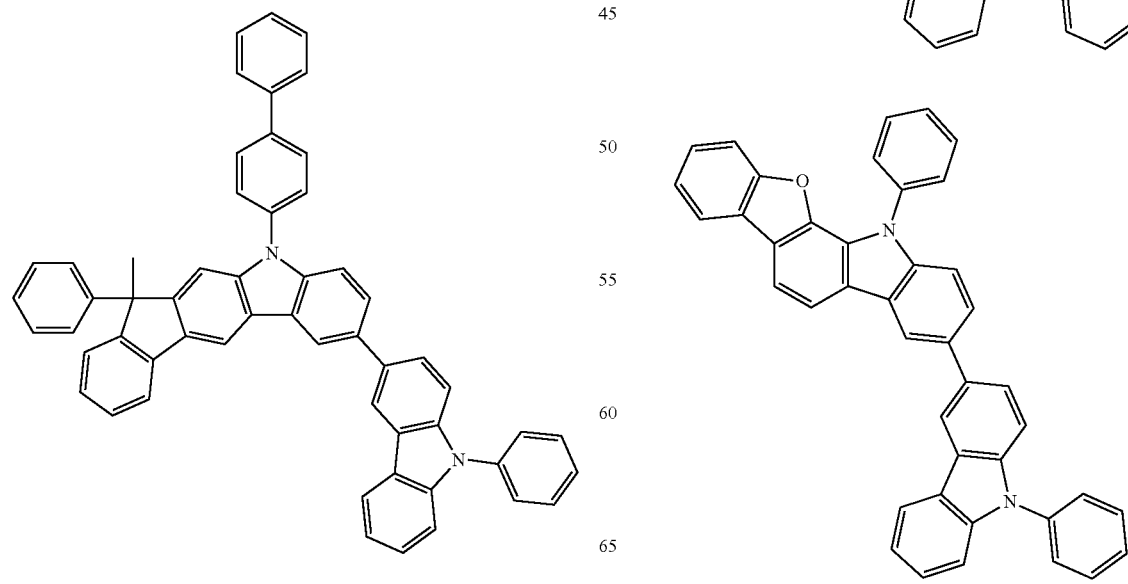
H-39

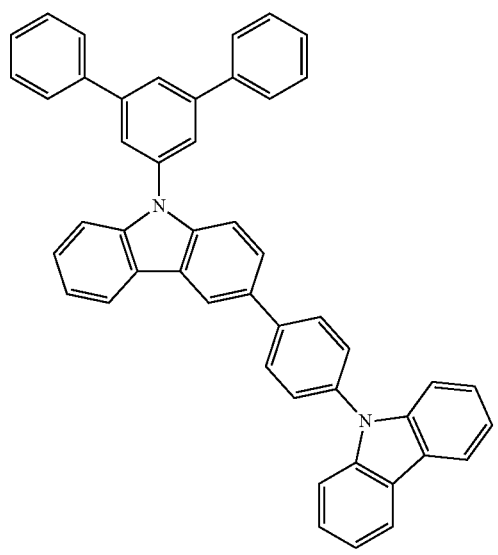
H-40
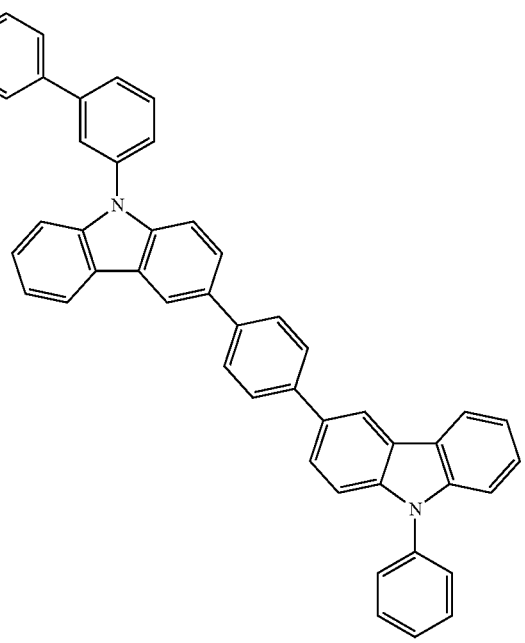
H-42
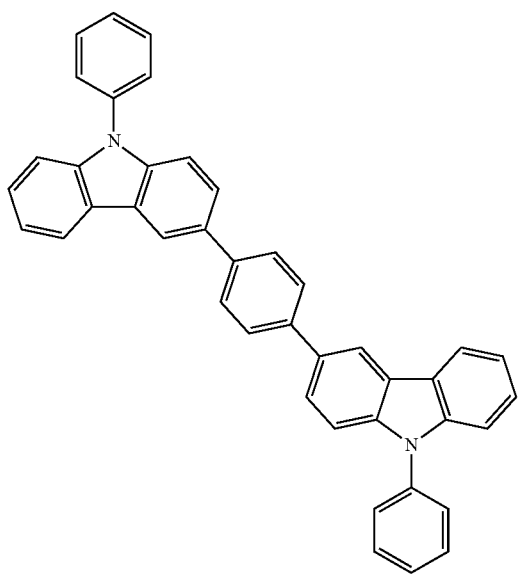
H-41
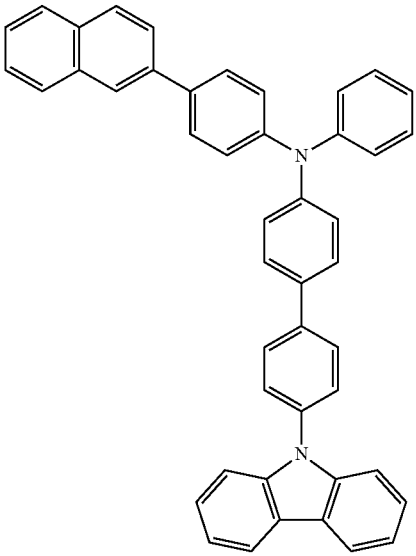
H-43

H-44
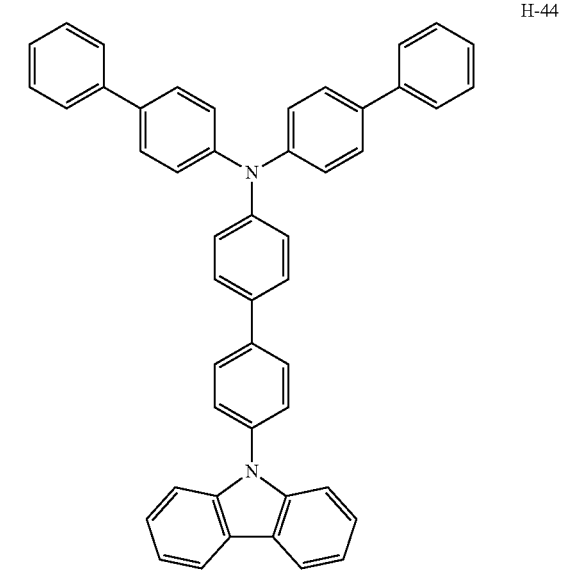
H-45
H-46
H-47
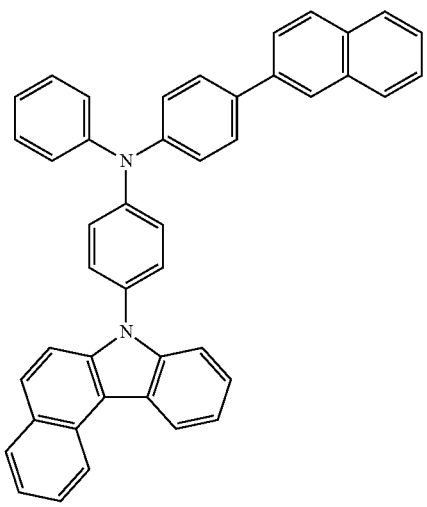
H-48
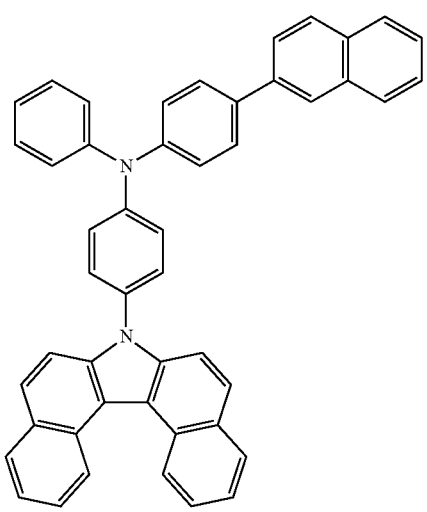
H-49
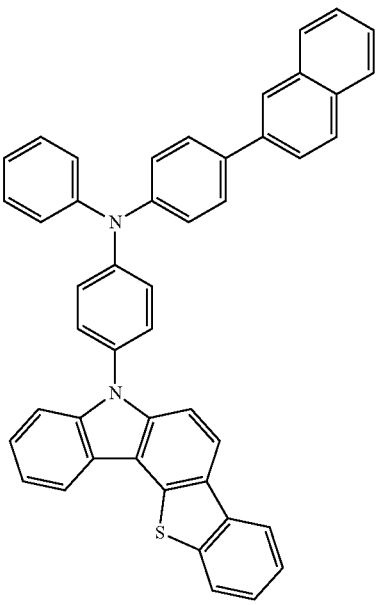

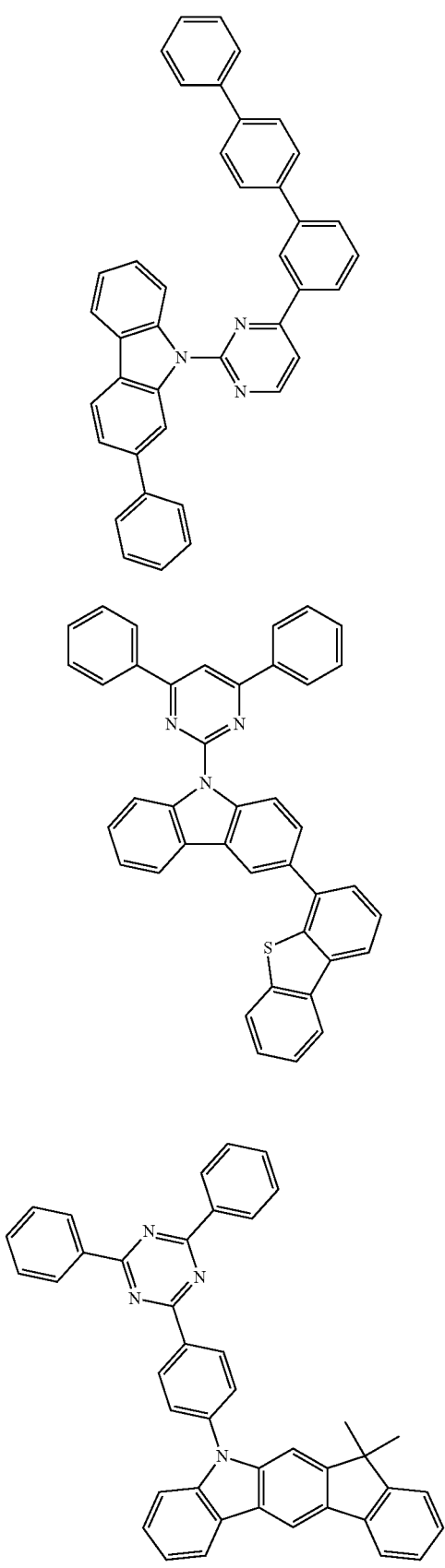
H-50
H-51
H-52
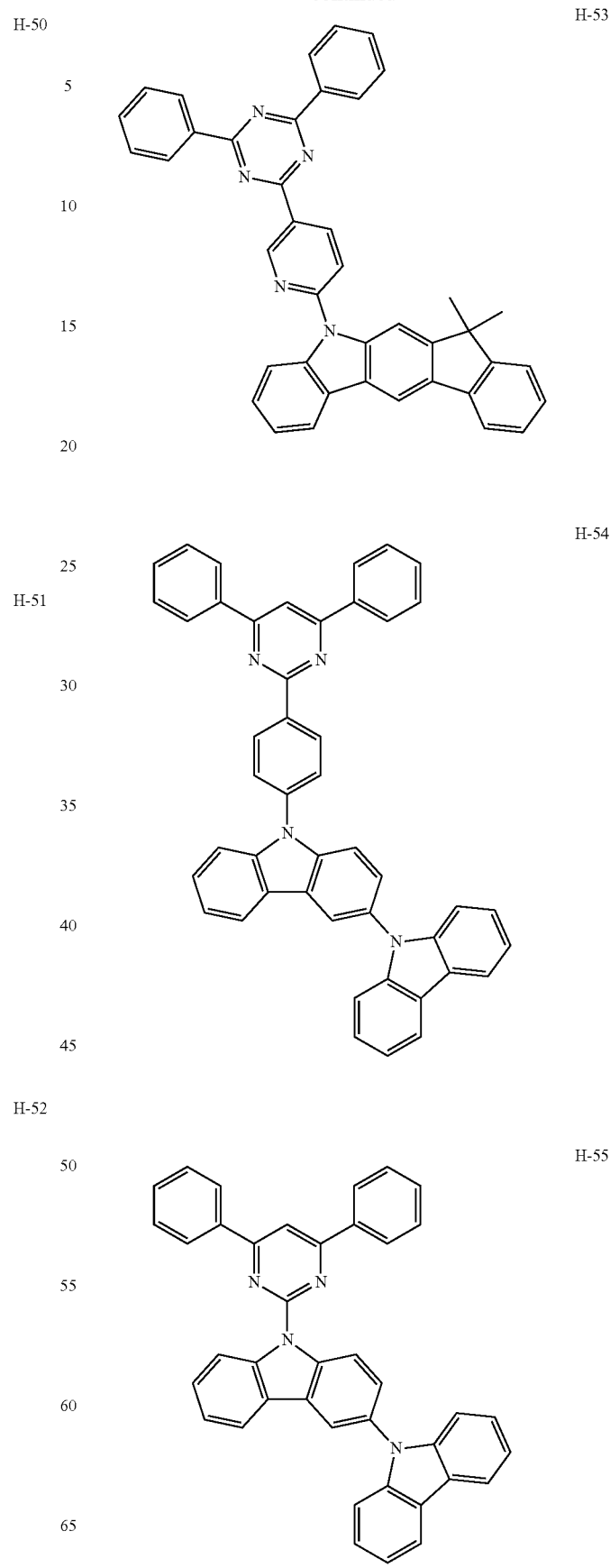
H-53
H-54
H-55

-continued
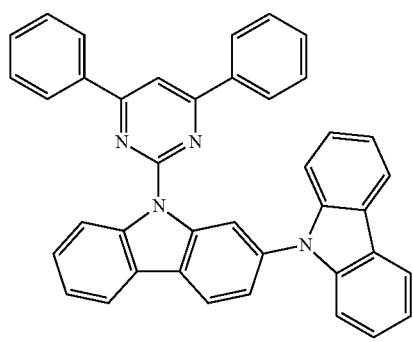
H-56
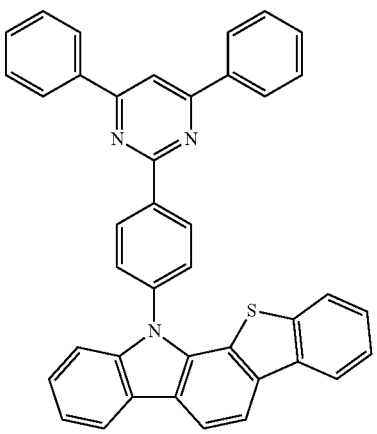
H-60
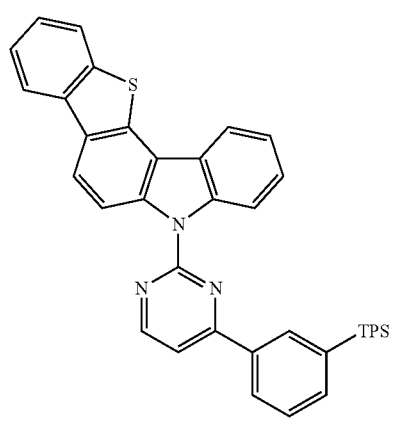
H-57
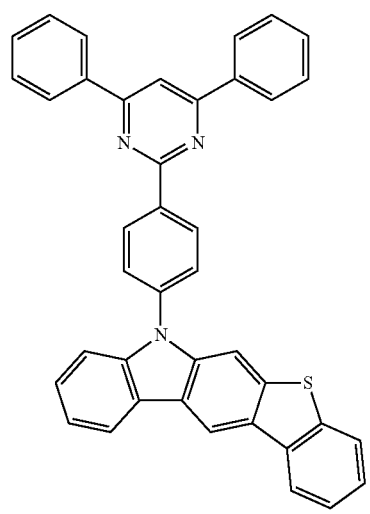
H-61
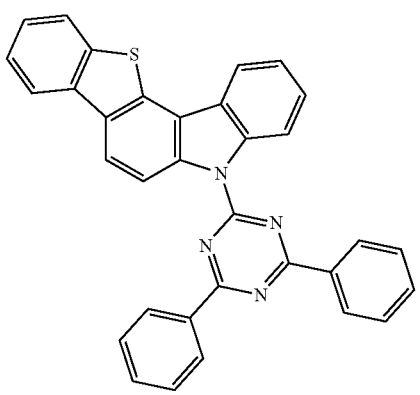
H-58
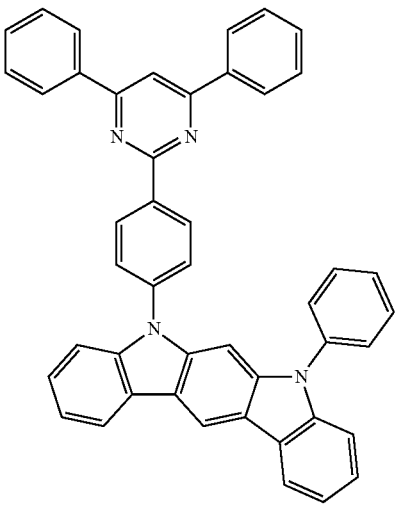
H-62
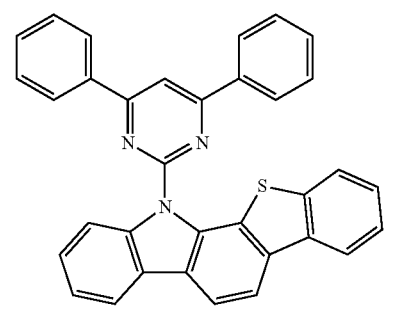
H-59

H-63
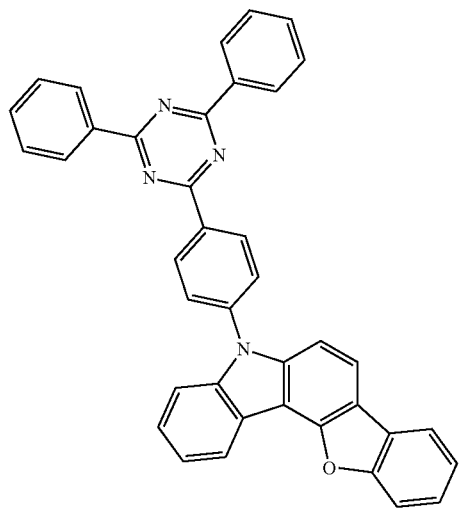
H-64
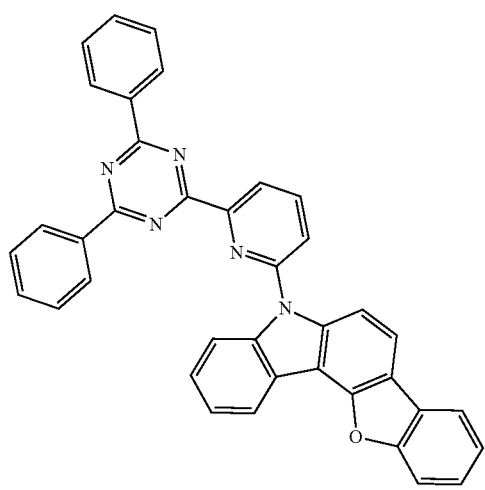
H-65
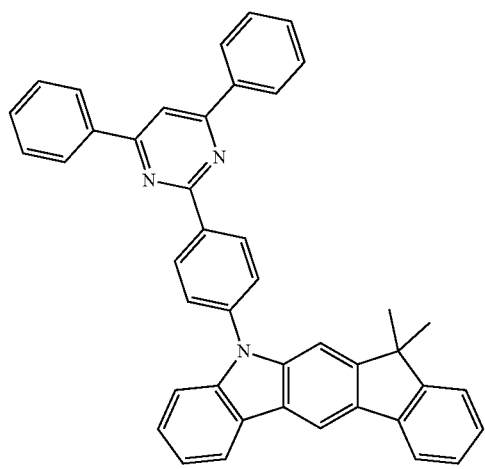
H-66
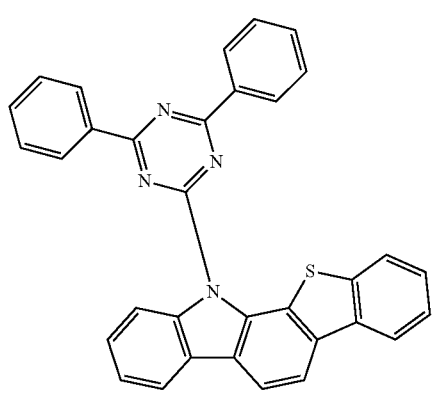
H-67
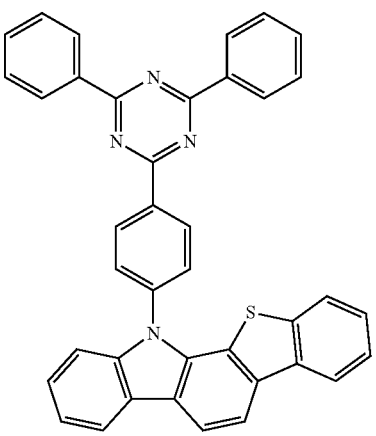
H-68
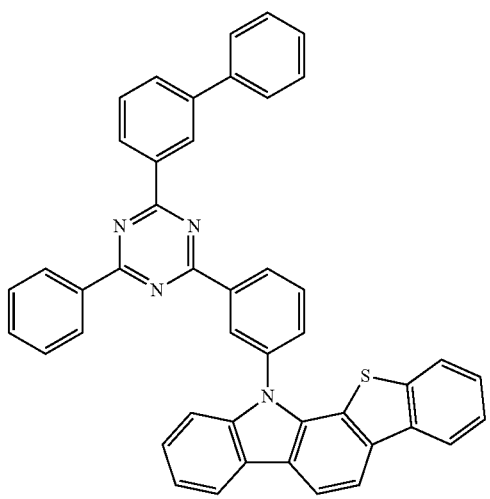

H-69
H-70
H-71
H-72
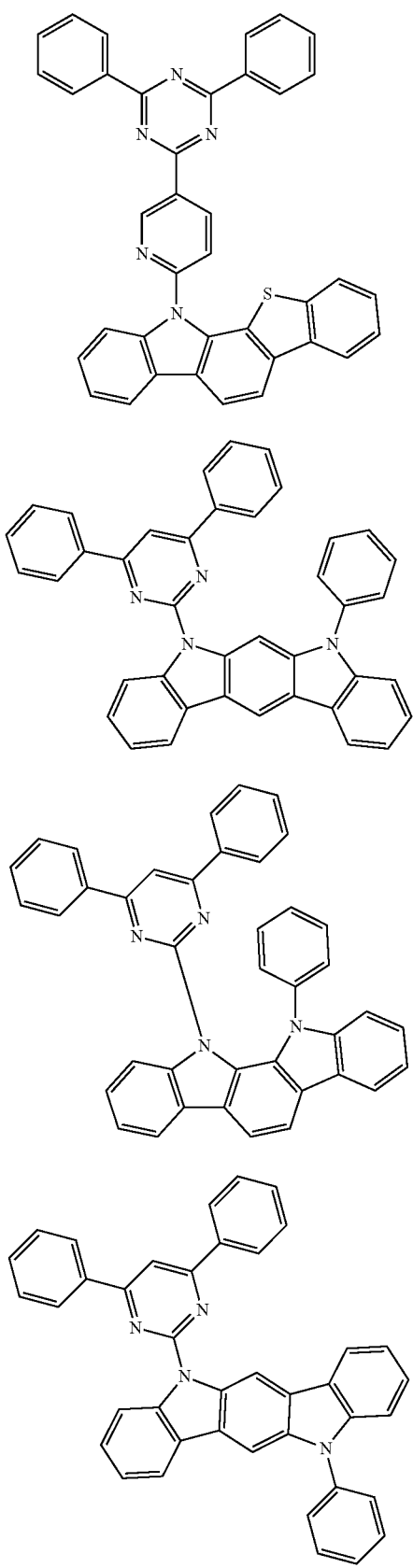
H-73
H-74
H-75
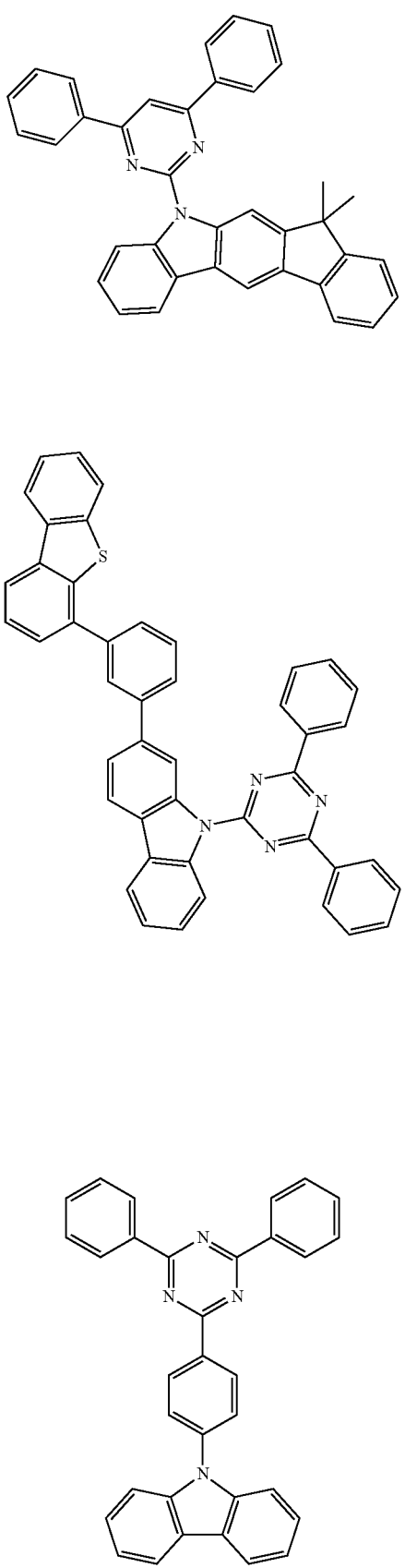

H-76
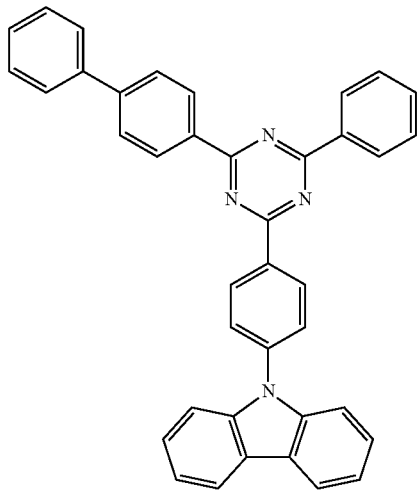
H-77
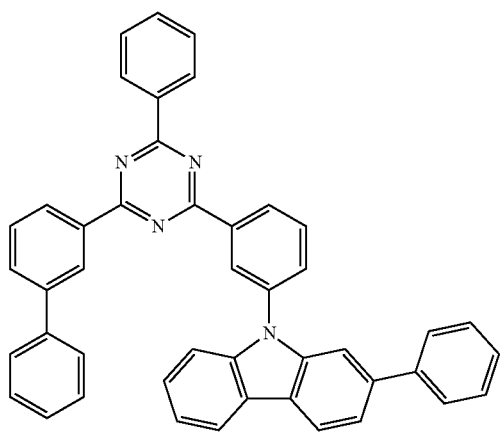
H-78
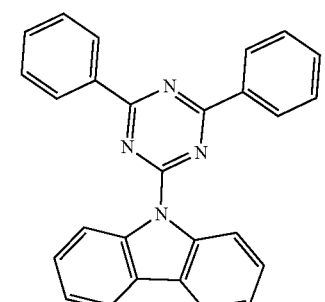
H-79
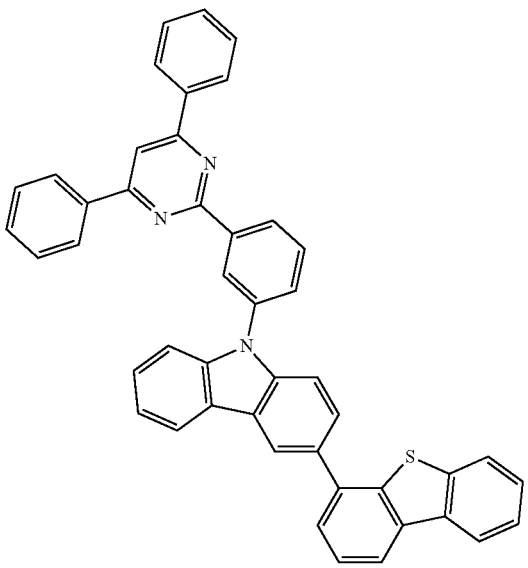
H-80
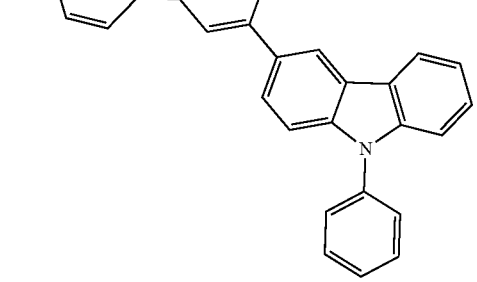

H-81
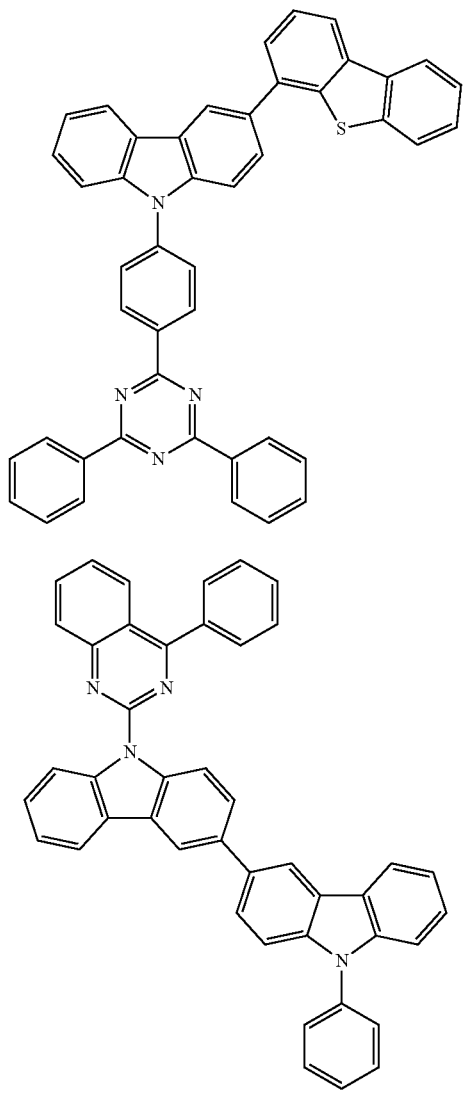
H-84
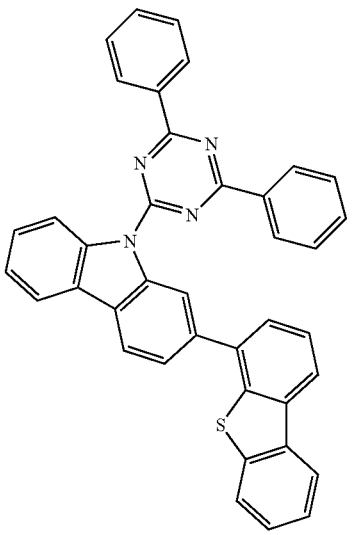
H-82
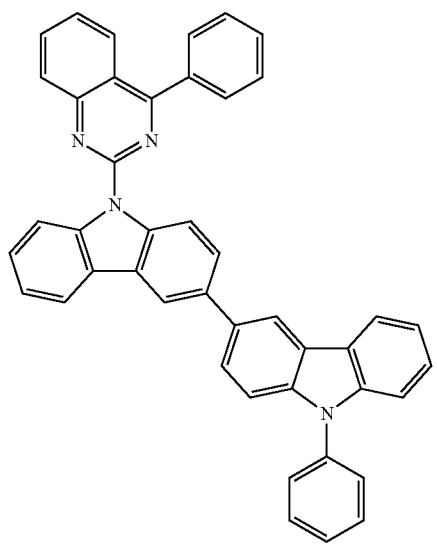
H-85
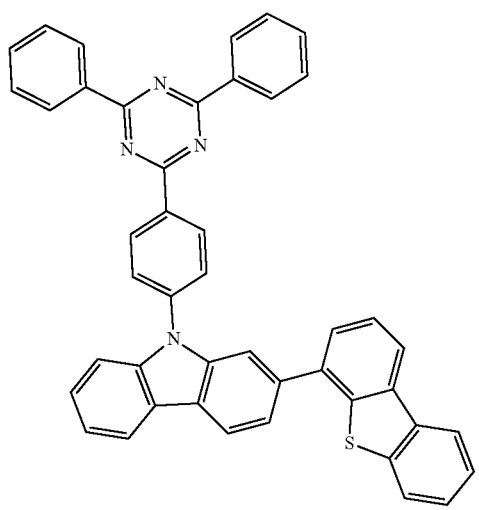
H-83
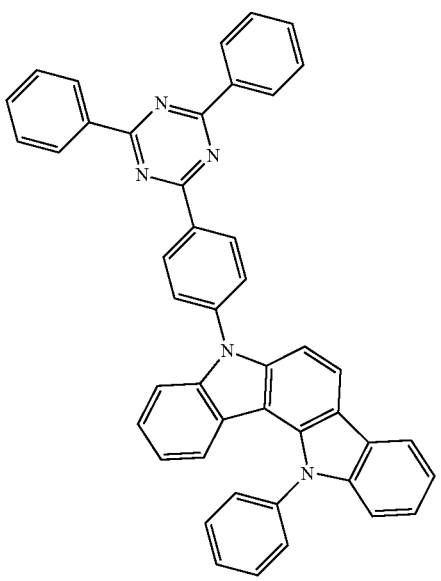
H-86
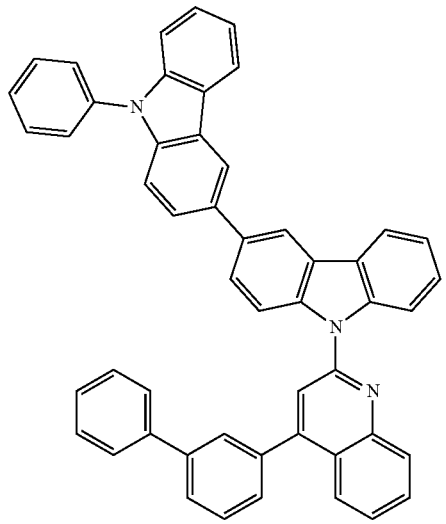

H-87
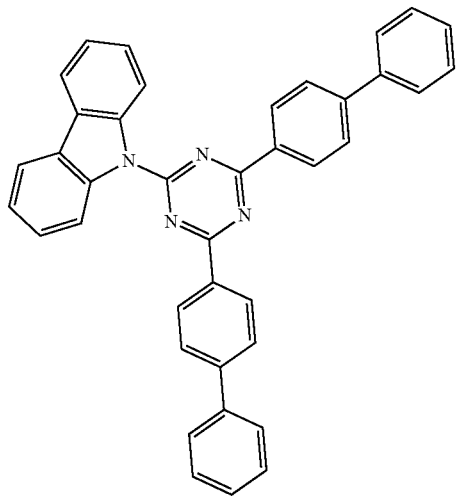
H-88
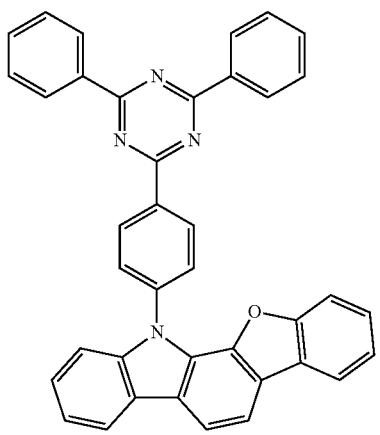
H-89
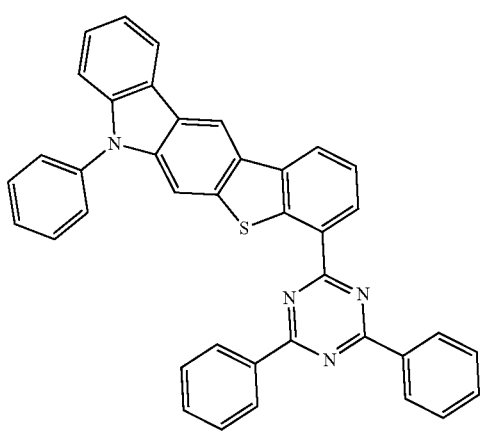
H-90
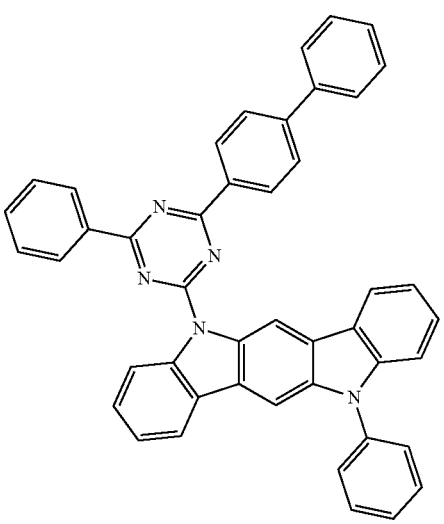
H-91
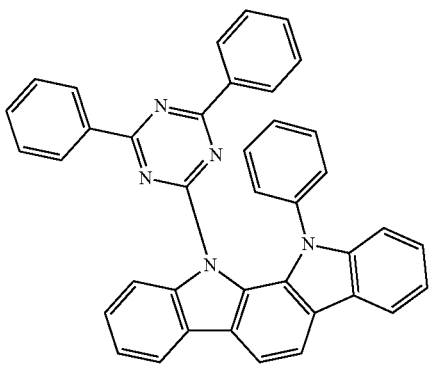
H-92
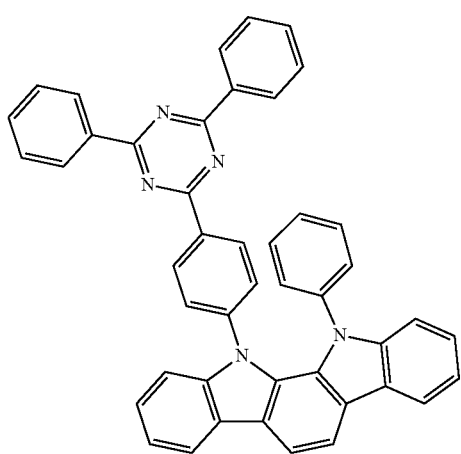

H-93
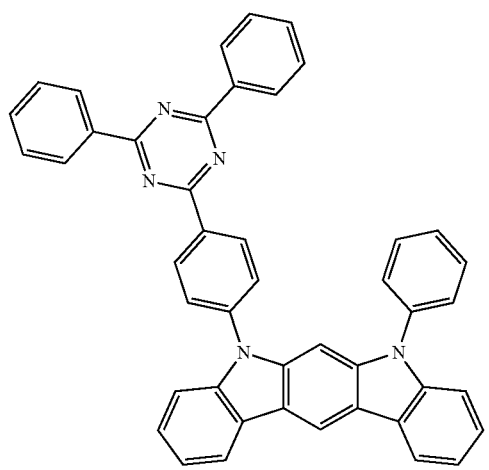
H-94
H-95
H-96
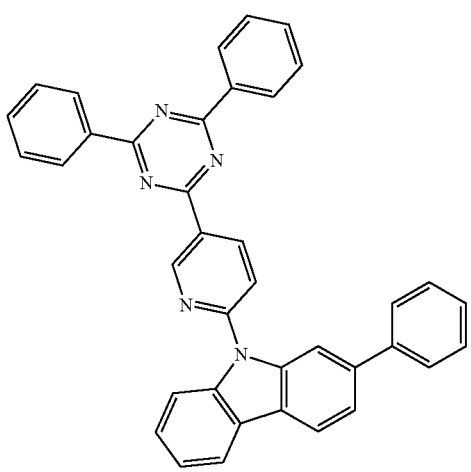
H-97
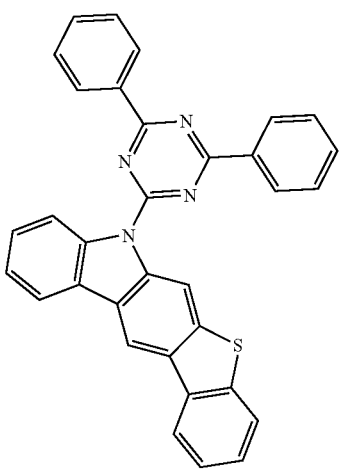
H-98
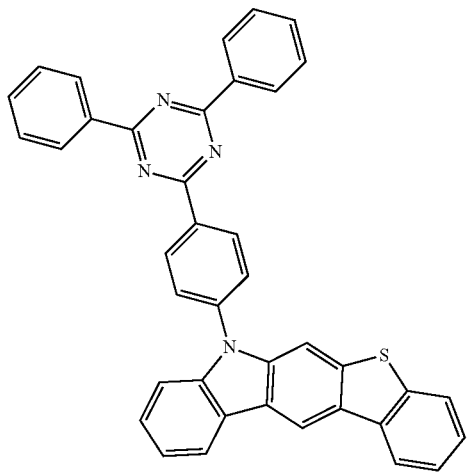

H-99
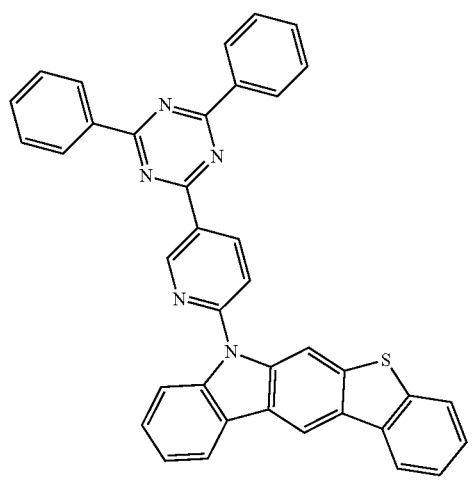
H-100
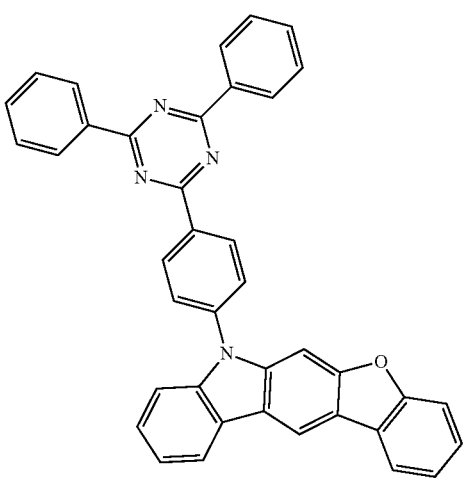
H-101
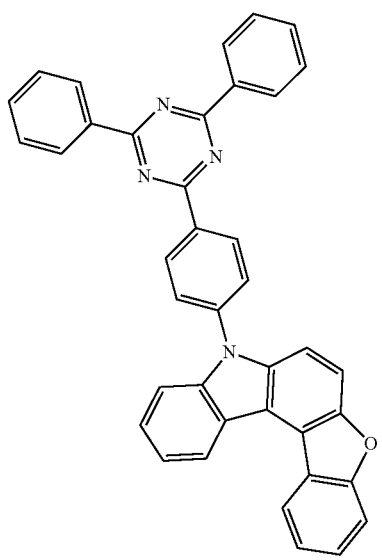
H-102
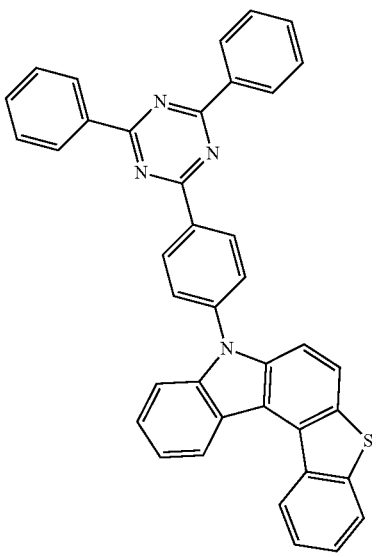
H-103
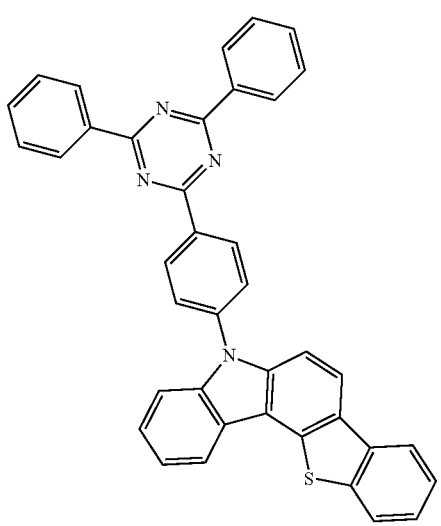
H-104
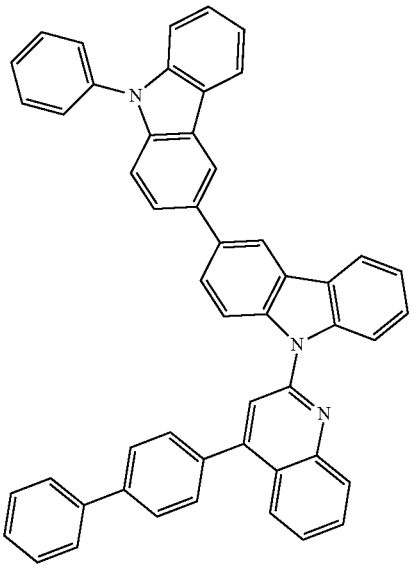

-continued
H-105
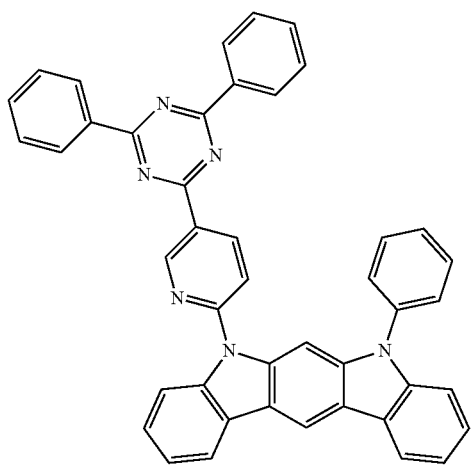
H-106
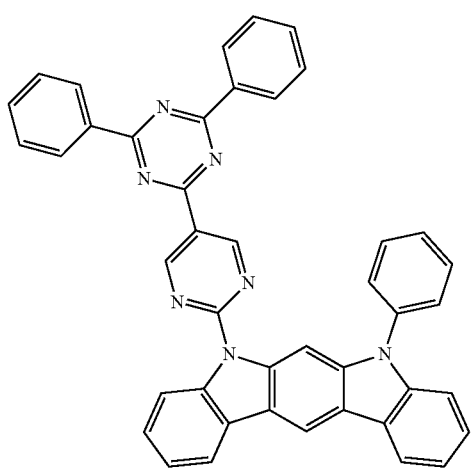
H-107
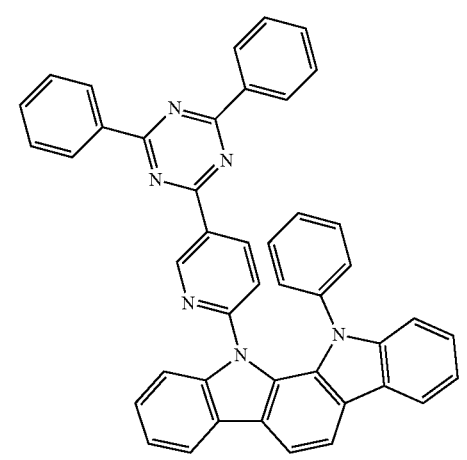
-continued
H-108
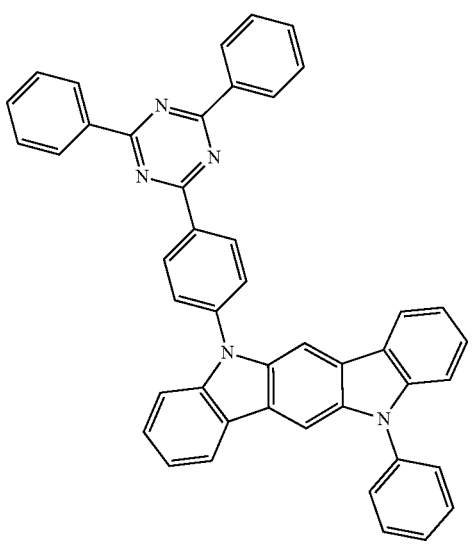
H-109
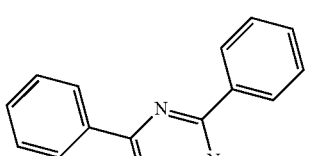
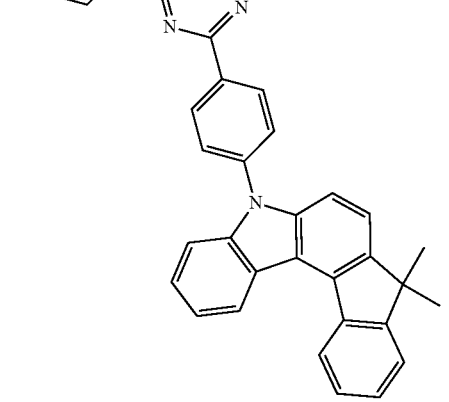
H-110
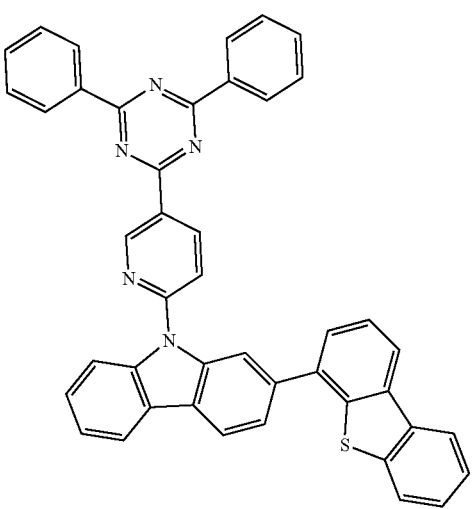

-continued
H-111
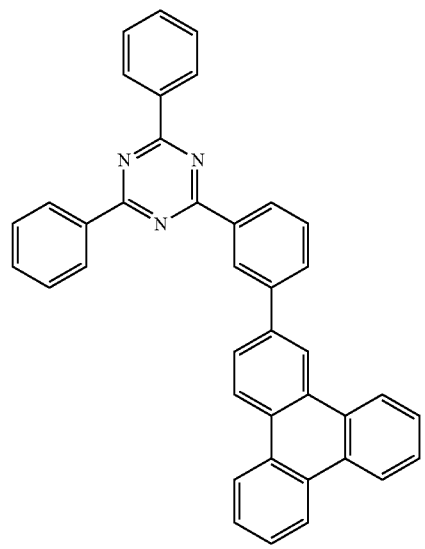
H-113
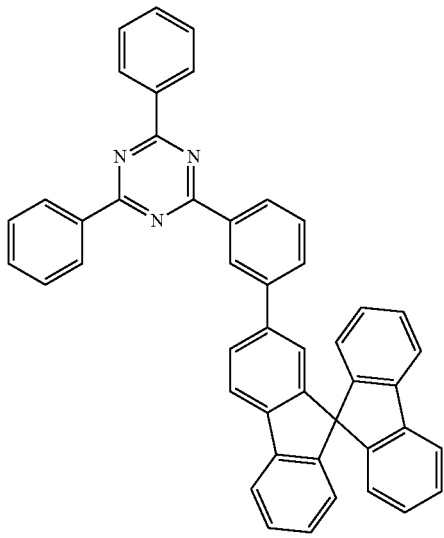
H-114
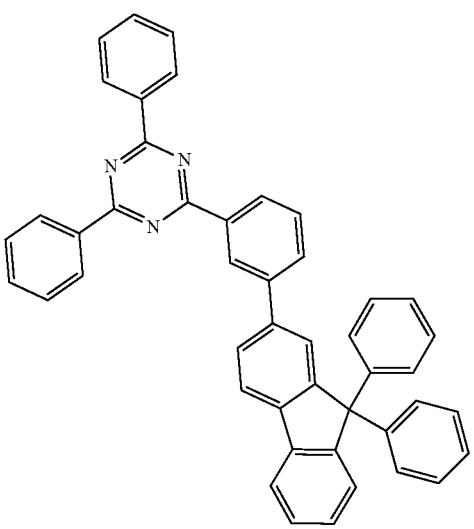
H-112
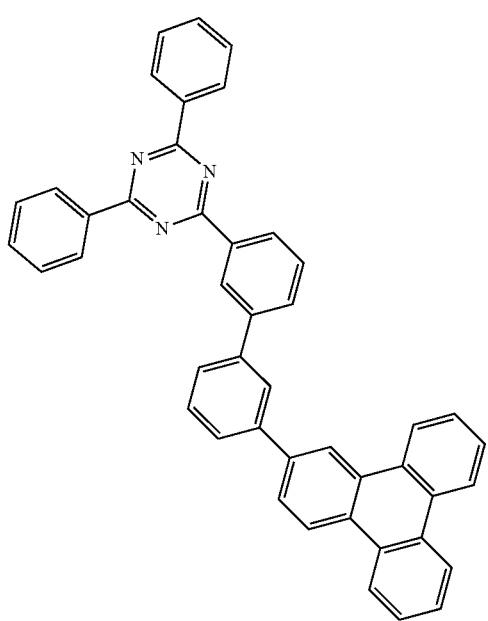
H-115
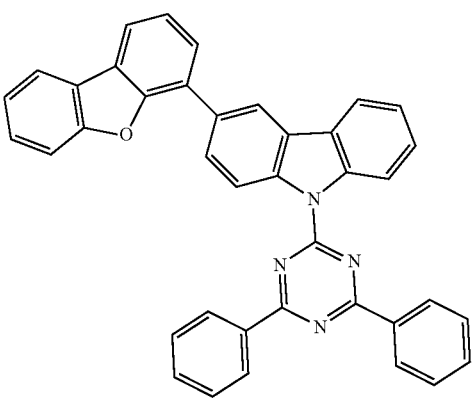

H-116
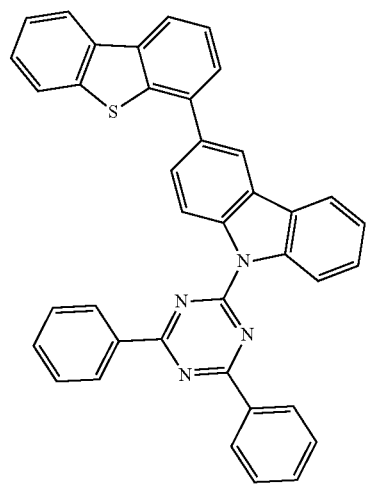
H-117
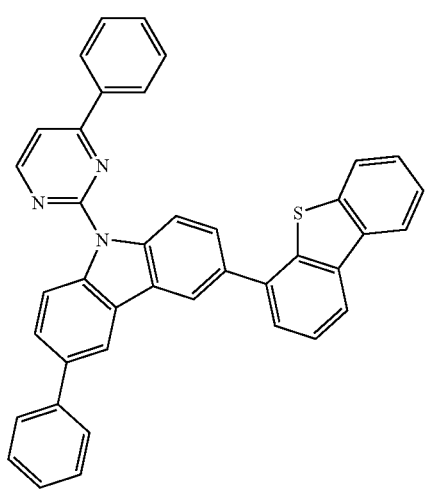
H-118
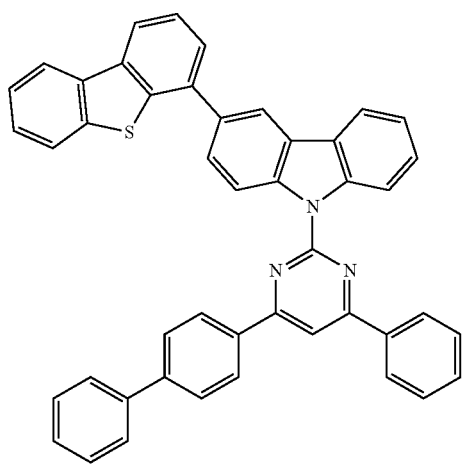
H-119
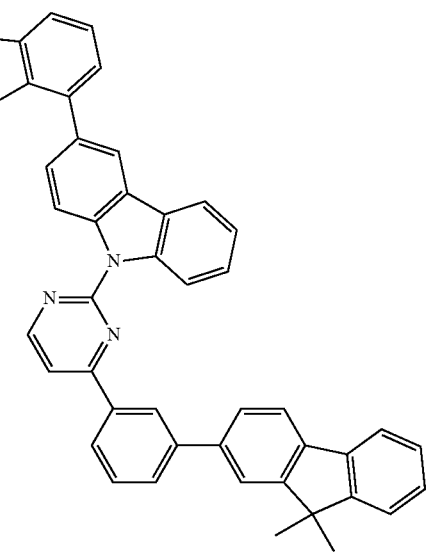
H-120
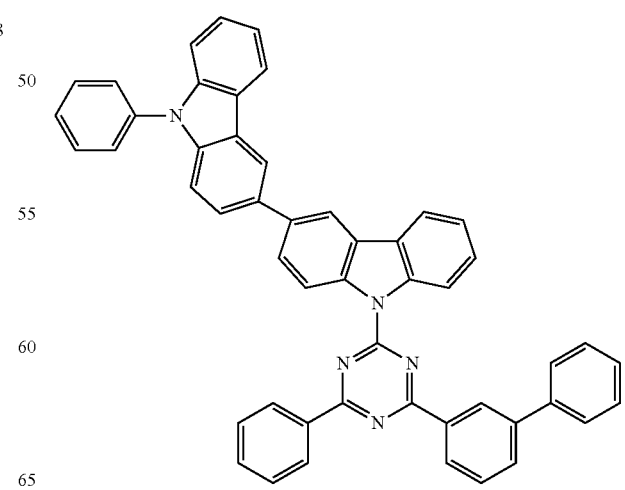

H-121
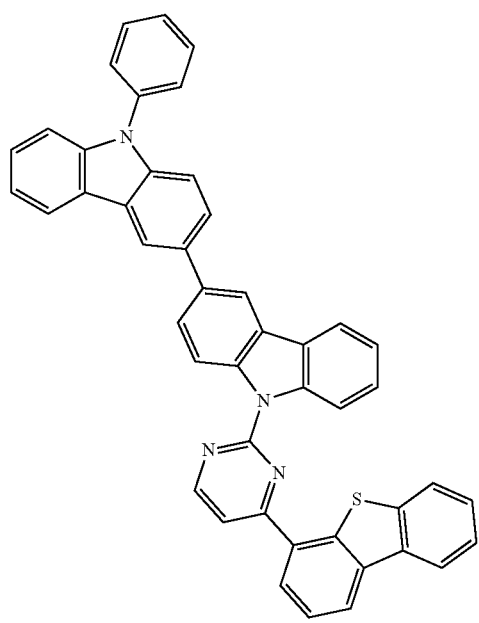
H-123
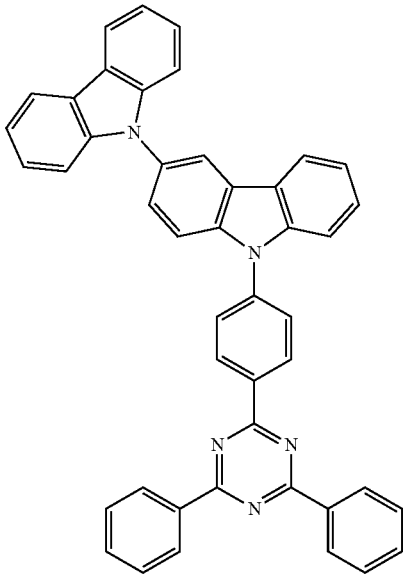
H-122
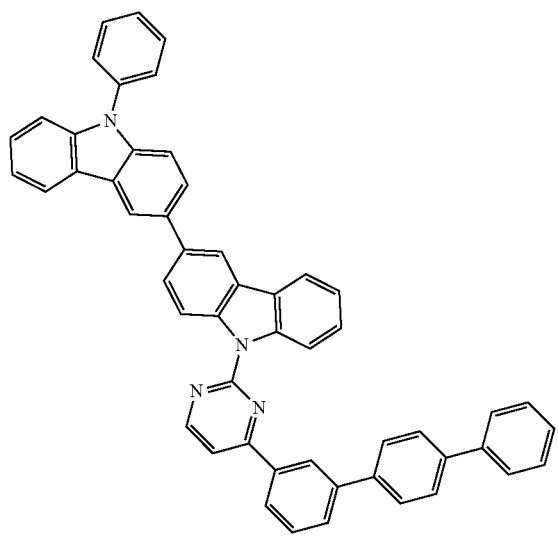
H-124
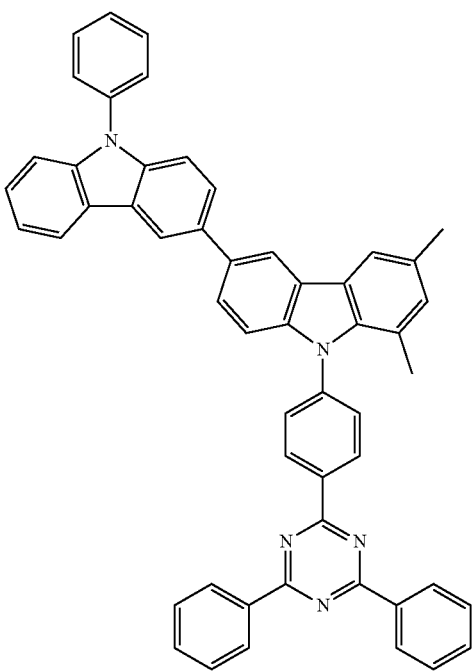

H-125
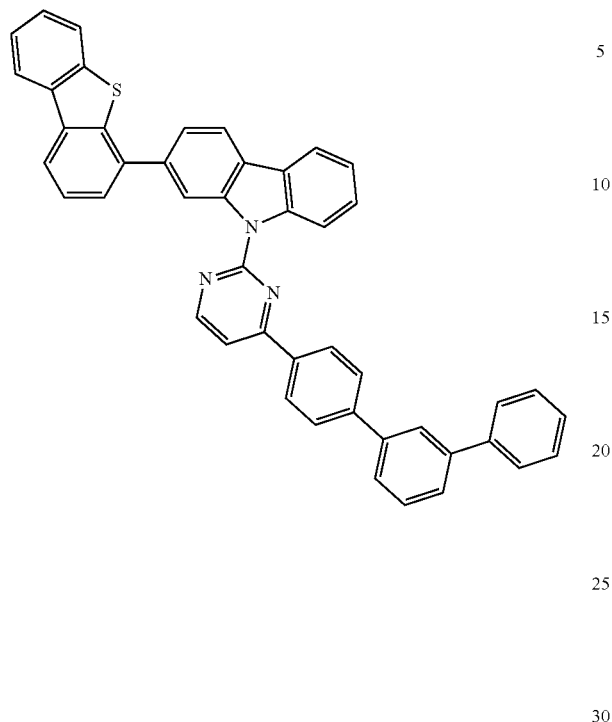
H-127
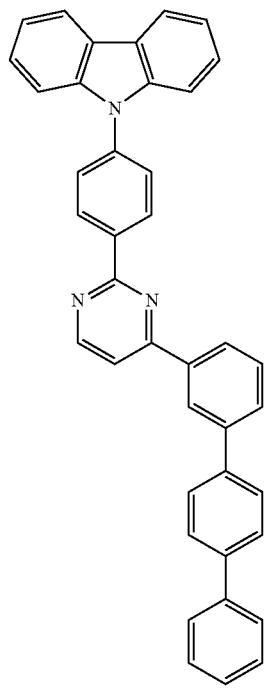
H-126
H-128
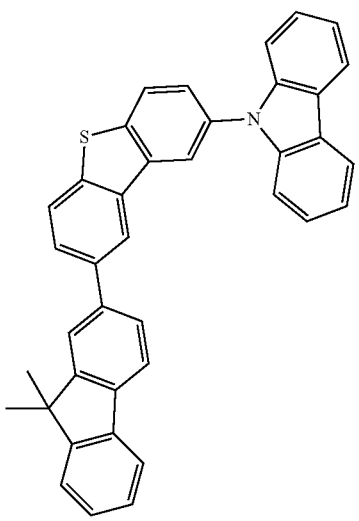

H-129
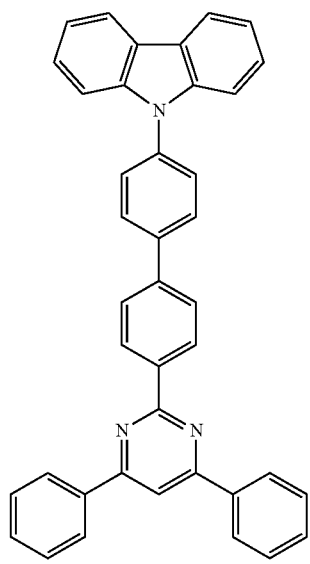
H-131
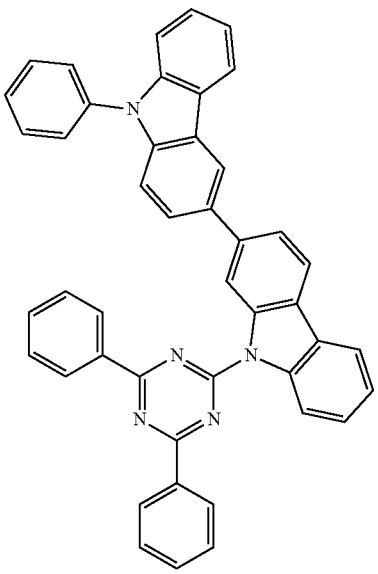
H-130
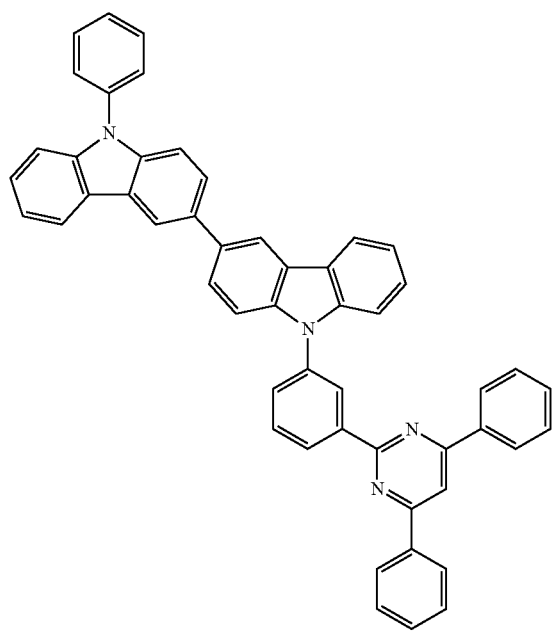
H-132
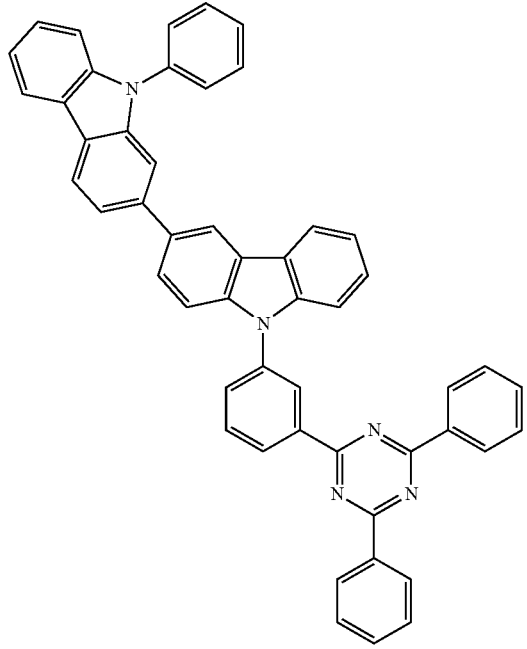

H-133
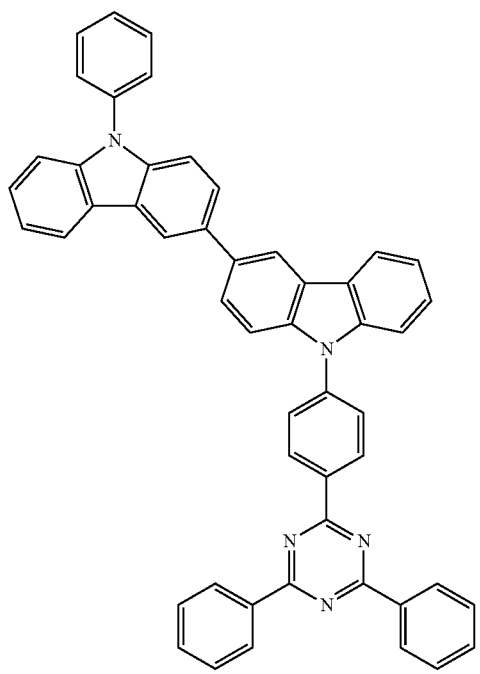
H-135
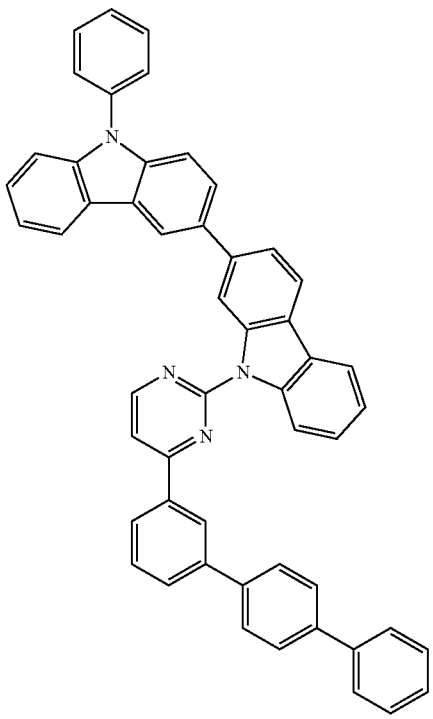
H-134
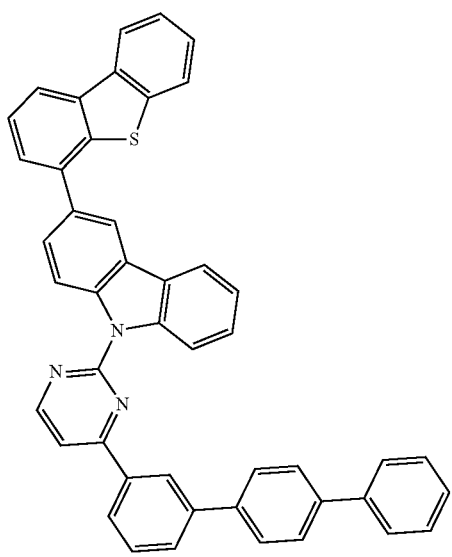
H-136
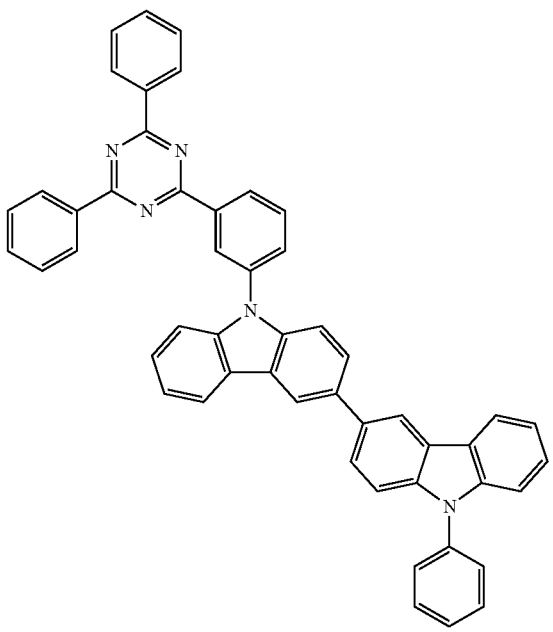

H-137
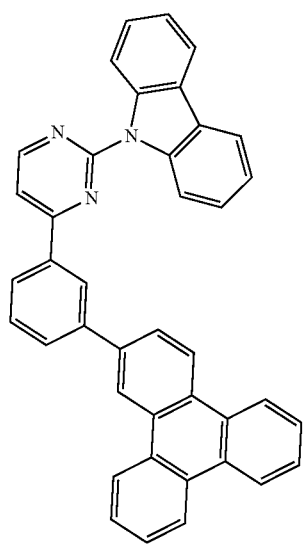
H-138
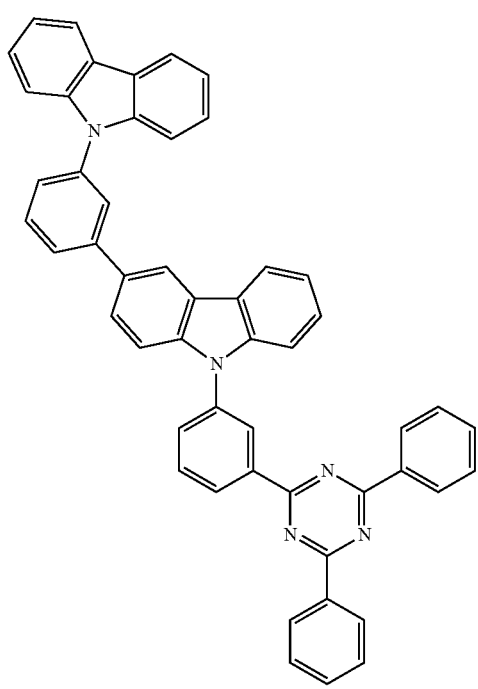
H-139
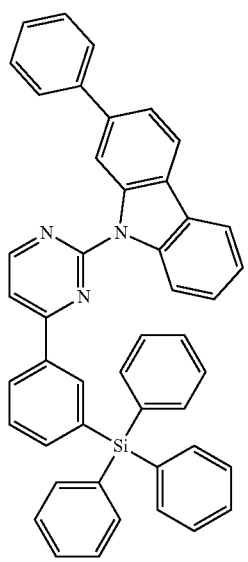
H-140
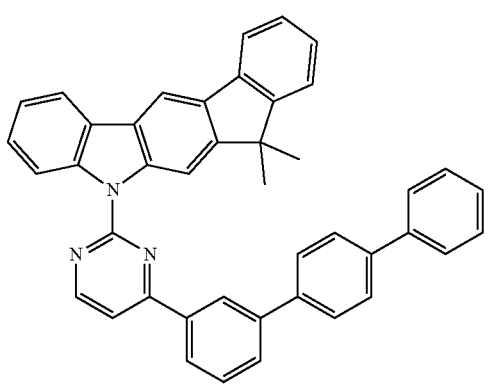
H-141

-continued
H-142
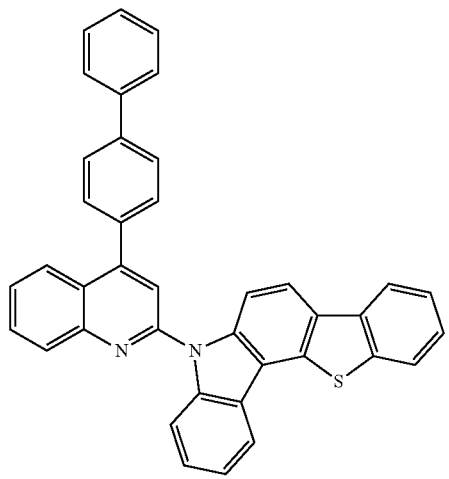
H-143
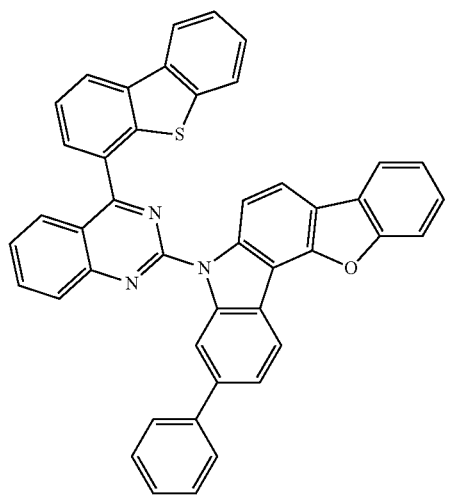
H-144
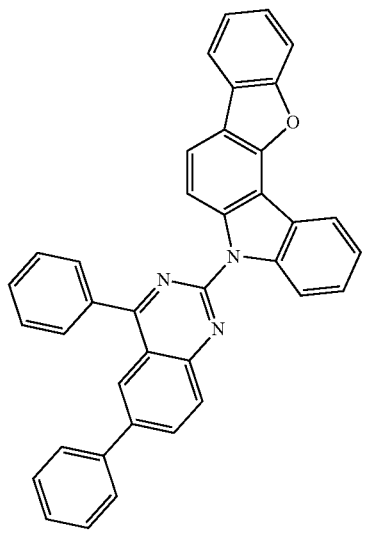
H-145
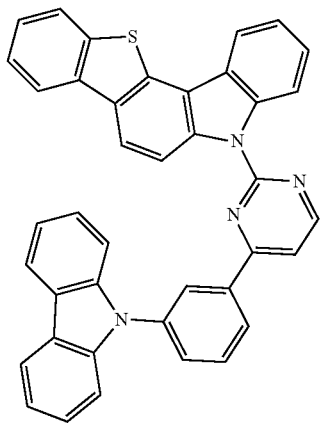
H-146
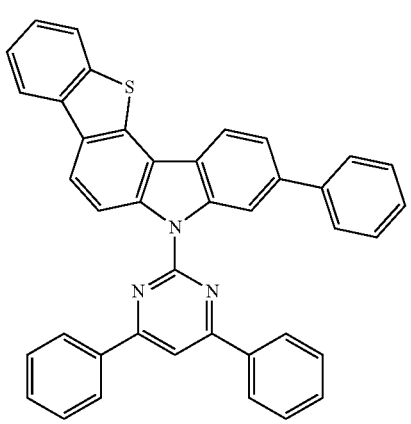
H-147
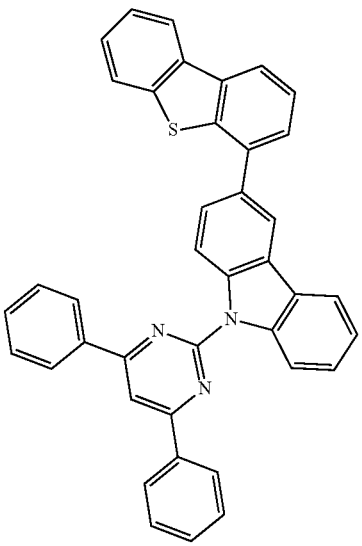

-continued
H-148
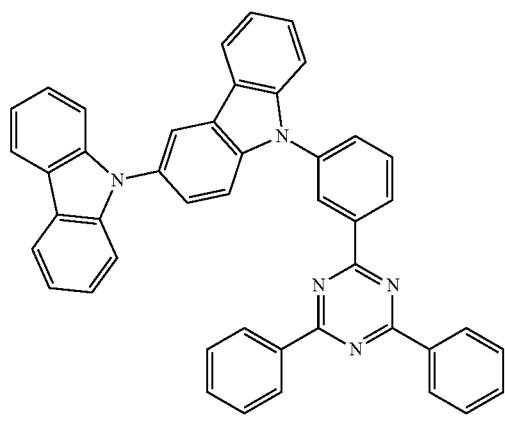
H-149
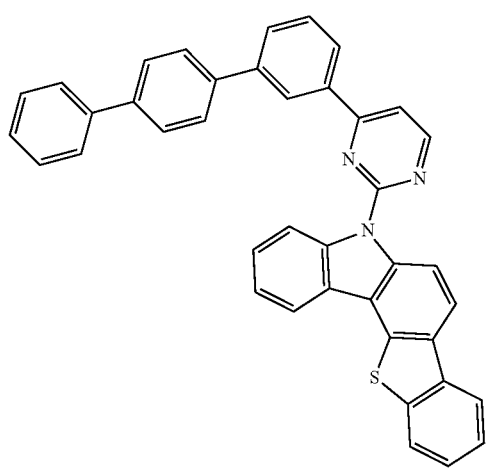
H-150
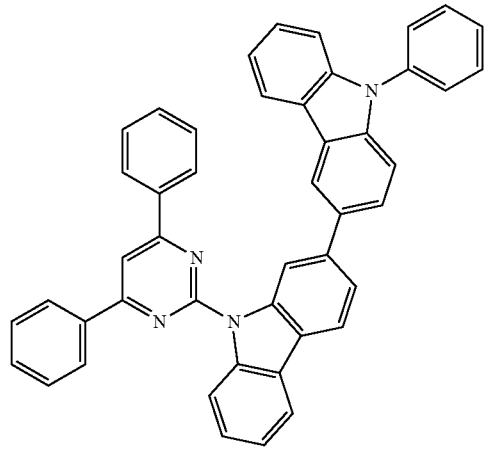
-continued
H-151
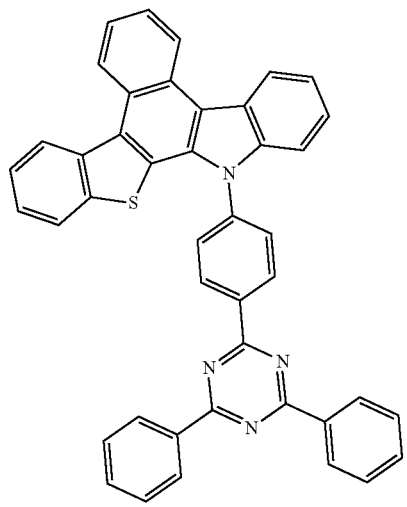
H-152
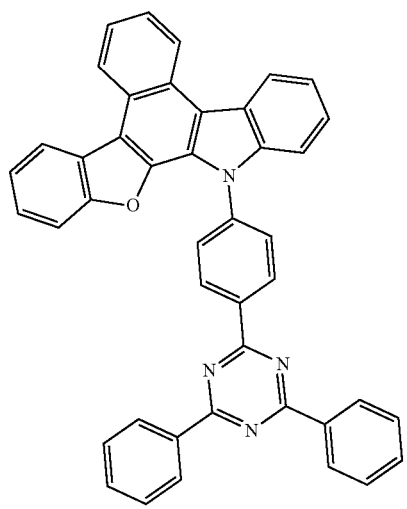
H-153
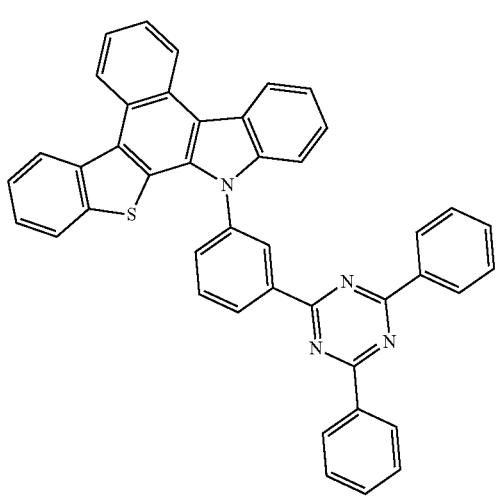

H-154
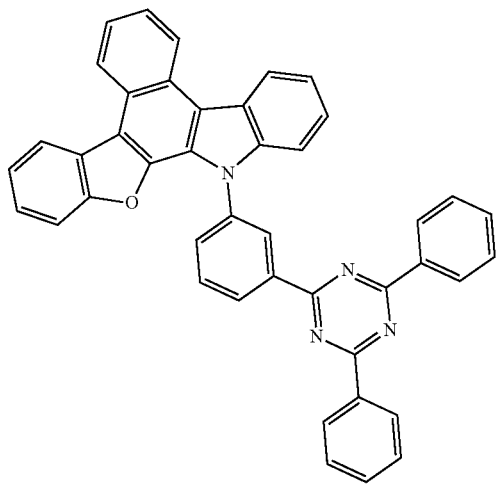
H-155
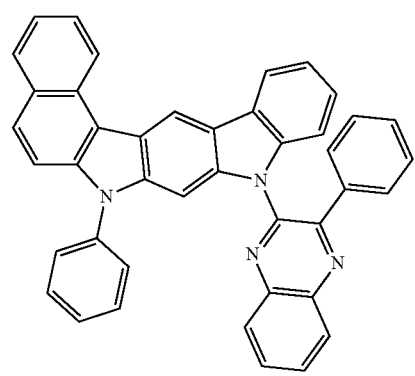
H-156
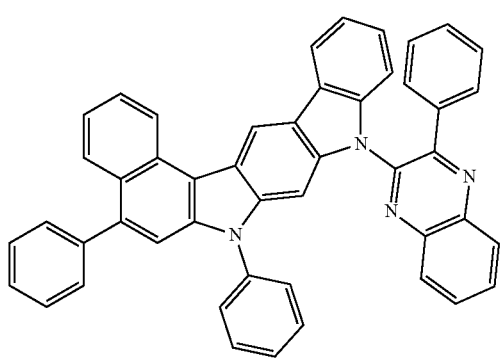
H-157
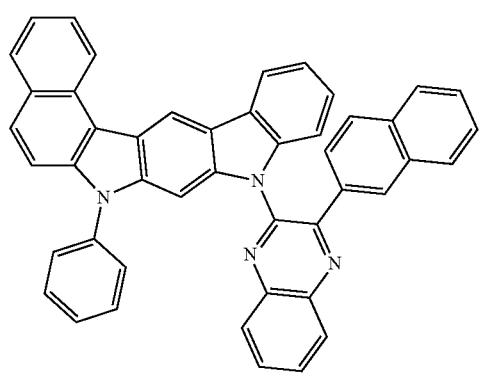
H-158
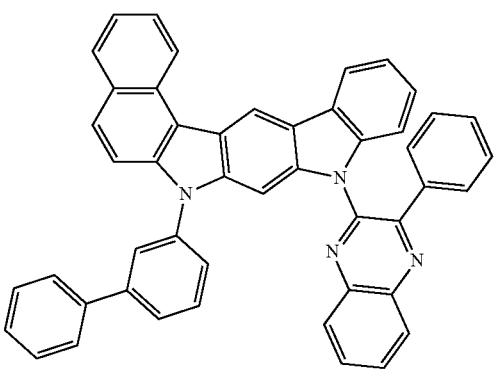
H-159
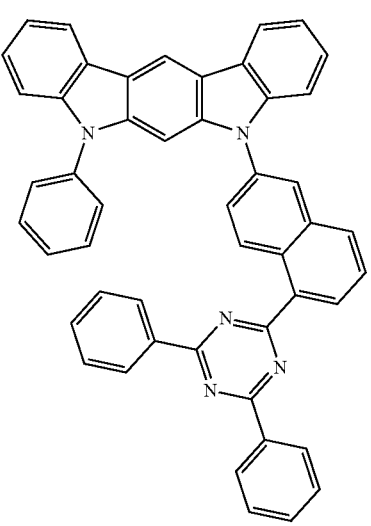
H-160
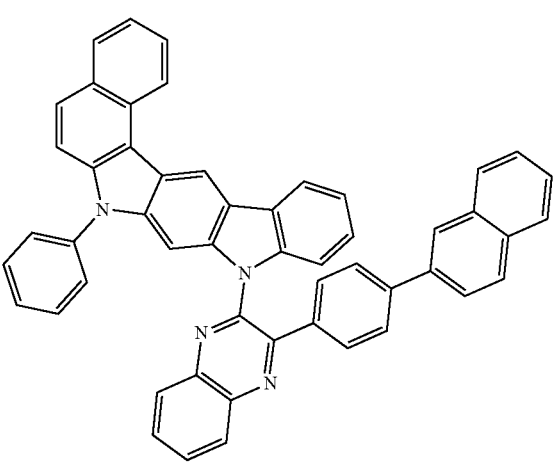

H-161
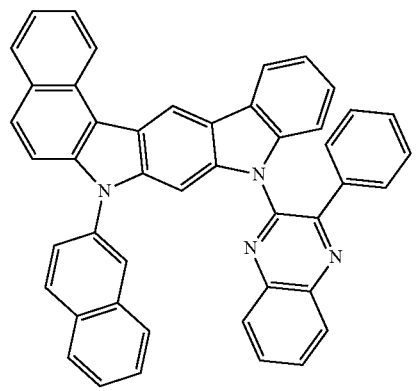
H-162
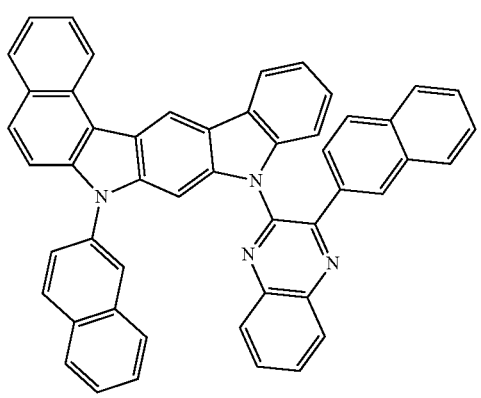
H-163
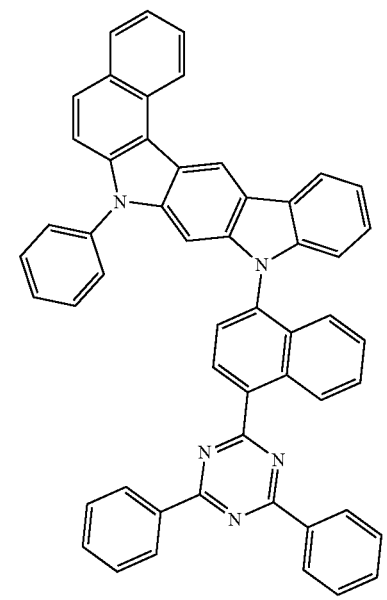
H-164
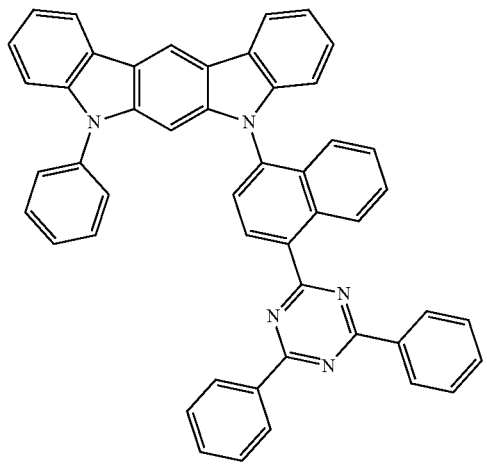
H-165
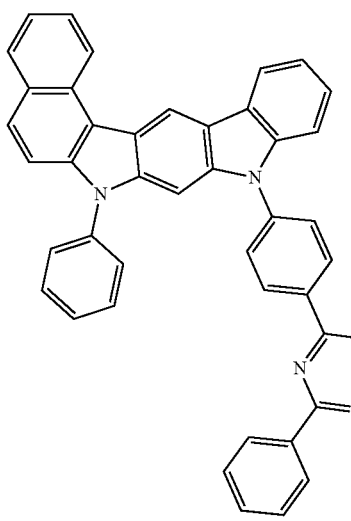
H-166
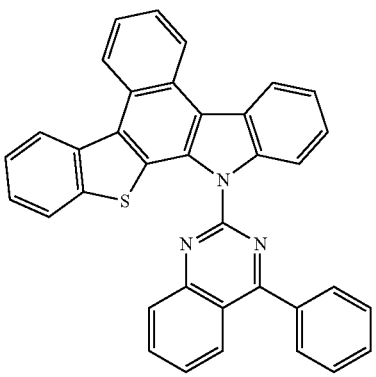

H-167
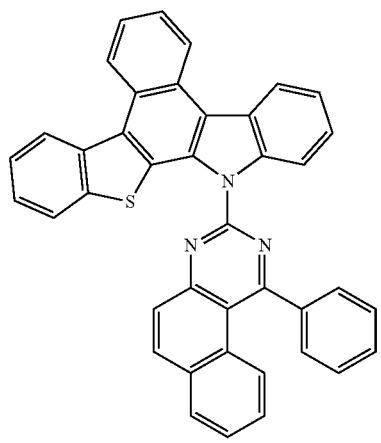
H-168
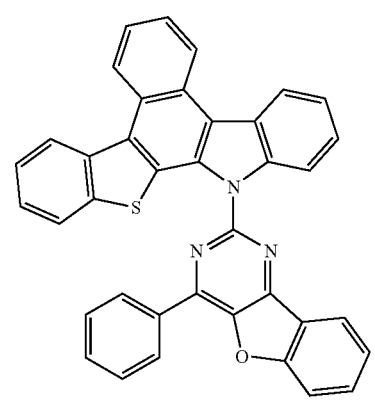
H-169
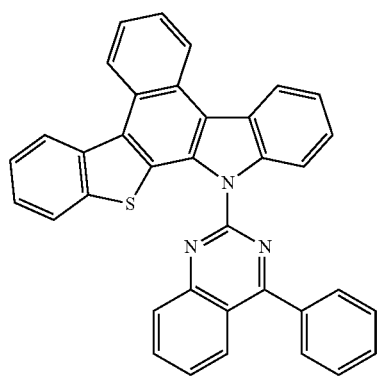
H-170
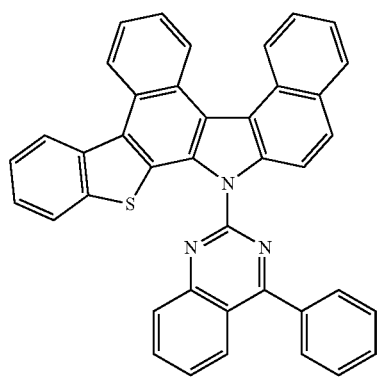
H-171
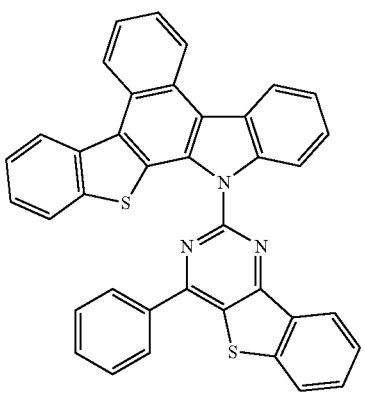
H-172
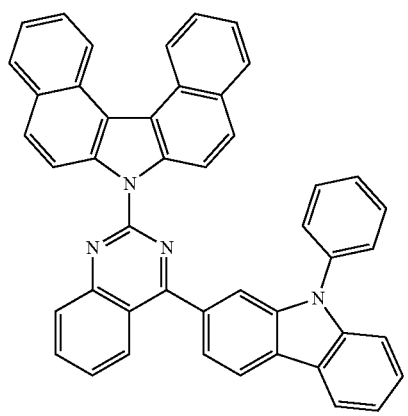
H-173
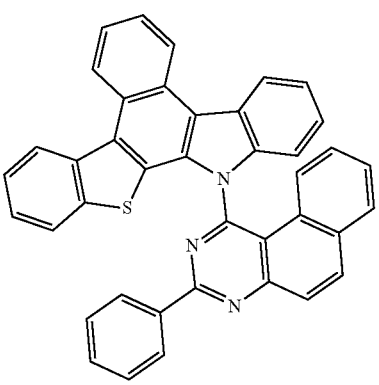
H-174
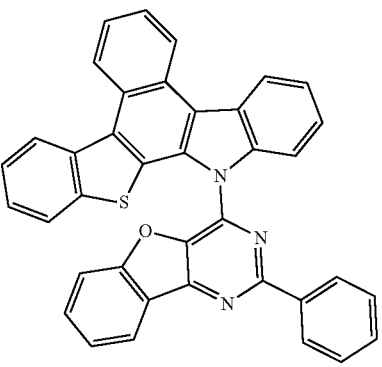

H-175
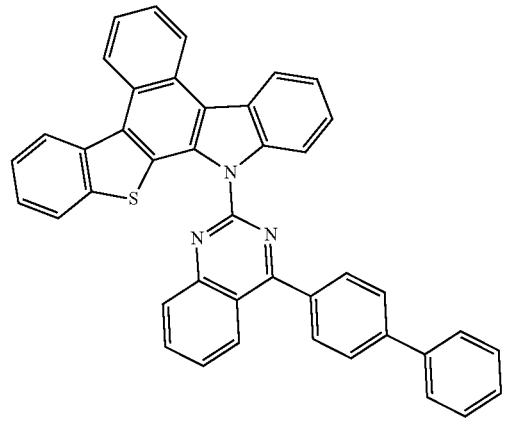
H-176
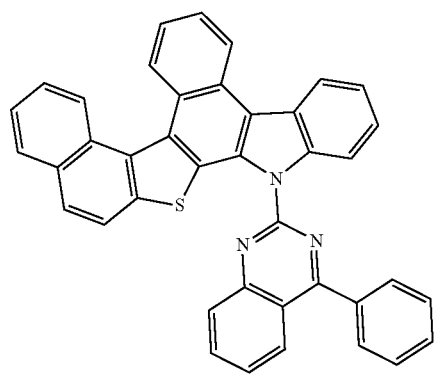
H-177
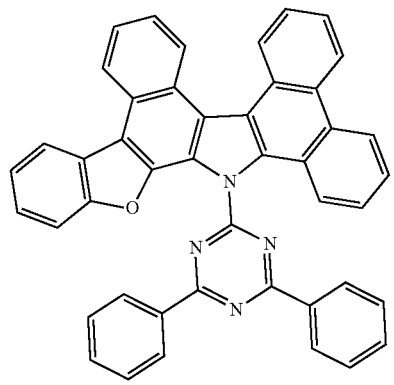
H-178
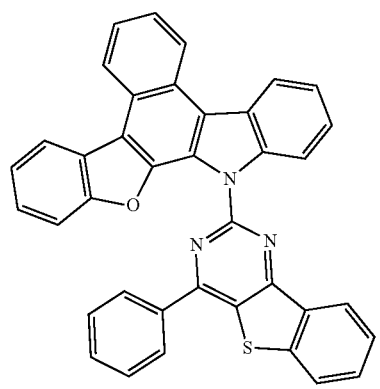
H-179
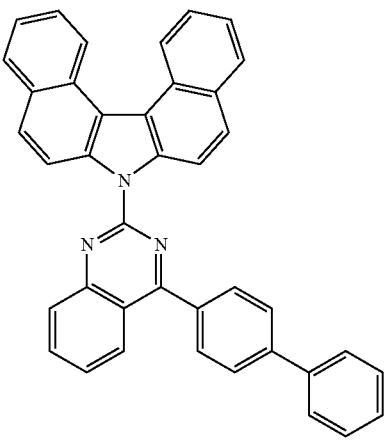
H-180
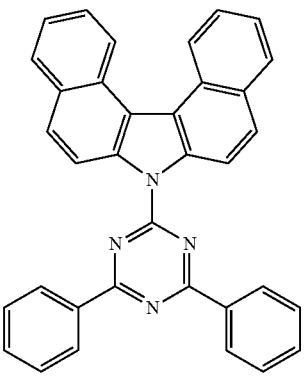
H-181
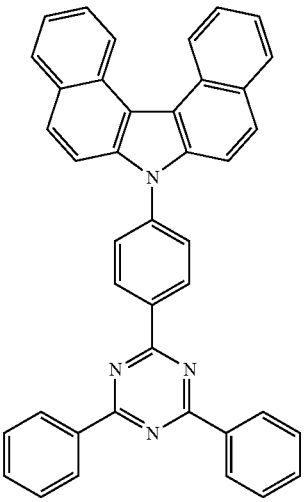

-continued
H-182
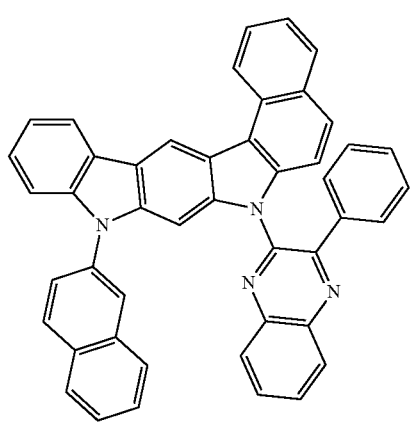
H-183
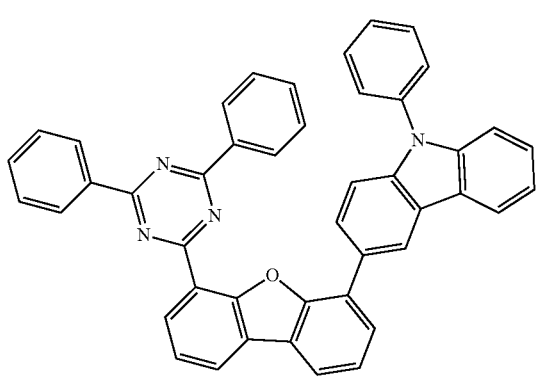
H-184
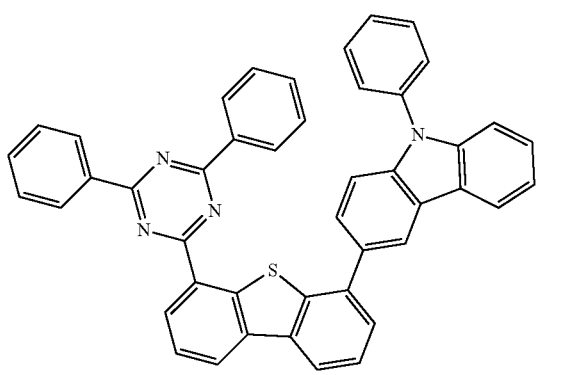
-continued
H-185
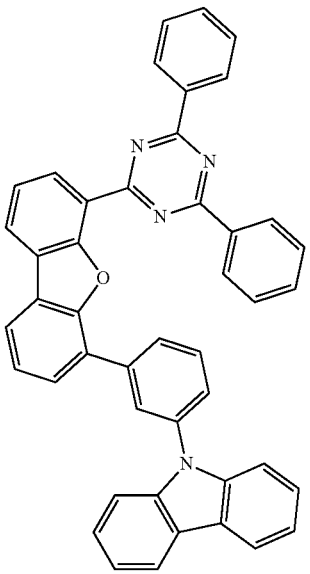
H-186
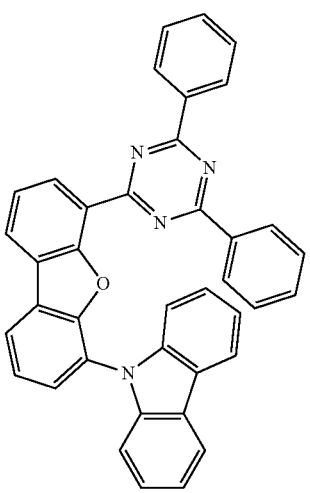

H-187
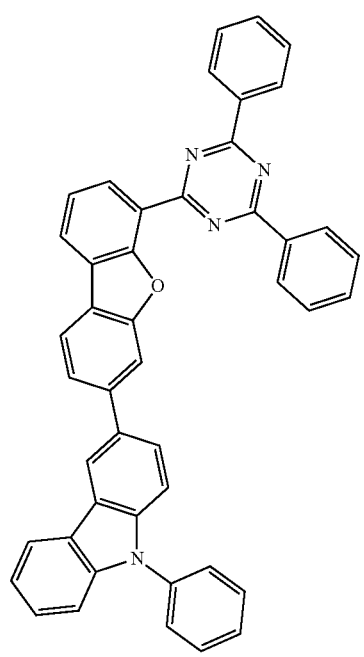
H-188
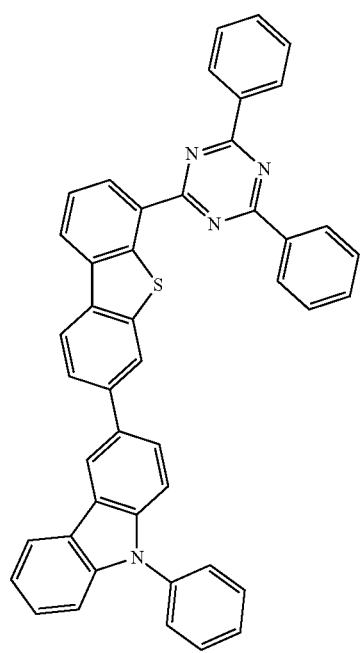
H-189
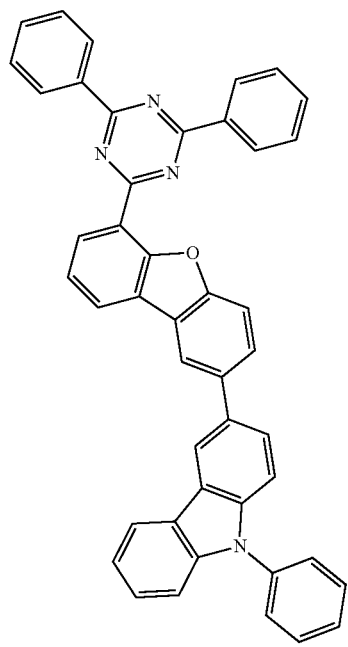
H-190
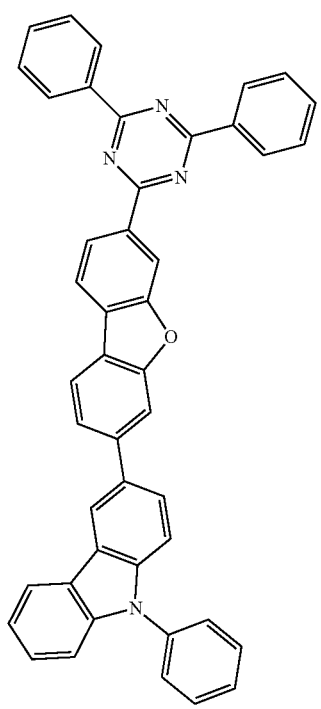

H-191
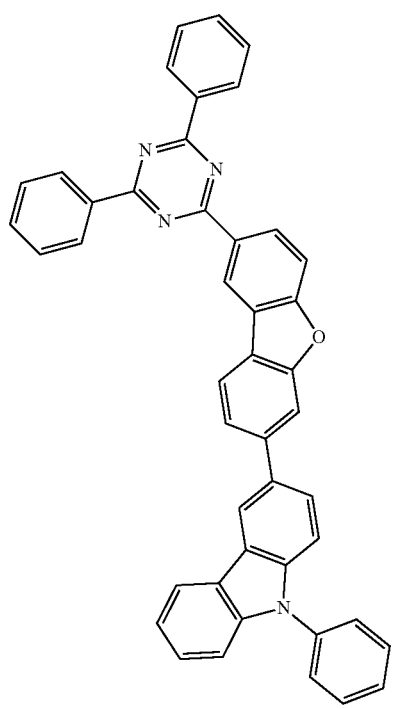
H-192
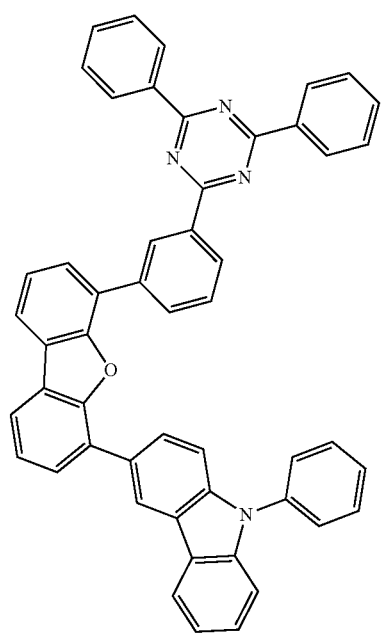
H-193
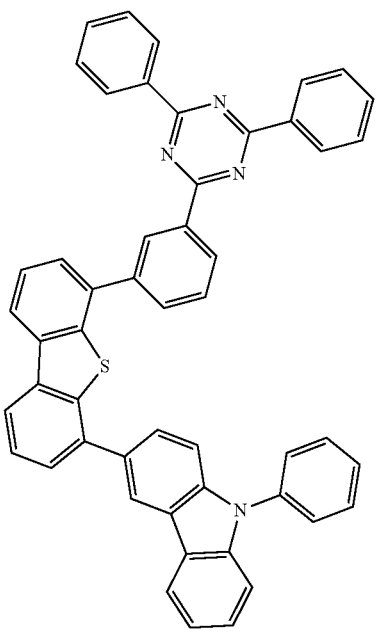
H-194
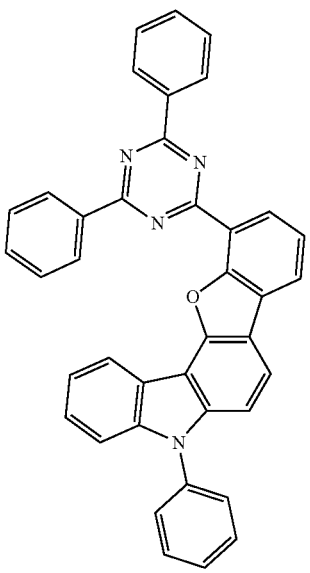

-continued
H-195
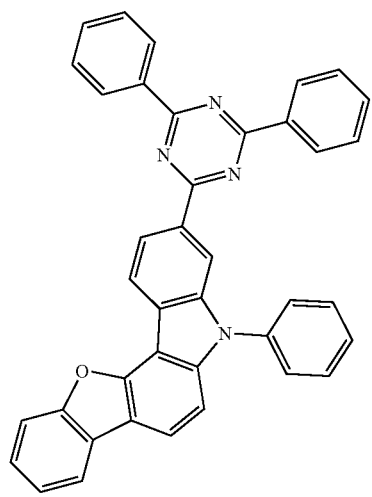
H-197
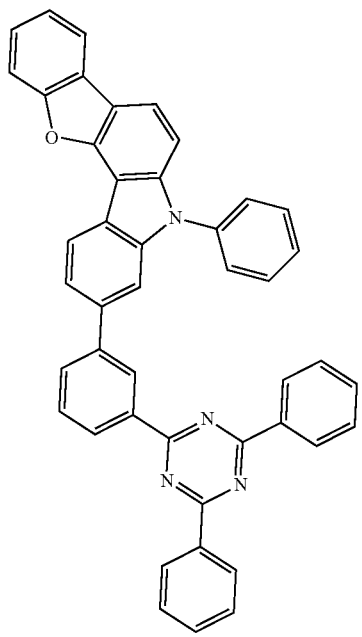
H-196
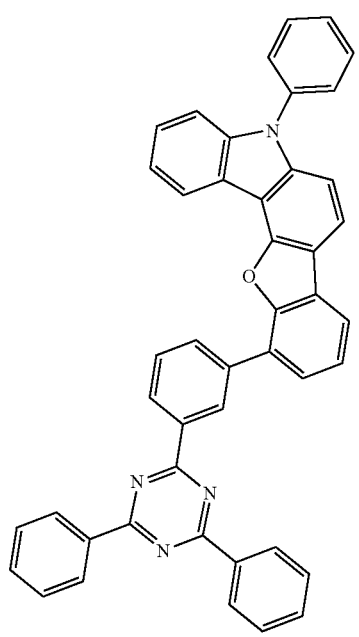
H-198
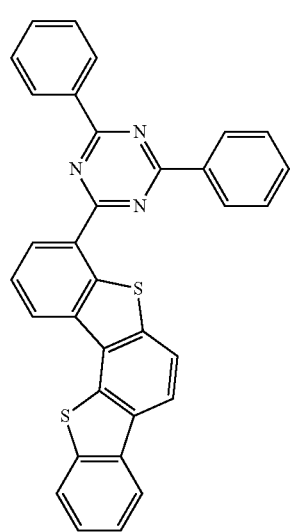

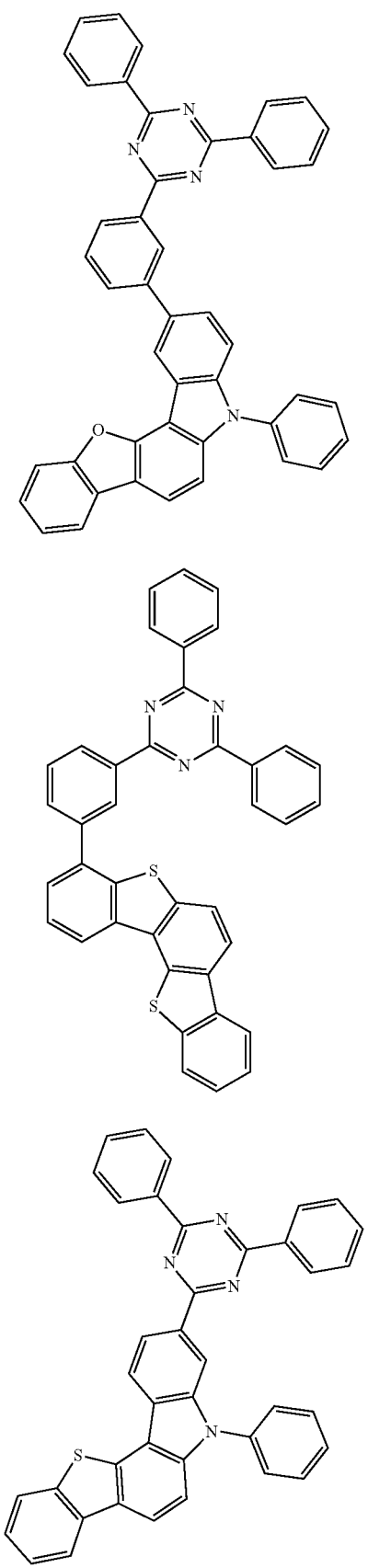
H-199
H-200
H-201
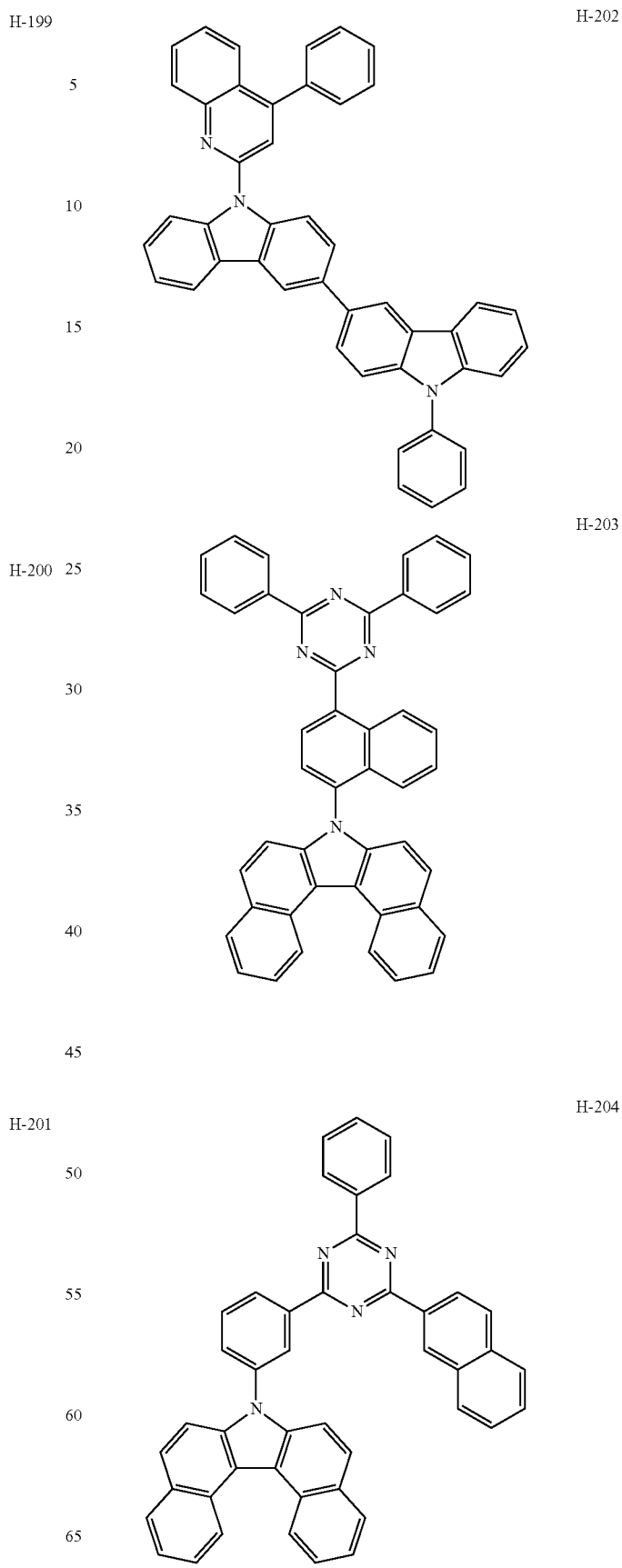
H-202
H-203
H-204

-continued
H-205
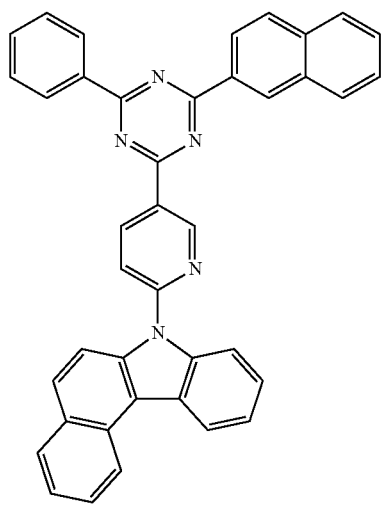
H-208
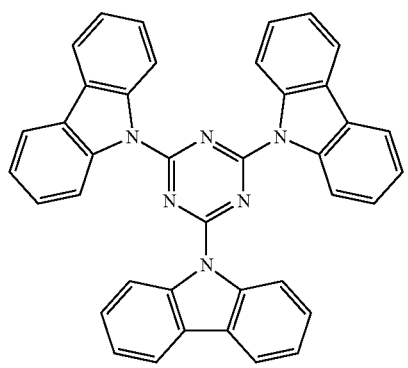
H-206
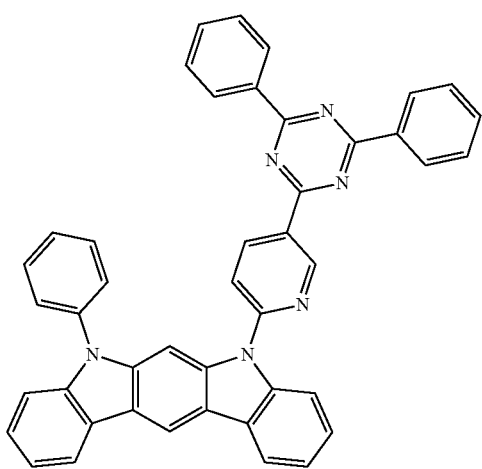
H-209
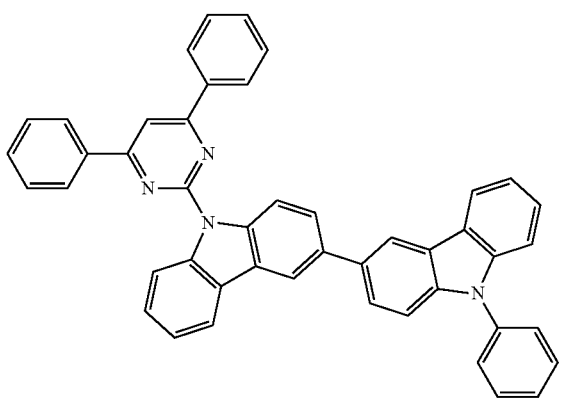
H-207
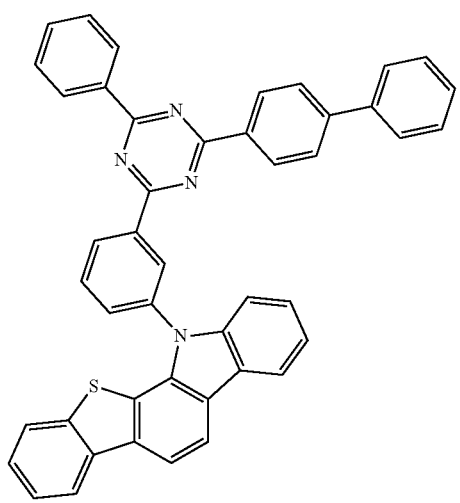
H-210
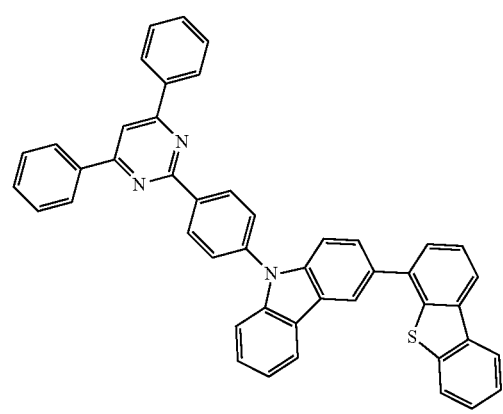
and

H-211

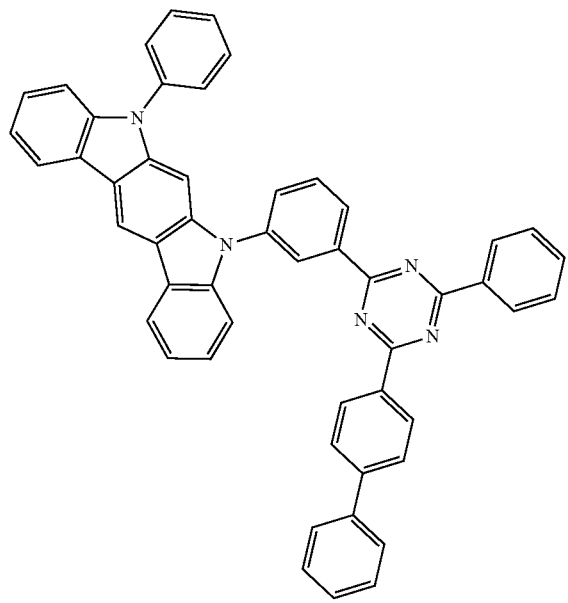

wherein TPS represents a triphenylsilyl group.

As for the dopant comprised in the organic electroluminescent device according to the present disclosure, at least one phosphorescent or fluorescent dopant may be used, and at least one phosphorescent dopant is preferable. The phosphorescent dopant materials applied to the organic electroluminescent device according to the present disclosure are not particularly limited, but may be selected from metallated complex compounds of iridium (Ir), osmium (Os), copper (Cu), and platinum (Pt), may be preferably selected from ortho-metallated complex compounds of iridium (Ir), osmium (Os), copper (Cu), and platinum (Pt), and may be more preferably an ortho-metallated iridium complex compound.

The dopant comprised in the organic electroluminescent device of the present disclosure includes the compound represented by the following formula 101, but is not limited thereto:

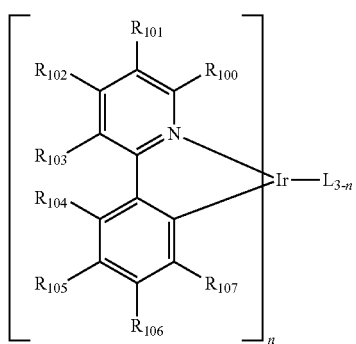

(101)

wherein
L is selected from the following structures:

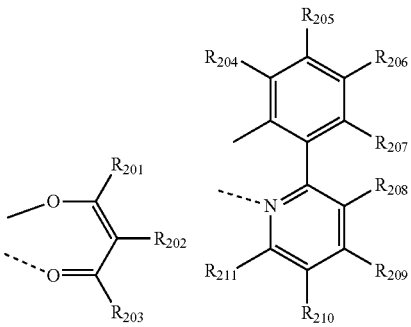

$R_{100}$ to $R_{103}$ each independently represent hydrogen, deuterium, a halogen, a (C1-C30)alkyl unsubstituted or substituted with a halogen(s), a substituted or unsubstituted (C3-C30)cycloalkyl, a substituted or unsubstituted (C6-C30)aryl, a cyano, a substituted or unsubstituted (3- to 30-membered) heteroaryl, or a substituted or unsubstituted (C1-C30) alkoxy; or $R_{100}$ to $R_{103}$ may be linked to adjacent $R_{100}$ to $R_{103}$ to form a substituted or unsubstituted fused ring, e.g., a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline;

$R_{104}$ to $R_{107}$ each independently represent hydrogen, deuterium, a halogen, a (C1-C30)alkyl unsubstituted or substituted with a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30) alkoxy; or $R_{104}$ to $R_{107}$ may be linked to adjacent $R_{104}$ to $R_{107}$ to form a substituted or unsubstituted fused ring, e.g., a substituted or unsubstituted naphthalene, a substituted or unsubstituted fluorene, a substituted or unsubstituted dibenzothiopene, a substituted or unsubstituted dibenzofuran, a substituted or unsubstituted indenopyridine, a substituted or unsubstituted benzofuropyridine, or a substituted or unsubstituted benzothienopyridine;

$R_{201}$ to $R_{211}$ each independently represent hydrogen, deuterium, a halogen, a (C1-C30)alkyl unsubstituted or substituted with a halogen(s), a substituted or unsubstituted (C3-C30)cycloalkyl, or a substituted or unsubstituted (C6-C30) aryl; may be linked to an adjacent substituent to form a substituted or unsubstituted fused ring; and n represents an integer of 1 to 3.

Specifically, the dopant compound includes the following compounds, but is not limited thereto:

D-1
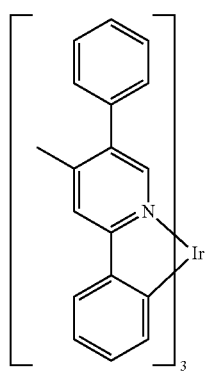
D-2
D-3
D-4
D-5
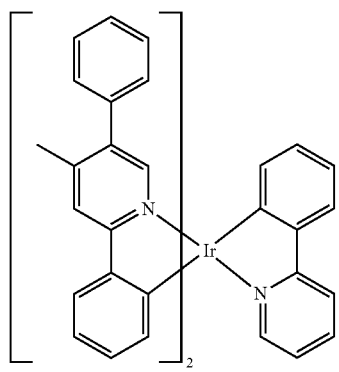
D-6
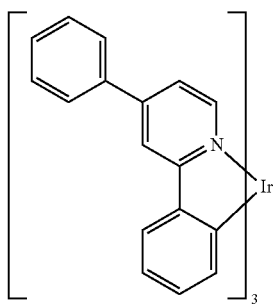
D-7
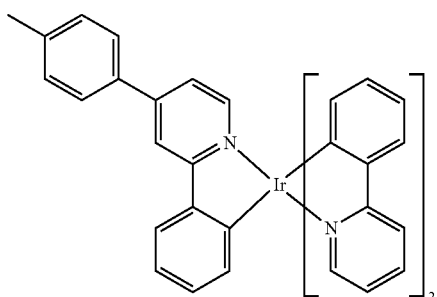
D-8
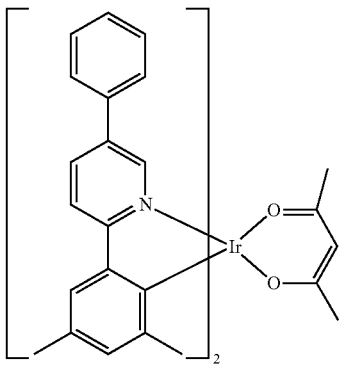

D-9
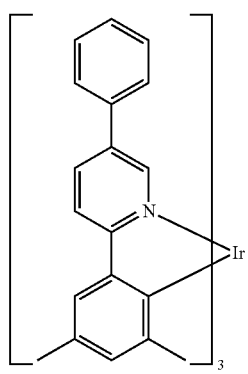
D-10
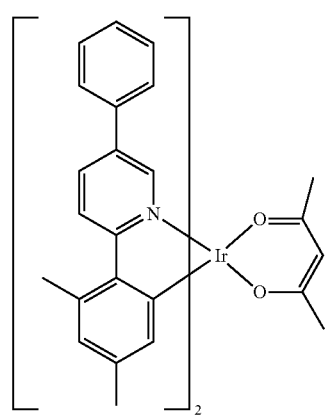
D-11
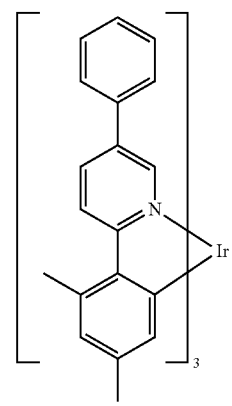
D-12
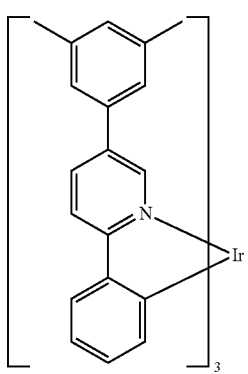
D-13
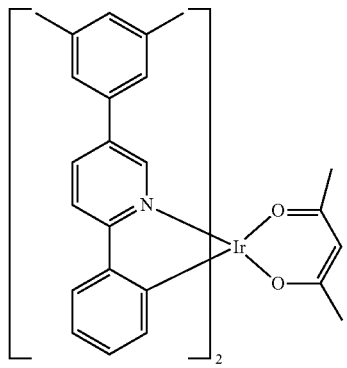
D-14
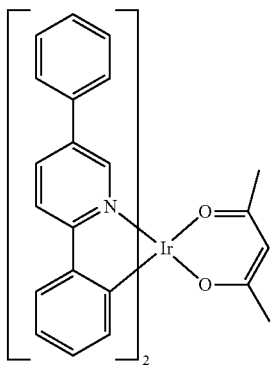
D-15
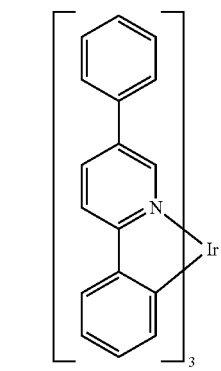
D-16
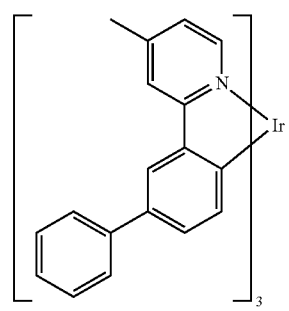

D-17
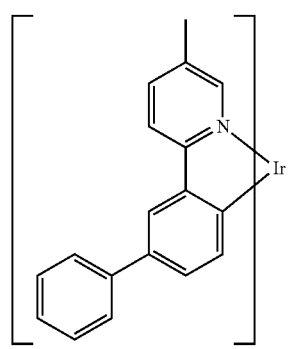
D-18
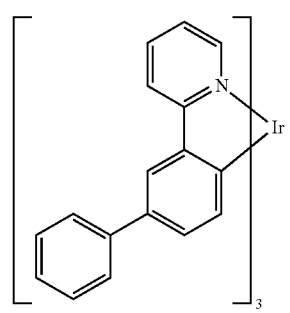
D-19
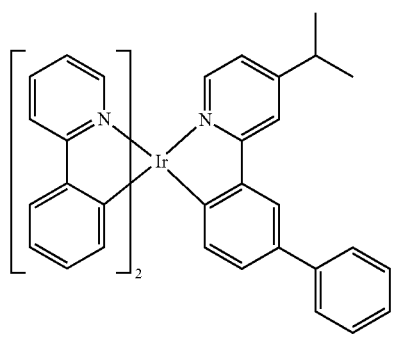
D-20
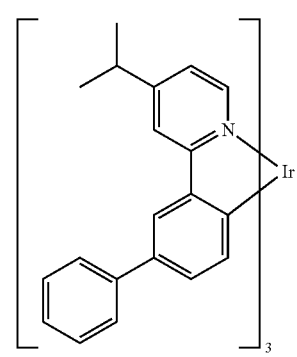
D-21
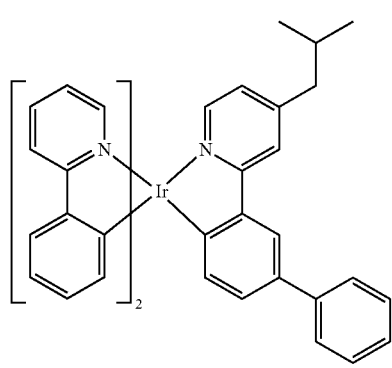
D-22
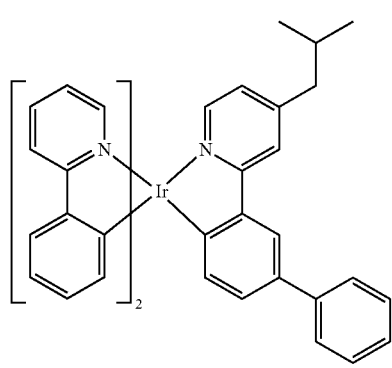
D-23
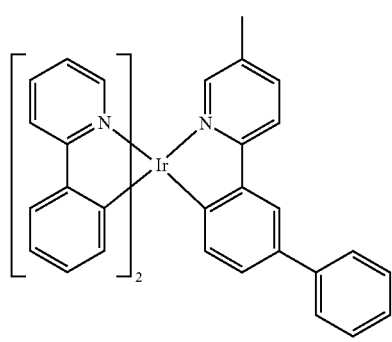
D-24
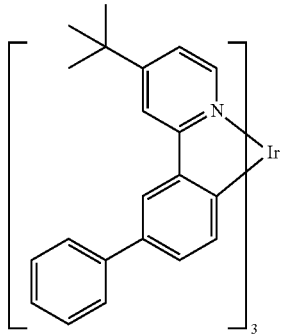

D-25
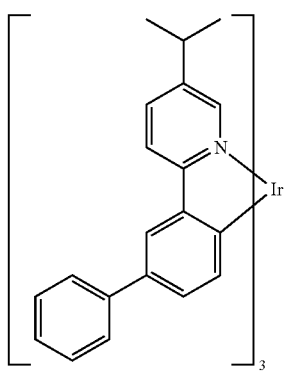
D-26
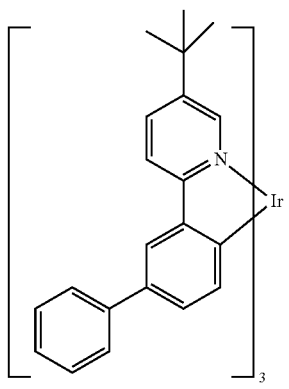
D-27
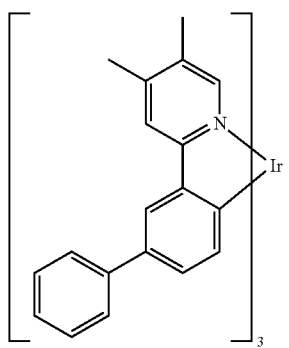
D-28
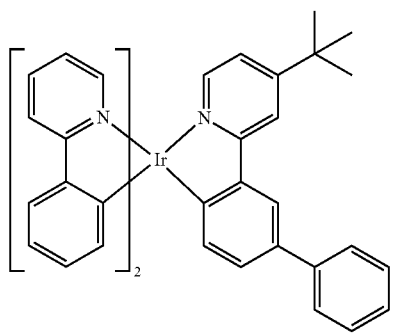
D-29
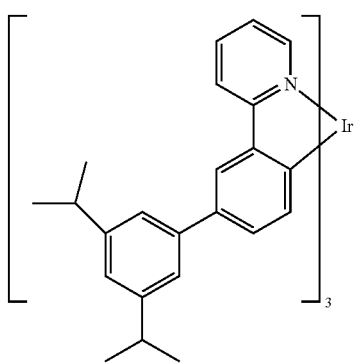
D-30
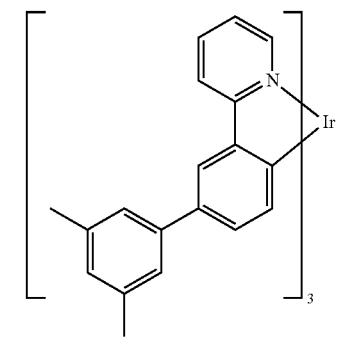
D-31
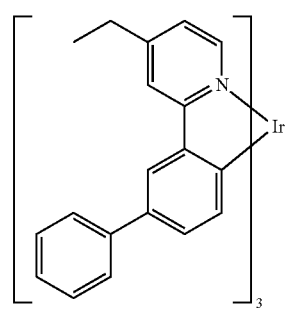
D-32
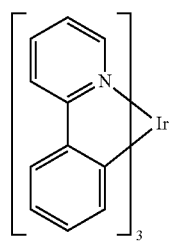
D-33
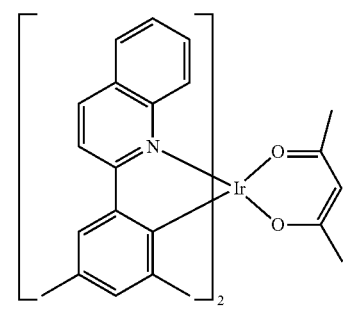

D-34
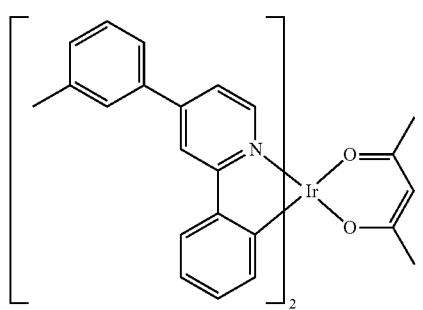
D-35
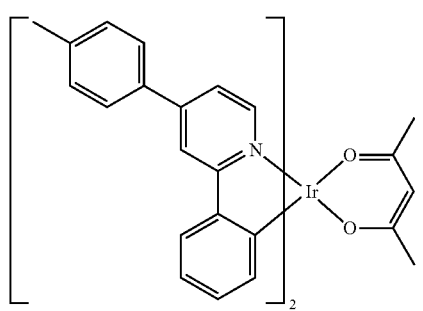
D-36
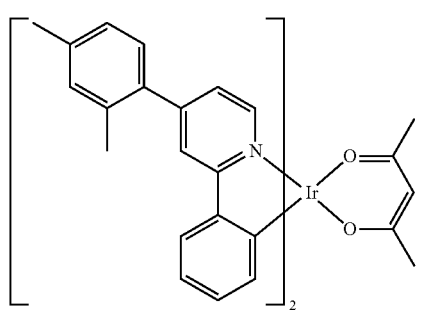
D-37
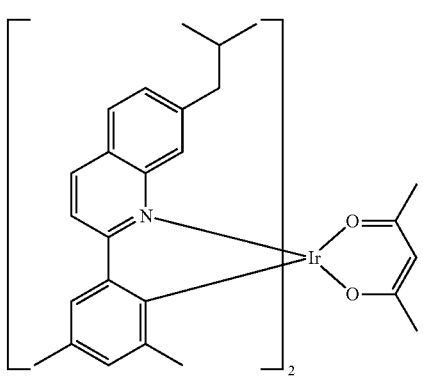
D-38
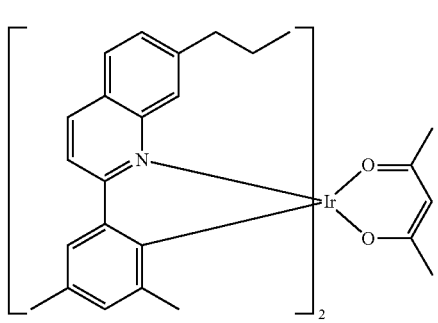
D-39
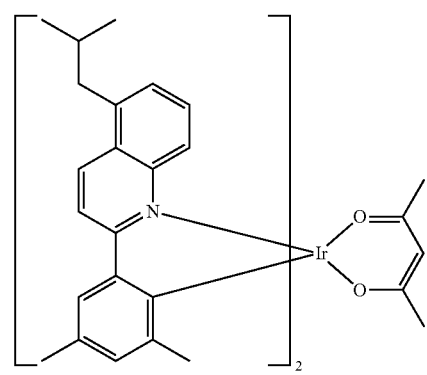
D-40
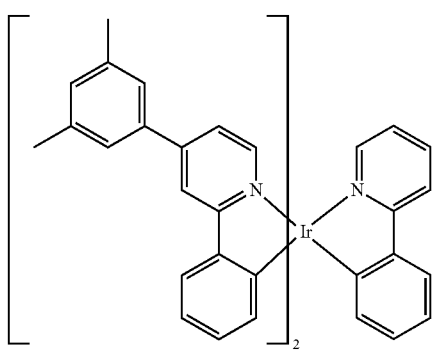
D-41
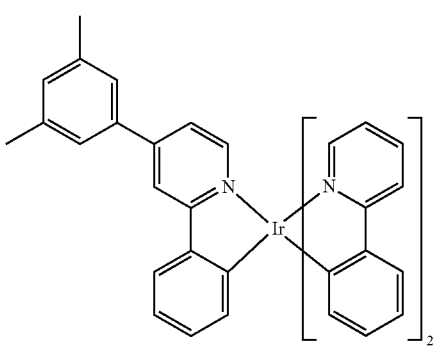
D-42
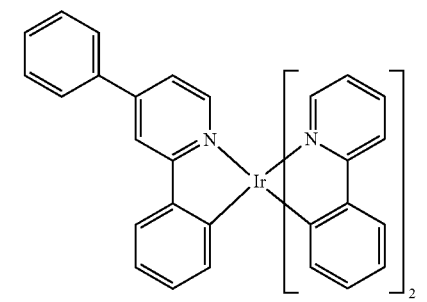

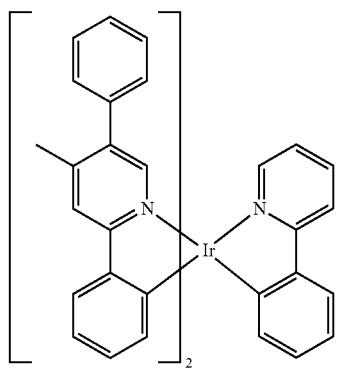 D-43
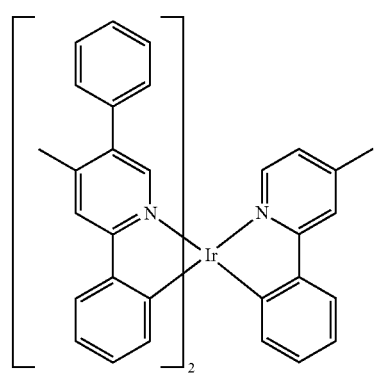 D-44
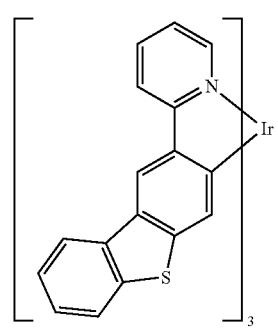 D-45
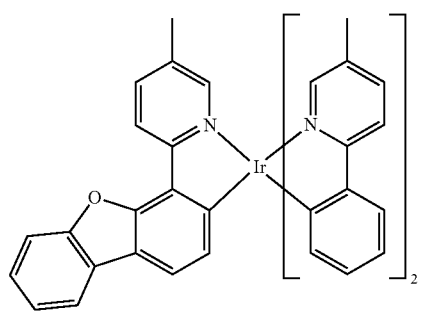 D-46
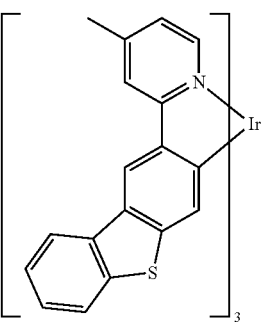 D-47
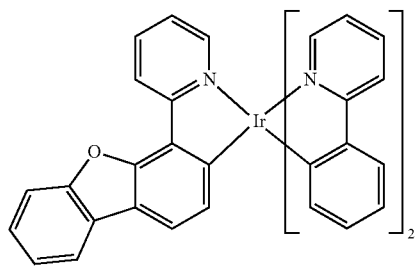 D-48
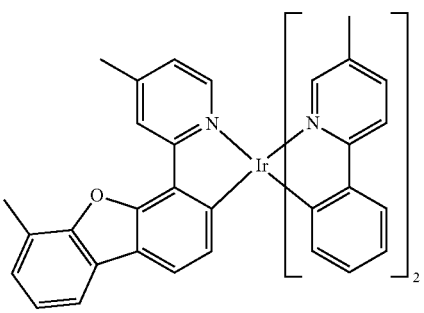 D-49
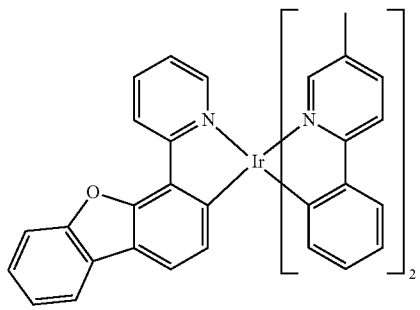 D-50
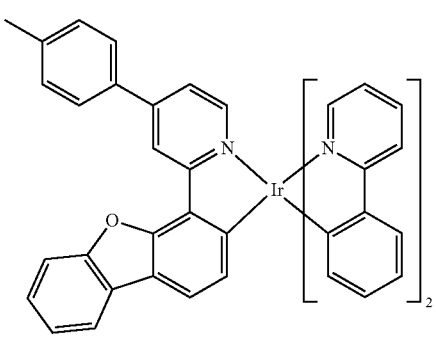 D-51

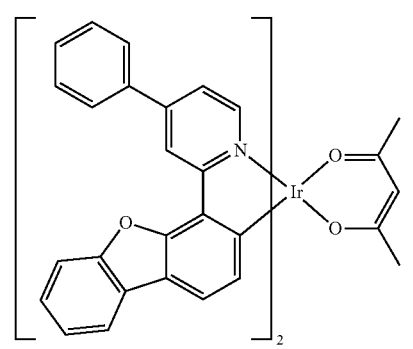 D-52
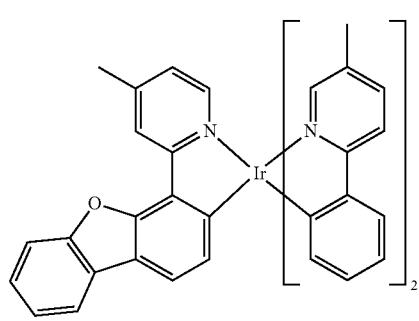 D-53
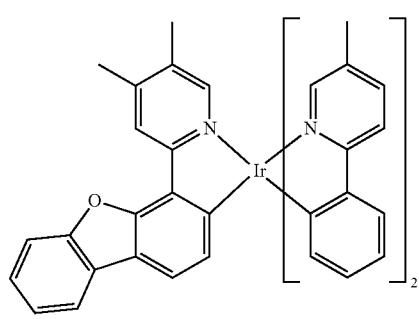 D-54
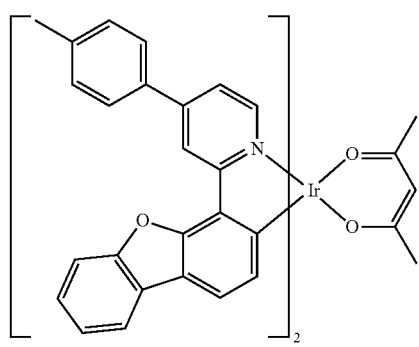 D-55
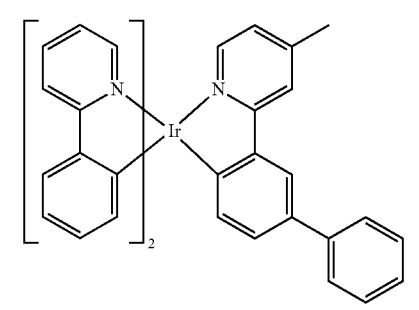 D-56
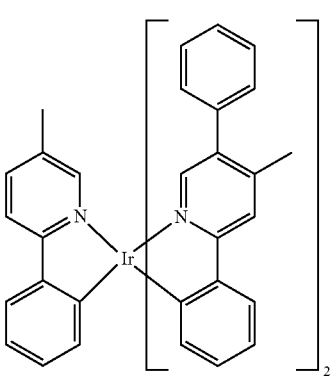 D-57
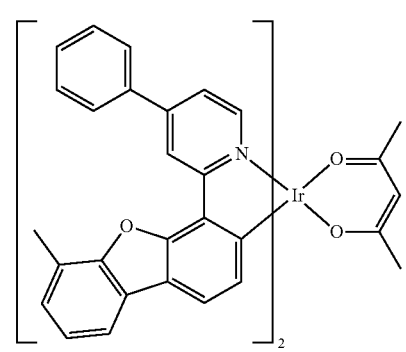 D-58
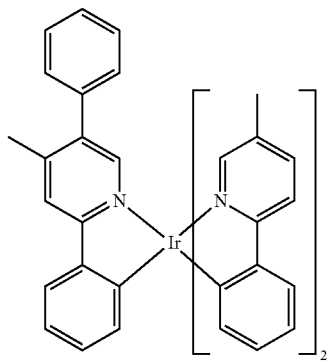 D-59
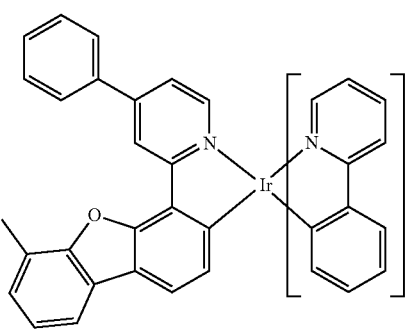 D-60

-continued
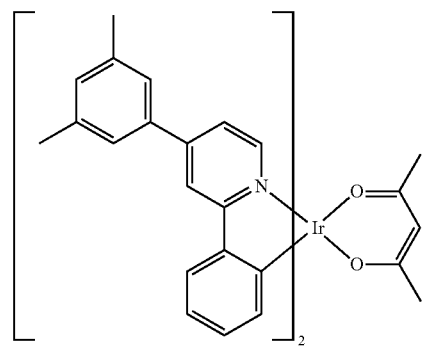
D-61
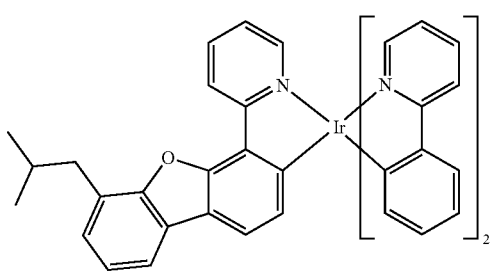
D-62
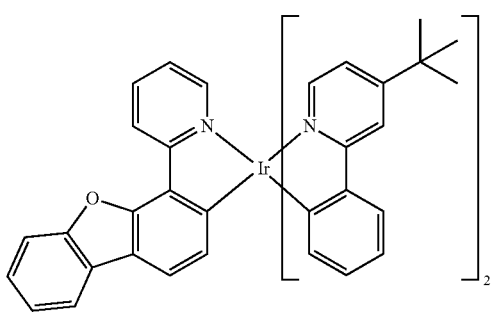
D-63
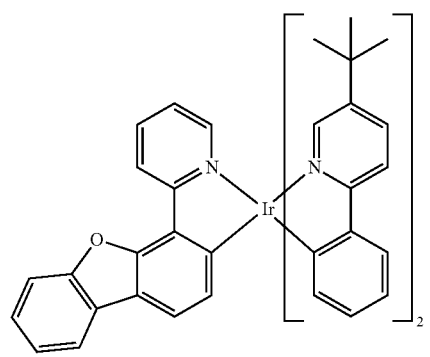
D-64
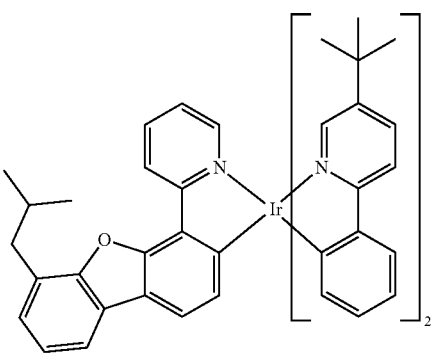
D-65
-continued
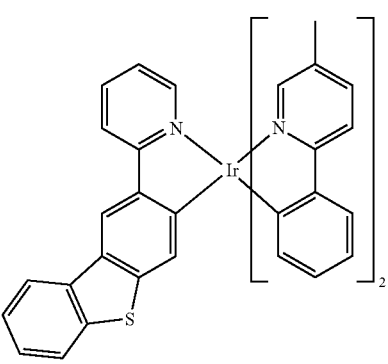
D-66
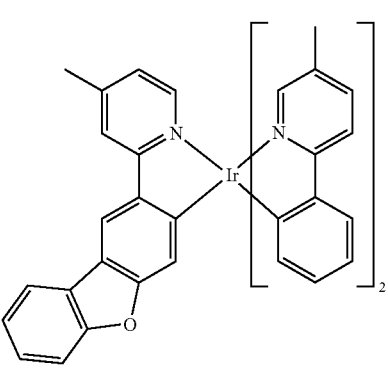
D-67
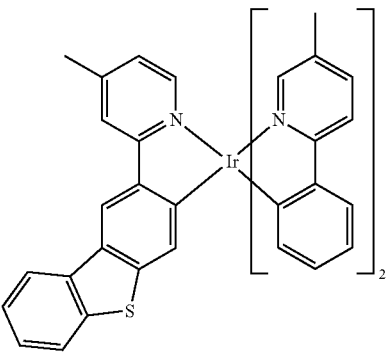
D-68
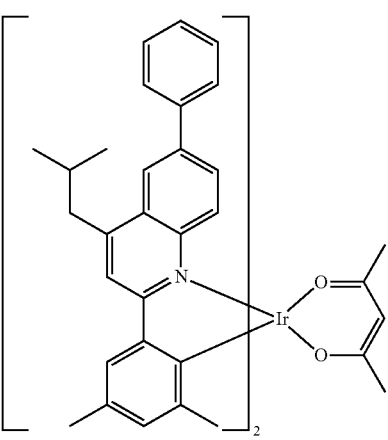
D-69

-continued
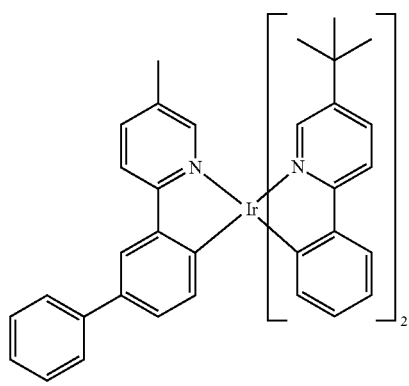
D-70
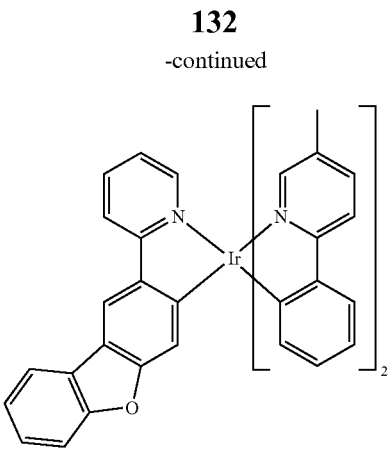
D-75
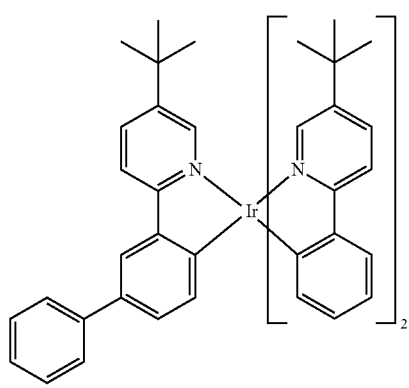
D-71
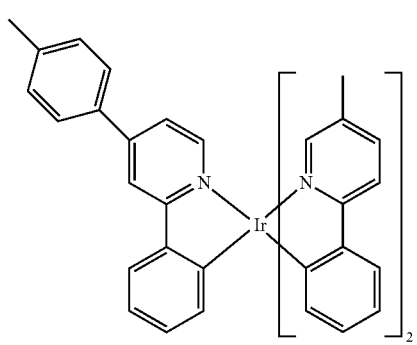
D-76
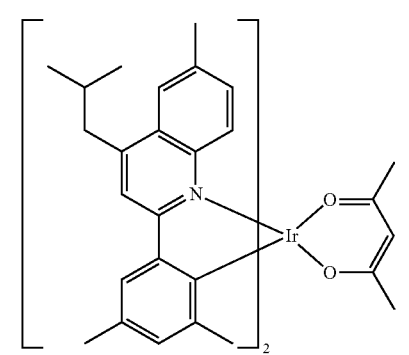
D-72
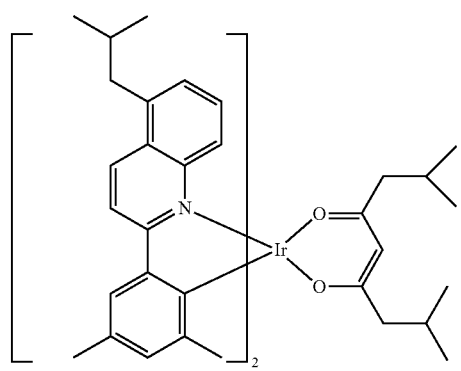
D-77
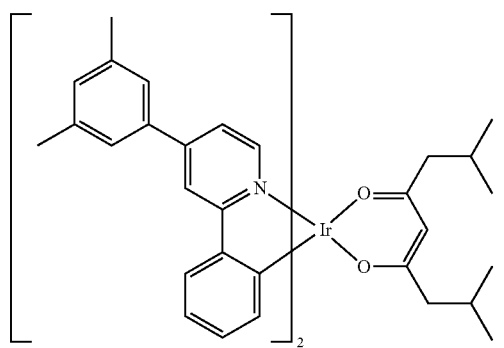
D-73
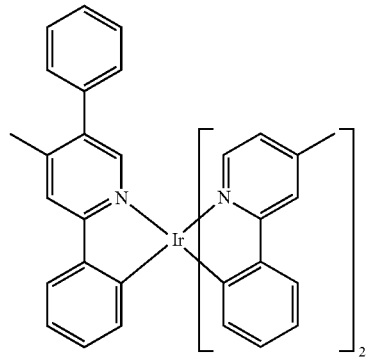
D-78

-continued
D-79
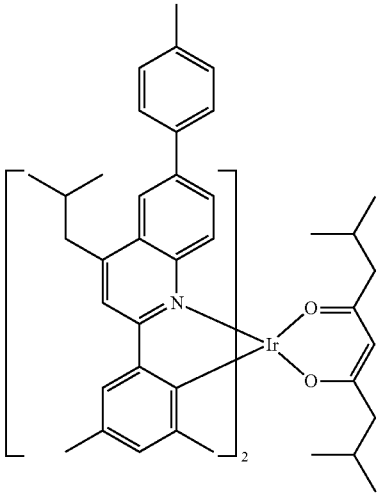
D-80
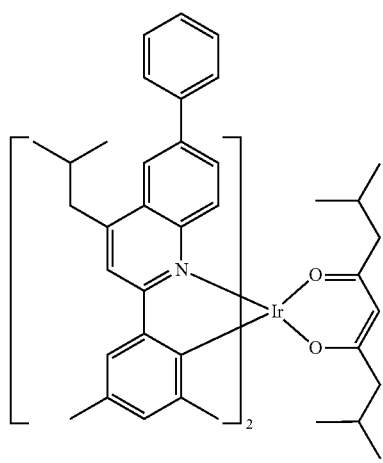
D-81
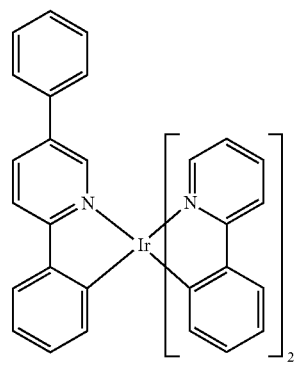
D-82
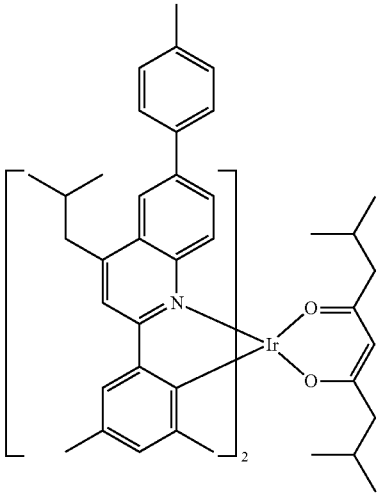
D-83
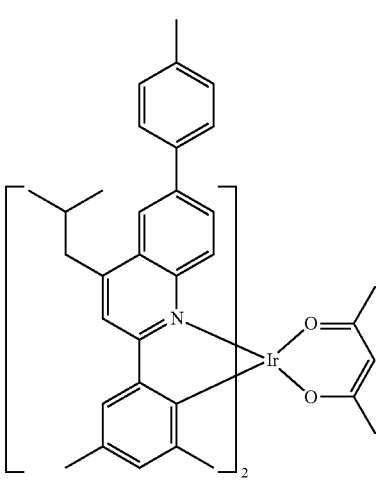
D-84
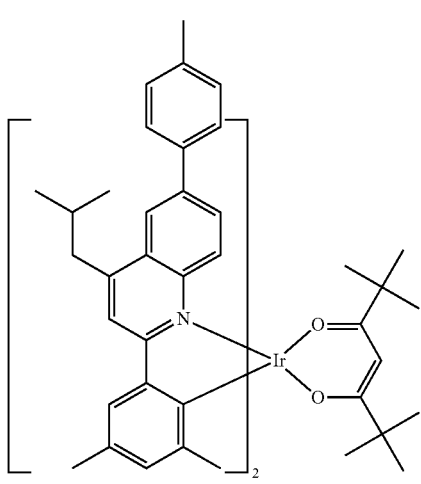

-continued
D-85
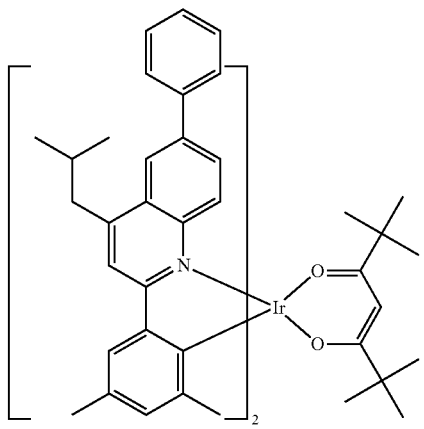
D-86
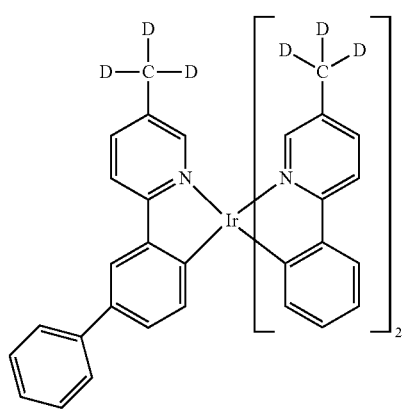
D-87
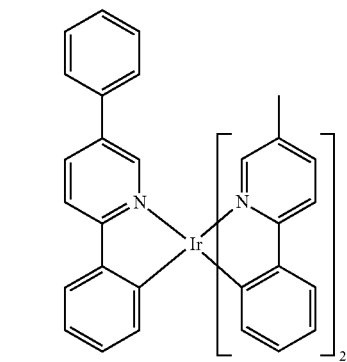
D-88
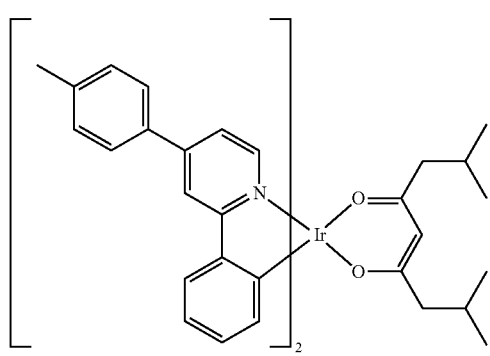
-continued
D-89
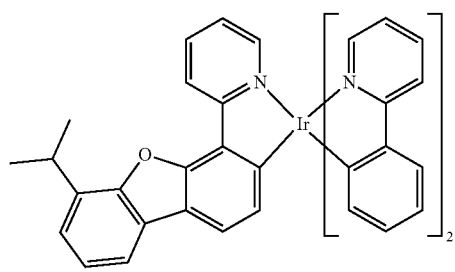
D-90
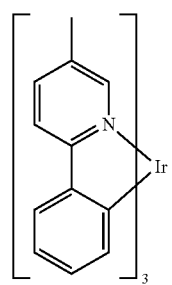
D-91
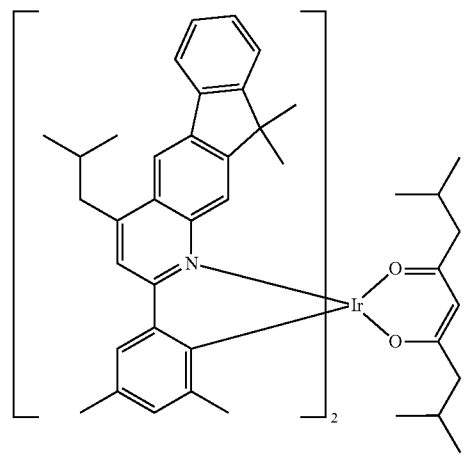
D-92
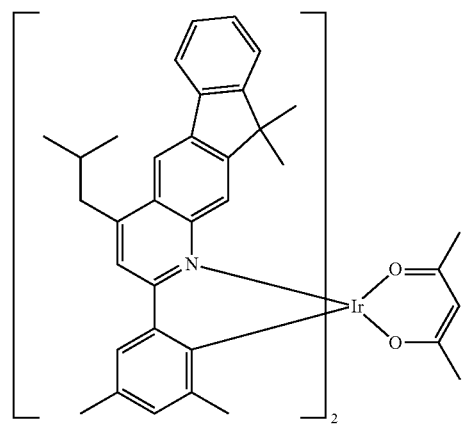

D-93
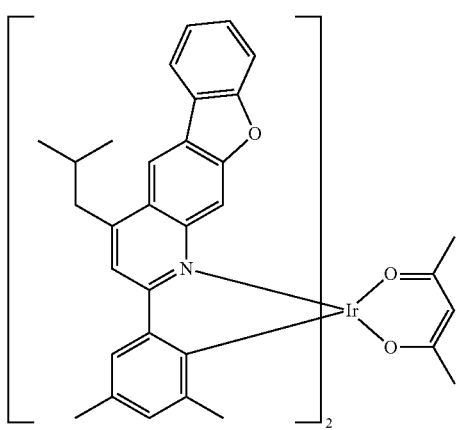
D-94
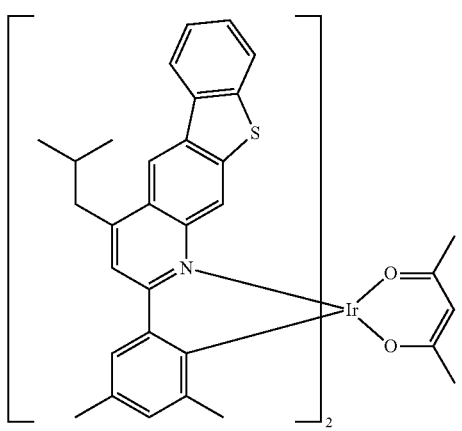
D-95
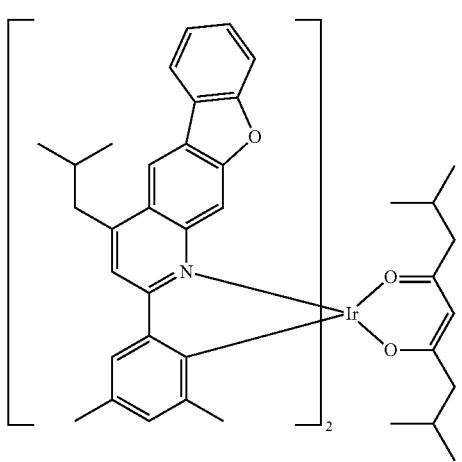
D-96
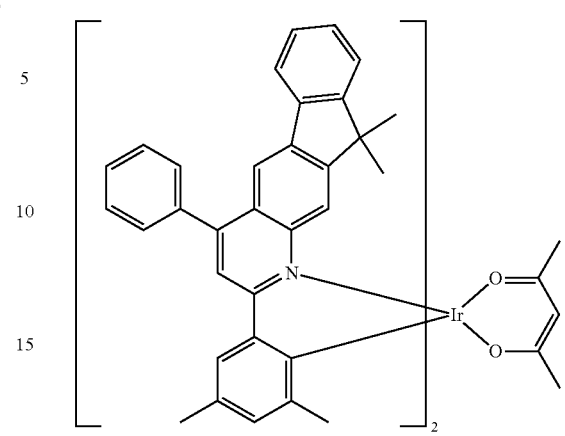
D-97
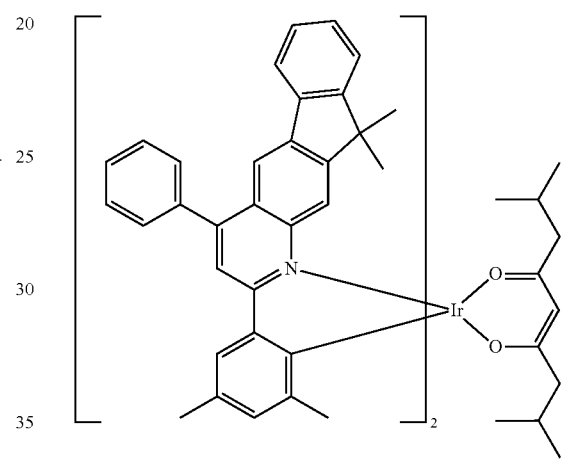
D-98
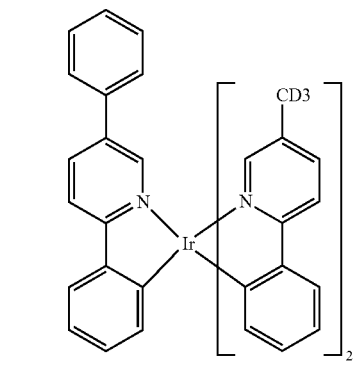
D-99
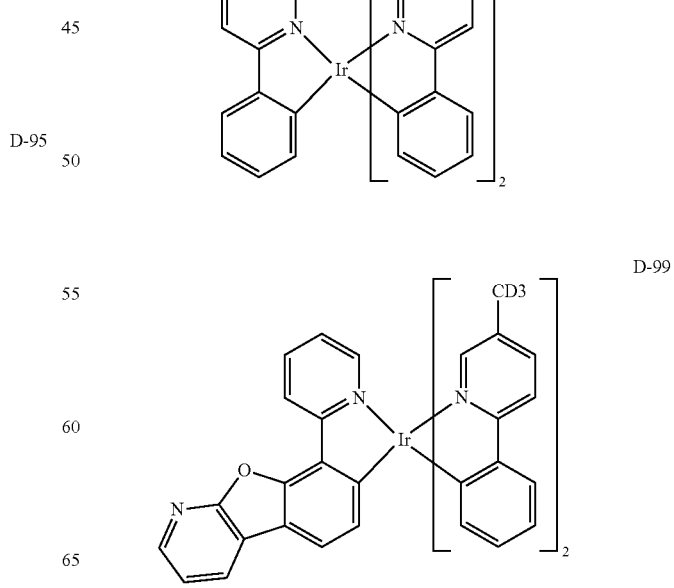

D-100 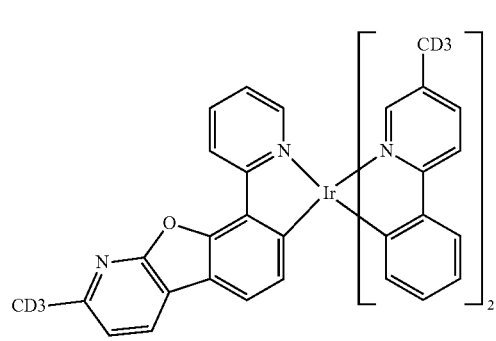
D-101 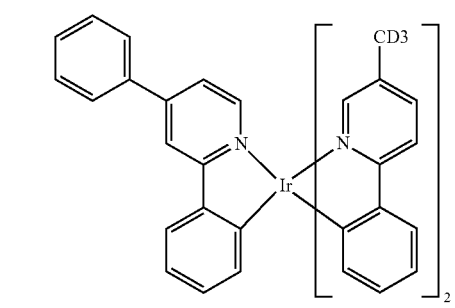
D-102 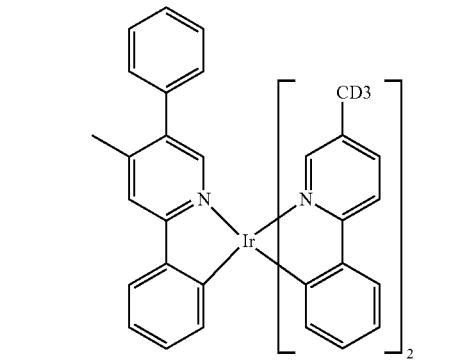
D-103 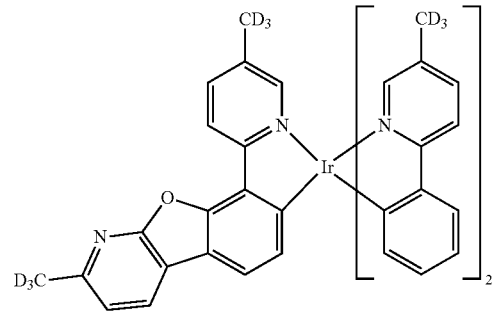
D-104 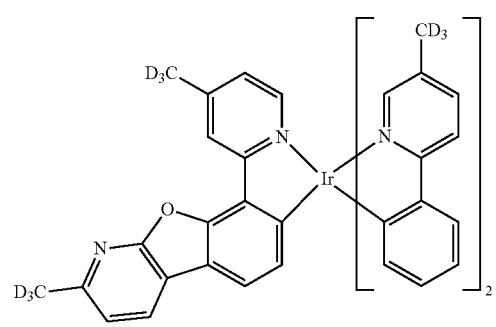
D-105 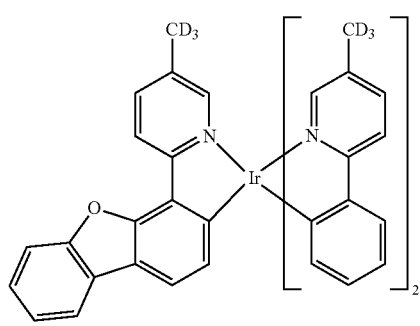
D-106 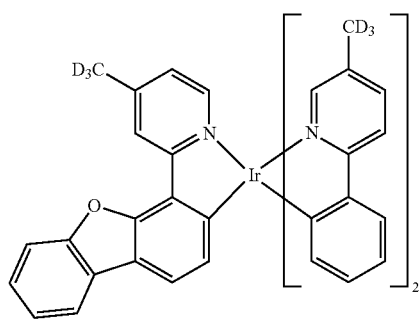
D-107 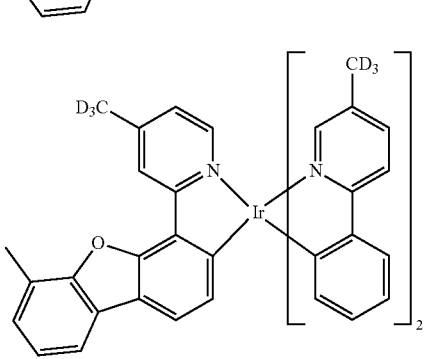
D-108 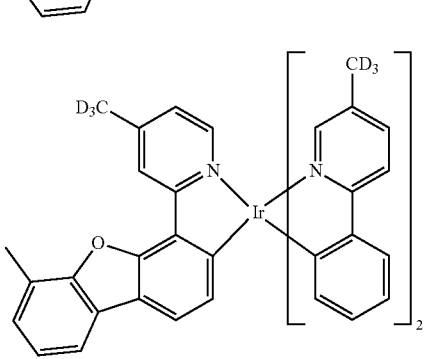
D-109 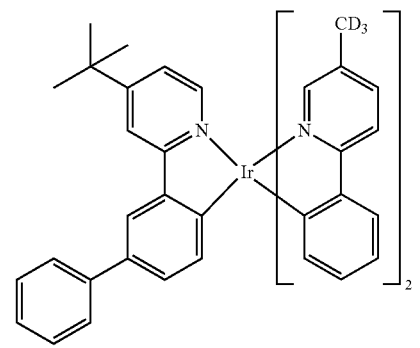

-continued
D-110
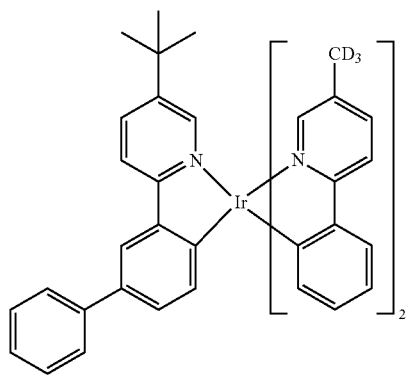
D-114
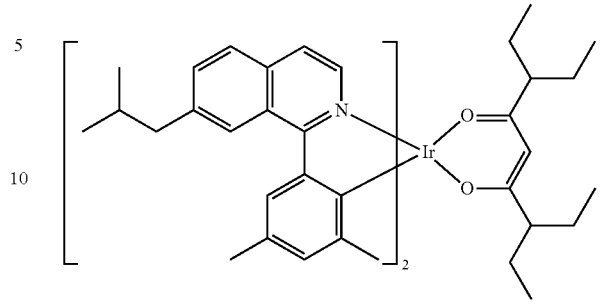
D-111
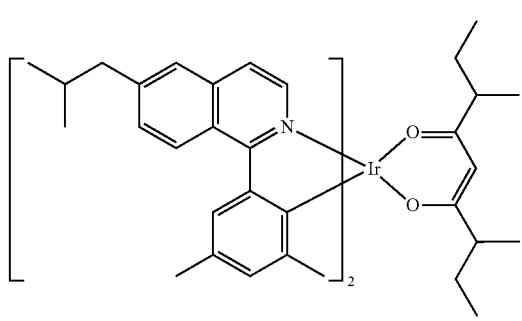
D-115
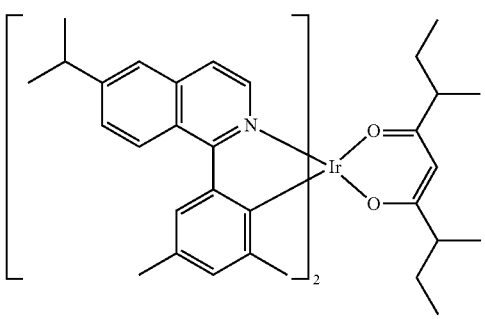
D-112
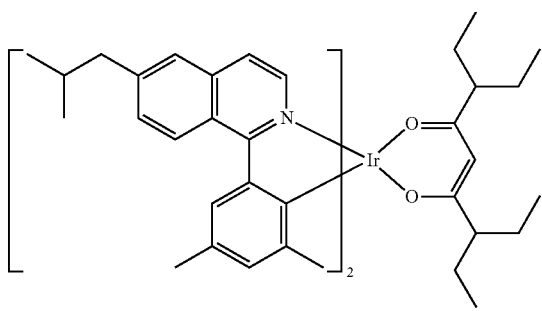
D-116
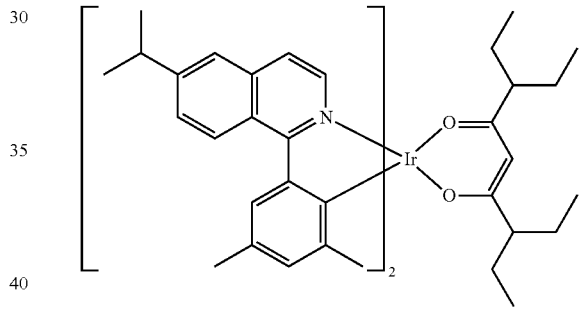
D-117
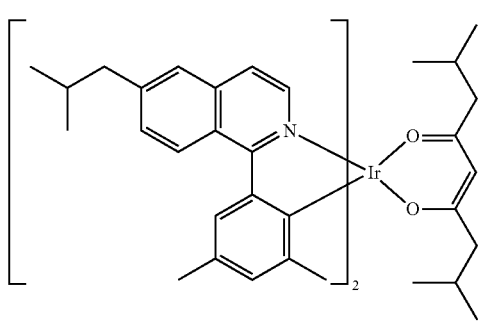
D-113
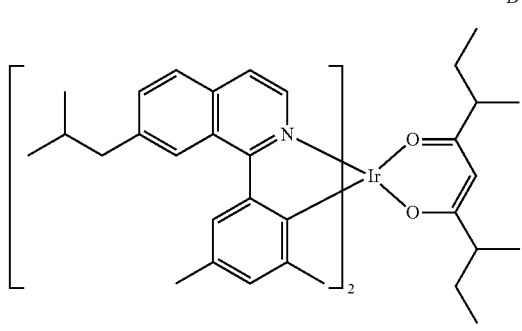
D-118
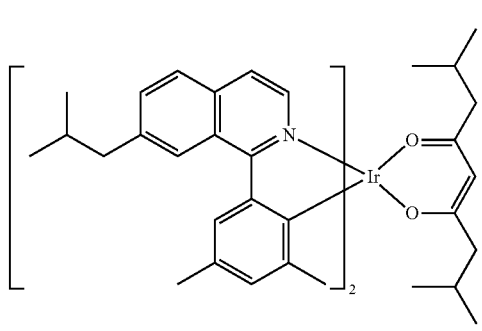

-continued

D-119

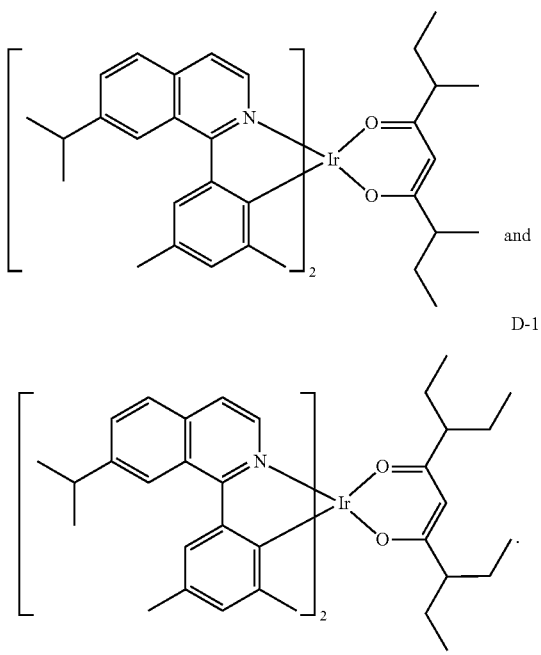

and

D-120

The compound represented by formula 1 of the present disclosure may be comprised in at least one layer constituting an organic electroluminescent device, e.g., a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. In addition, the compound represented by formula 1 of the present disclosure may be comprised in at least one layer constituting the hole transport zone, but is not limited thereto. When comprised in at least one layer constituting the hole transport zone, it may be comprised in a hole transport layer, a hole auxiliary layer, or a light-emitting auxiliary layer.

The organic electroluminescent material of the present disclosure, for example, at least one material of a hole injection material, a hole transport material, a hole auxiliary material, a light-emitting auxiliary material, an electron blocking material, a light-emitting material, an electron buffer material, a hole blocking material, an electron transport material, and an electron injection material may comprise the compound represented by formula 1. The material may be a hole transport zone material. The hole transport zone material can be comprised of the compound represented by formula 1 alone, or can further include conventional materials generally used in organic electroluminescent materials.

The organic electroluminescent device of the present disclosure comprises a first electrode; a second electrode; and at least one organic layer between the first and second electrodes. One of the first and second electrodes may be an anode, and the other may be a cathode. The organic layer may comprise at least one light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

According to one embodiment of the present disclosure, the organic electroluminescent device of the present disclosure may further comprise an azine-based compound as one or more of an electron transport material, an electron injection material, an electron buffer material, and a hole blocking material, besides the organic electroluminescent compound of the present disclosure.

The organic electroluminescent device of the present disclosure may comprise the compound represented by formula 1, and may further include conventional materials generally used in organic electroluminescent materials. The organic electroluminescent device comprising the organic electroluminescent compound represented by formula 1 of the present disclosure may exhibit high luminous efficiency and/or long lifespan characteristics. In addition, even though the compound has a relatively low molecular weight compared to conventional organic electroluminescent compounds, it can have a high glass transition temperature, e.g., 130° C. or higher, due to a twisted structure.

In addition, the present disclosure may provide a display system using the compound represented by formula 1. That is, by using the compound of the present disclosure, a display system or a lighting system can be produced. Specifically, by using the compound of the present disclosure, a display system, for example, for smartphones, tablets, notebooks, PCs, TVs, or vehicles, or a lighting system, for example, an indoor or outdoor lighting system, can be produced.

Hereinafter, the preparation method of the organic electroluminescent compounds of the present disclosure, and the physical properties of the compounds will be explained in detail with reference to the representative compounds of the present disclosure. However, the following Examples are intended to explain the present disclosure, and the present disclosure is not limited thereto.

Example 1: Preparation of Compound A-1

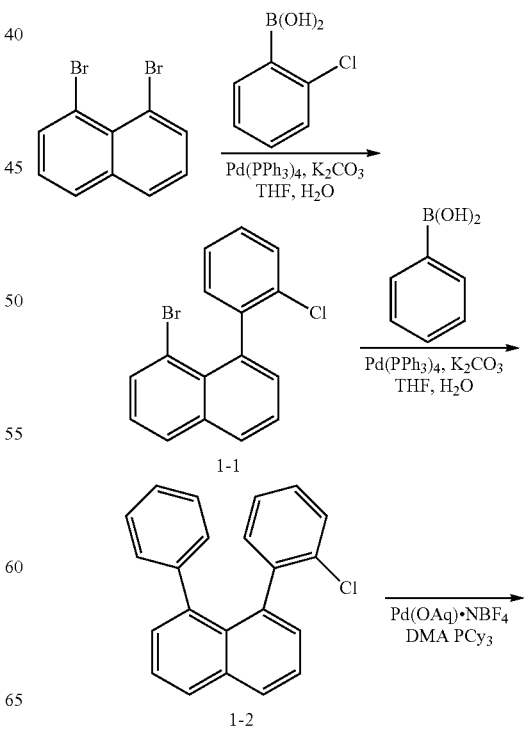

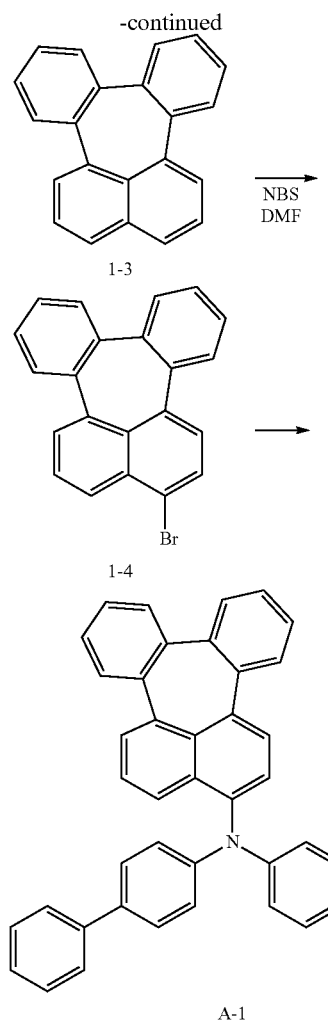

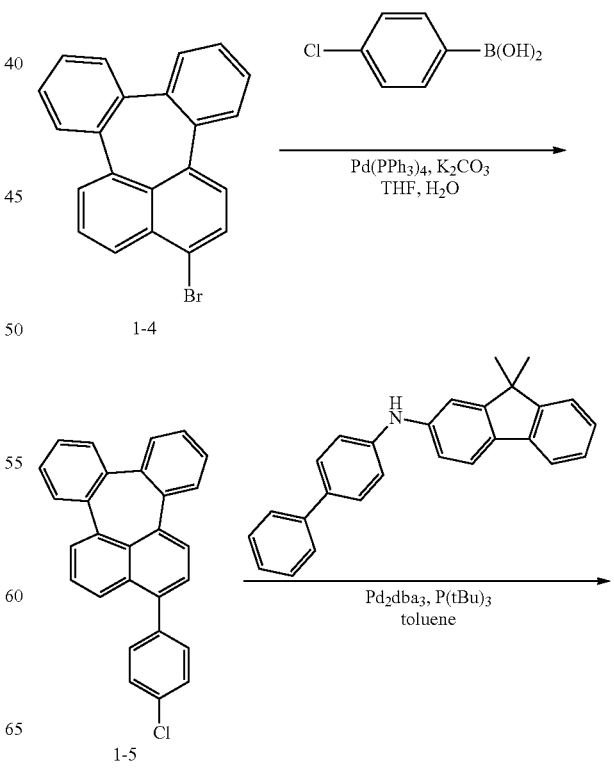

tetrafluoroborate) (24.8 mmol), 80.7 g of $Cs_2CO_3$ (247.8 mmol), and 413 mL of dimethyl acetamide (DMA) were stirred under reflux for 3 hours. The mixture was cooled to room temperature and distilled water was added thereto. The mixture was extracted with methylene chloride (MC) and dried with magnesium sulfate. The residue was distilled under reduced pressure and separated with column chromatography to obtain 23 g of compound 1-3 (yield: 70%).

4) Preparation of Compound 1-4

7 g of compound 1-3 (25.1 mmol) was dissolved in 125 mL of dimethyl formamide (DMF), and 5.4 g of N-bromosuccinimide (NBS) (30.1 mmol) was added thereto. After stirring the mixture for 4 hours at room temperature, methanol and distilled water were added thereto. The obtained solid was filtered under reduced pressure and separated with column chromatography to obtain 5.6 g of compound 1-4 (yield: 62%).

5) Preparation of Compound A-1

5.6 g of compound 1-4 (15.7 mmol), 5.6 g of di([1,1'-biphenyl]-4-yl)amine (17.3 mmol), 0.72 g of tris(dibenzylideneaceton)dipalladium(0) (0.79 mmol), 0.64 mL of tri-t-butylphosphine (1.57 mmol, 50% toluene solution), 3.0 g of sodium t-butoxide (31.4 mmol), and 157 mL of toluene were introduced into a flask, and the mixture was refluxed for 2 hours. The reaction solution was cooled to room temperature, and the solvent was then removed by a rotary evaporator. The residue was separated by column chromatography to obtain 7.6 g of yellow solid compound A-1 (yield: 81%) (melting point (M.P.): 224° C.).

Example 2: Preparation of Compound A-22

1) Preparation of Compound 1-1

100 g of 1,8-dibromonaphthalene (349.7 mmol), 82 g of (2-chlorophenyl)boronic acid (524.6 mmol), 20.2 g of tetrakis(triphenylphosphine)palladium(0) $(Pd(PPh_3)_4)$ (17.5 mmol), and 120.8 g of potassium carbonate (874.5 mmol) were dissolved in 1500 mL of tetrahydrofuran and 400 mL of distilled water in a flask, and the mixture was refluxed at 100° C. for 18 hours. After completion of the reaction, an organic layer was extracted with ethyl acetate, the remaining moisture was removed using magnesium sulfate, and the residue was dried and separated with column chromatography to obtain 78 g of compound 1-1 (yield: 70%).

2) Preparation of Compound 1-2

30 g of compound 1-1 (94.5 mmol), 15 g of phenylboronic acid (122.9 mmol), 5.5 g of tetrakis(triphenylphosphine) palladium(0) $(Pd(PPh_3)_4)$ (4.73 mmol), and 32.7 g of potassium carbonate (236.3 mmol) were dissolved in 480 mL of tetrahydrofuran and 120 mL of distilled water in a flask, and the mixture was refluxed at 100° C. for 18 hours. After completion of the reaction, an organic layer was extracted with ethyl acetate, the remaining moisture was removed using magnesium sulfate, and the residue was dried and separated with column chromatography to obtain 26 g of compound 1-2 (yield: 87%).

3) Preparation of Compound 1-3

26 g of compound 1-2 (82.6 mmol), 3.7 g of $Pd(OAc)_2$ (16.5 mmol), 9.1 g of ligand(tricyclohexylphosphonium -continued

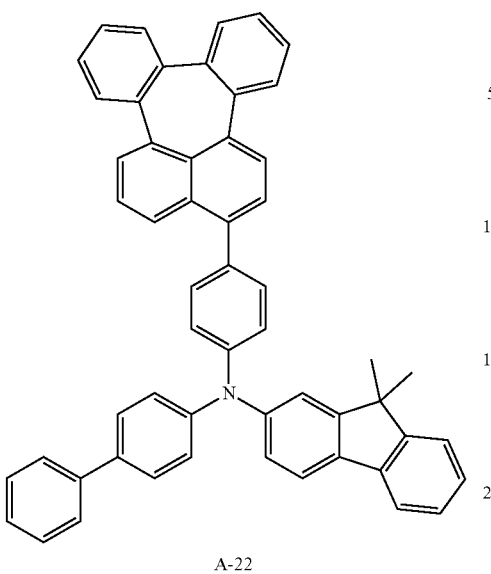

A-22

1) Preparation of Compound 1-5

7.0 g of compound 1-4 (19.6 mmol), 4.0 g of 4-chlorophenylboronic acid (25.5 mmol), 1.13 g of tetrakis(triphenylphosphine)palladium(0) (Pd(PPh₃)₄) (0.98 mmol), and 6.8 g of potassium carbonate (49 mmol) were dissolved in 100 mL of tetrahydrofuran and 25 mL of distilled water in a flask, and the mixture was refluxed at 100° C. for 18 hours. After completion of the reaction, an organic layer was extracted with ethyl acetate, the remaining moisture was removed using magnesium sulfate, and the residue was dried and separated with column chromatography to obtain 6.1 g of compound 1-5 (yield: 80%)

2) Preparation of Compound A-22

6.1 g of compound 1-5 (15.7 mmol), 6.3 g of N-1,1'-biphenyl-4-yl-9,9-dimethyl-9H-fluorene-2-amine (17.3 mmol), 0.72 g of tris(dibenzylideneaceton)dipalladium(0) (0.80 mmol), 0.64 mL of tri-t-butylphosphine (1.57 mmol, 50% toluene solution), 3.0 g of sodium t-butoxide (31.4 mmol), and 160 mL of toluene were introduced into a flask, and the mixture was refluxed for 4 hours. The reaction solution was cooled to room temperature, and the solvent was then removed by a rotary evaporator. The residue was separated by column chromatography to obtain 0.98 g of yellow solid compound A-22 (yield: 9%) (M.P.: 182° C.).

Example 3: Preparation of Compound A-13

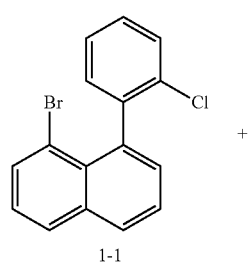

1-1

-continued

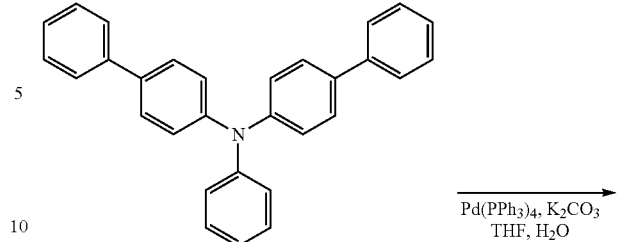

1-6

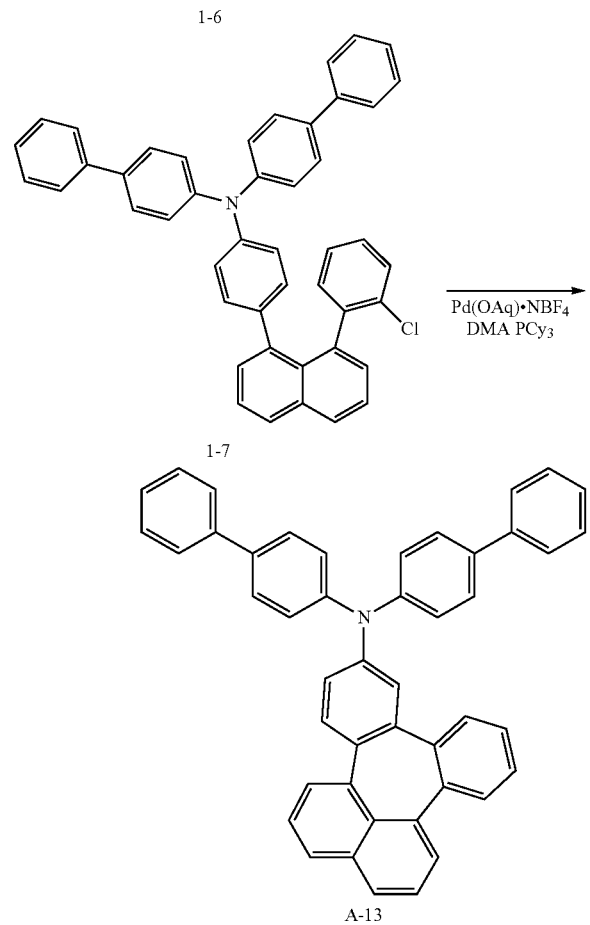

1) Preparation of Compound 1-7

15 g of compound 1-1 (47.2 mmol), 25 g of compound 1-6 (47.2 mmol), 2.7 g of tetrakis(triphenylphosphine)palladium (0) (Pd(PPh₃)₄) (2.36 mmol), and 16.3 g of potassium carbonate (118 mmol) were dissolved in 240 mL of tetrahydrofuran and 60 mL of distilled water in a flask, and the mixture was refluxed at 100° C. for 18 hours. After completion of the reaction, an organic layer was extracted with ethyl acetate, the remaining moisture was removed using magnesium sulfate, and the residue was dried and separated with column chromatography to obtain 14.8 g of compound 1-7 (yield: 49%)

2) Preparation of Compound A-13

14 g of compound 1-7 (22.1 mmol), 0.99 g of Pd(OAc)₂ (4.42 mmol), 2.44 g of ligand(tricyclohexylphosphonium tetrafluoroborate) (6.63 mmol), 21.6 g of $Cs_2CO_3$ (66.3 mmol), and 110 mL of dimethyl acetamide (DMA) were stirred under reflux for 3 hours. The mixture was cooled to room temperature and distilled water was added thereto. The mixture was extracted with methylene chloride (MC) and dried with magnesium sulfate. The residue was distilled under reduced pressure and separated with column chromatography to obtain 2.4 g of yellow solid compound A-13 (yield: 18%) (M.P.: 161° C.).

Hereinafter, the performance of the organic electroluminescent device comprising the compound according to the present disclosure is explained.

Device Example 1: Production of an OLED Using the Organic Electroluminescent Compound According to the Present Disclosure An OLED using the organic electroluminescent compound according to the present disclosure was produced as follows. A transparent electrode indium tin oxide (ITO) thin film (10 Ω/sq) on a glass substrate for an OLED (Geomatec, Japan) was subjected to an ultrasonic washing with acetone and isopropanol, sequentially, and was then stored in isopropanol. Next, the ITO substrate was mounted on a substrate holder of a vacuum vapor depositing apparatus. Compound HIL-1 was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 90 nm on the ITO substrate. Compound HIL-2 was then introduced into another cell of said vacuum vapor depositing apparatus, and was evaporated by applying an electric current to the cell, thereby forming a second hole injection layer having a thickness of 5 nm on the first hole injection layer. Compound HTL-1 was introduced into another cell of said vacuum vapor depositing apparatus, and was evaporated by applying an electric current to the cell, thereby forming a first hole transport zone having a thickness of 10 nm on the second hole injection layer. Compound A-1 was introduced into another cell of said vacuum vapor depositing apparatus, and was evaporated by applying an electric current to the cell, thereby forming a second hole transport zone (auxiliary layer) having a thickness of 60 nm on the first hole transport zone. After forming the hole injection layers and the hole transport zones, a light-emitting layer was then deposited as follows. Compound H-164 was introduced into one cell of the vacuum vapor depositing apparatus as a host, and compound D-39 was introduced into another cell as a dopant. The two materials were evaporated and deposited in a doping amount of 2 wt % (the amount of dopant) based on the total amount of the dopant and host to form a light-emitting layer having a thickness of 40 nm on the second hole transport zone. Compound ET-1 and compound EI-1 were then introduced into another two cells, evaporated at the rate of 1:1, and deposited to form an electron transport layer having a thickness of 35 nm on the light-emitting layer.

Next, after compound EI-1 as an electron injection layer having a thickness of 2 nm was deposited on the electron transport layer, an Al cathode having a thickness of 1500 nm was deposited by another vacuum vapor deposition apparatus on the electron injection layer. Thus, an OLED was produced.

Device Examples 2 and 3: Production of an OLED Using the Organic Electroluminescent Compound According to the Present Disclosure In Device Examples 2 and 3, OLEDs were produced in the same manner as in Device Example 1, except for using compounds A-22 and A-13, respectively, for the second hole transport zone (auxiliary layer).

Comparative Example 1: Production of an OLED Using the Organic Electroluminescent Compound not According to the Present Disclosure In Comparative Example 1, an OLED was produced in the same manner as in Device Example 1, except for using compound HTL-1 for the second hole transport zone (auxiliary layer).

The luminous efficiency and CIE color coordinate at a luminance of 1,000 nit, the time taken for the luminance to decrease from the initial luminance to 98% at constant current at a luminance of 5,000 nit (lifespan; T98), and the glass transition temperature of the OLEDs produced in Device Examples 1 to 3 and Comparative Example 1 are provided in Table 1 below.

TABLE 1

| | Luminous efficiency (cd/A) | Color coordinate (x, y) | Lifespan (T98) (hr) | Glass transition temperature Tg (° C.) |
|---|---|---|---|---|
| Device Example 1 | 20.0 | (0.669, 0.330) | 200 | 152 |
| Device Example 2 | 17.5 | (0.668, 0.331) | 80 | 160 |
| Device Example 3 | 16.4 | (0.668, 0.332) | 107 | 141 |
| Comparative Example 1 | 11.2 | (0.662, 0.336) | 22 | 130 |

From Table 1, it can be verified that the organic electroluminescent device comprising the organic electroluminescent compound of the present disclosure has high glass transition temperature, high luminous efficiency, and/or improved lifespan characteristics compared to the organic electroluminescent device not comprising the organic electroluminescent compound of the present disclosure.

The compounds used in the Device Examples and the Comparative Example are shown in Table 2.

TABLE 2
Hole Transport Zone
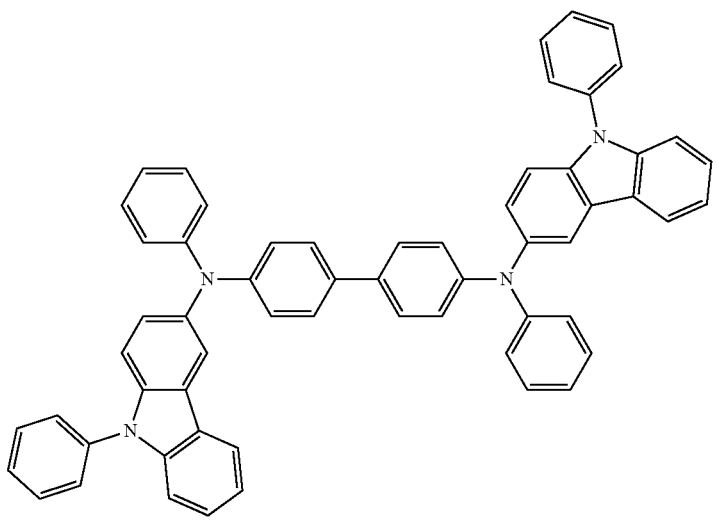
HIL-1
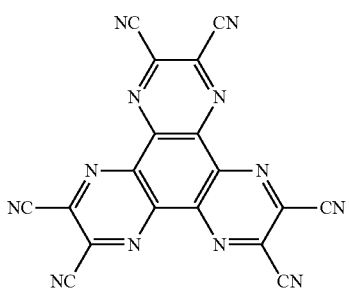
HIL-2
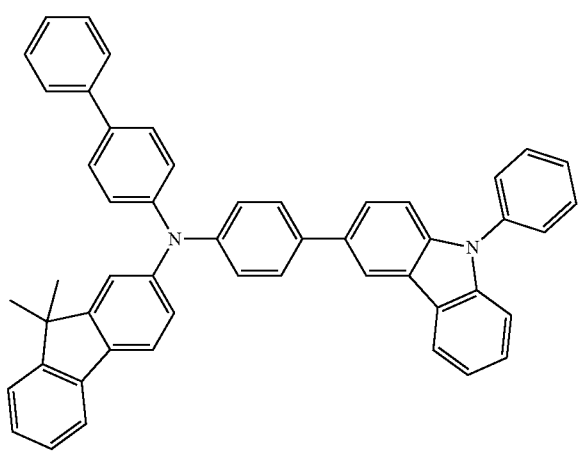
HTL-1

TABLE 2-continued
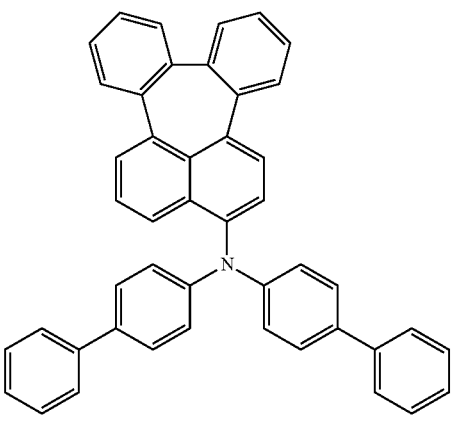
A-1
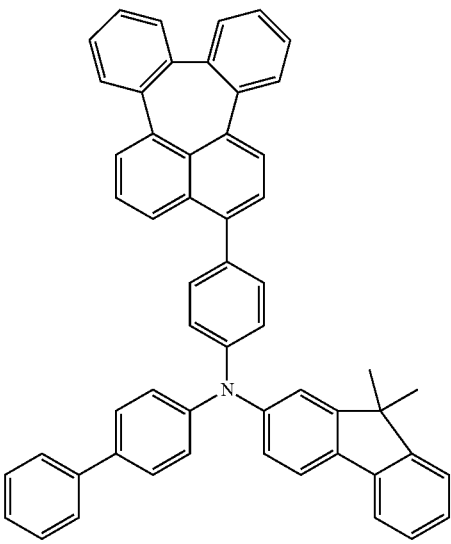
A-22
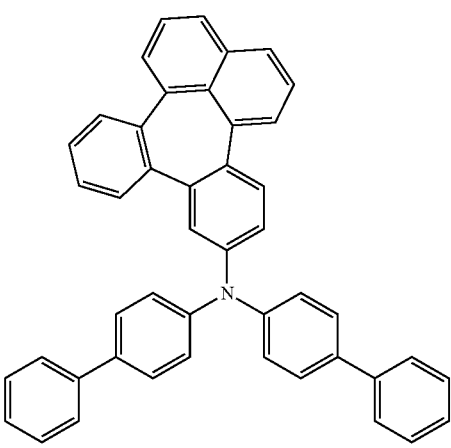
A-13

TABLE 2-continued
Light-Emitting Layer
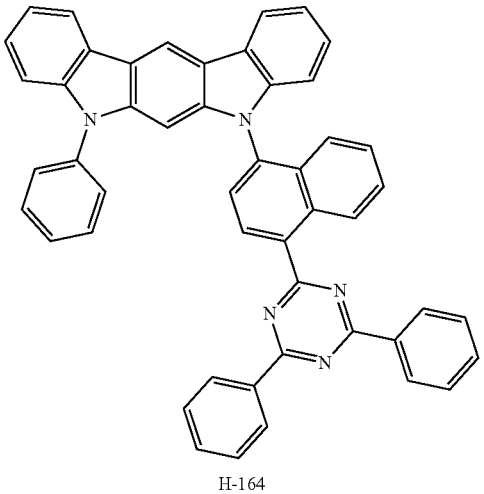 [SMILES: c1ccc(-c2nc(-c3ccccc3)nc(-c3ccc(-n4c5ccccc5c5cc6c7ccccc7n(-c7ccccc7)c6cc54)c4ccccc34)n2)cc1]
H-164
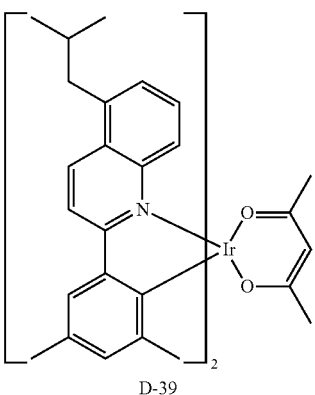
D-39
Electron Transport Layer
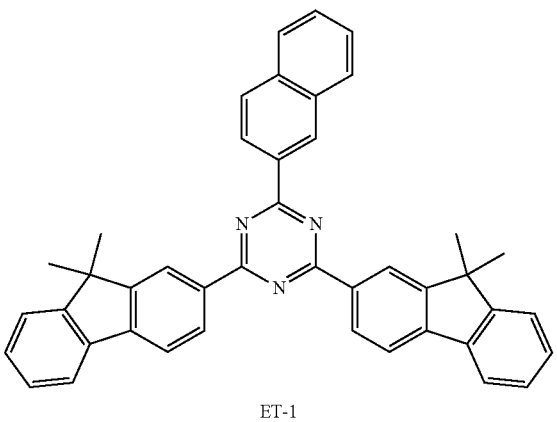 [SMILES: CC1(C)c2ccccc2-c2ccc(-c3nc(-c4ccc5c(c4)C(C)(C)c4ccccc4-5)nc(-c4ccc5ccccc5c4)n3)cc21]
ET-1
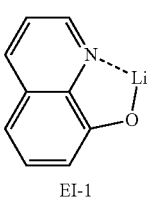
EI-1

The invention claimed is:

1. An organic electroluminescent compound represented by the following formula 1-1, 1-2 or 1-3:

wherein $X_1$ to $X_8$ each independently represent N or $CR_1$;

$R_1$ represents hydrogen;

$L_1$ and $L_2$ each independently represent a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

$Ar_1$ represents a substituted or unsubstituted (3- to 30-membered)heteroaryl or

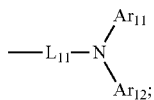

$Ar_2$ represents a substituted or unsubstituted (3- to 30-membered)heteroaryl or

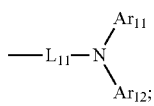

$L_{11}$ represents a single bond, a substituted or unsubstituted (C6-C30)arylene, or a substituted or unsubstituted (3- to 30-membered)heteroarylene;

$Ar_{11}$ and $Ar_{12}$ each independently represent a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl; and n and p each independently represent an integer of 1 or 2.

2. The organic electroluminescent compound according to claim 1, wherein the substituents of the substituted (C1-C30)alkyl(ene), the substituted (C6-C30)aryl(ene), the substituted (3- to 30-membered)heteroaryl(ene), and the substituted (C3-C30)cycloalkyl(ene) in $Ar_1$, $Ar_2$, $L_1$, $L_2$, $L_{11}$, $Ar_{11}$, and $Ar_{12}$ each independently are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthio, a (3- to 30-membered)heteroaryl unsubstituted or substituted with a (C6-C30)aryl, a (C6-C30)aryl unsubstituted or substituted with a (3- to 30-membered)heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino unsubstituted or substituted with a (C1-C30)alkyl(s), a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl (C1-C30)alkyl, and a (C1-C30)alkyl(C6-C30)aryl.

3. An organic electroluminescent compound represented by the following formula 2-1 or 2-2:

wherein $X_1$ to $X_8$ each independently represent N or CH;

$L_{11}$ represents a single bond, a substituted or unsubstituted (C6-C30)arylene, or a substituted or unsubstituted (3- to 30-membered)heteroarylene; and $Ar_{11}$ and $Ar_{12}$ each independently represent a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl.

4. The organic electroluminescent compound according to claim 1, wherein formula 1-1 is represented by the following formula 3-1 and formula 1-2 is represented by the following formula 3-2:

wherein

HAr represents a substituted or unsubstituted (3- to 30-membered)heteroaryl;

$X_1$ to $X_8$ each independently represent N or CH;

q represents an integer of 1 to 2; and $L_1$ and $L_2$ are as defined in claim 1.

5. The organic electroluminescent compound according to claim 1, wherein the compound represented by formula 1-1, 1-2 or 1-3 is selected from the group consisting of:

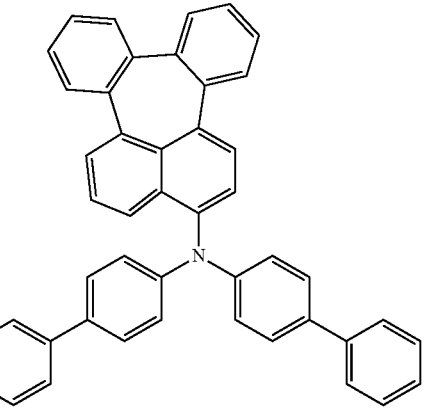

A-1

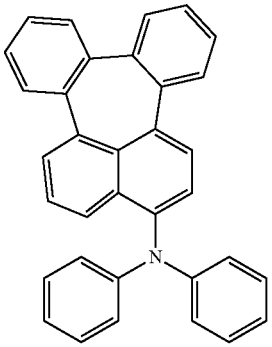

A-2

A-3
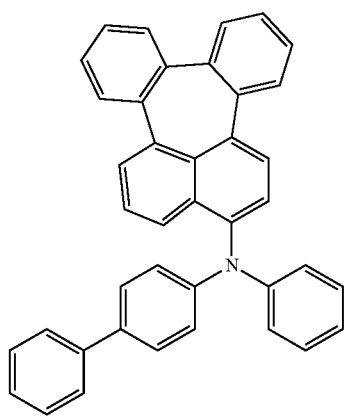
A-4
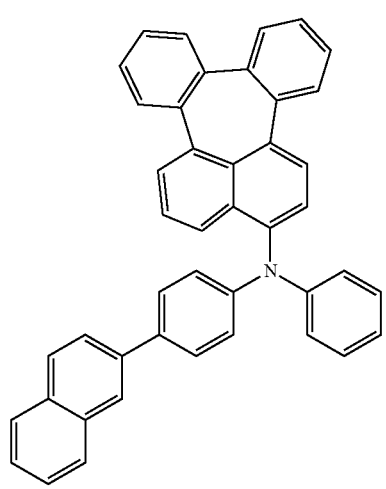
A-5
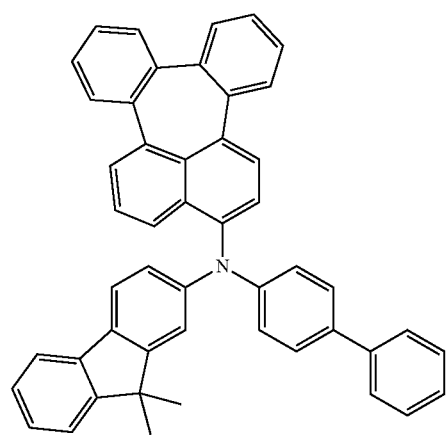
A-6
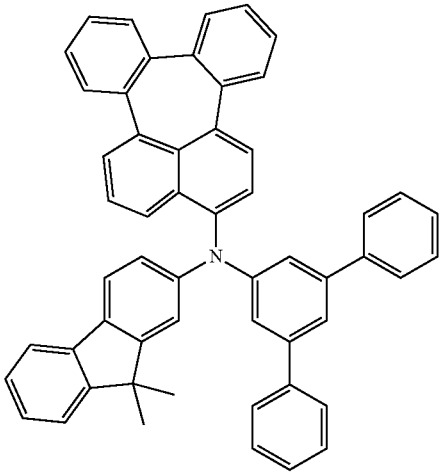
A-7
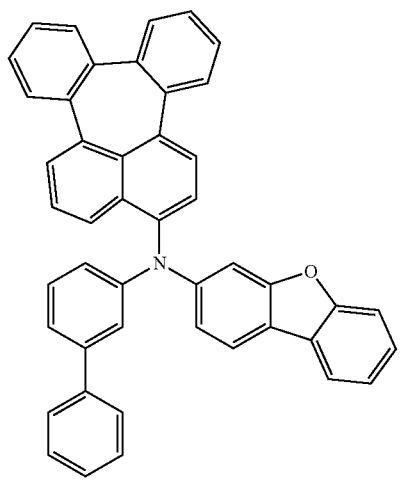
A-8
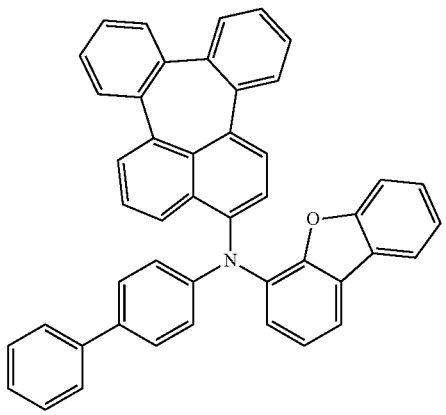

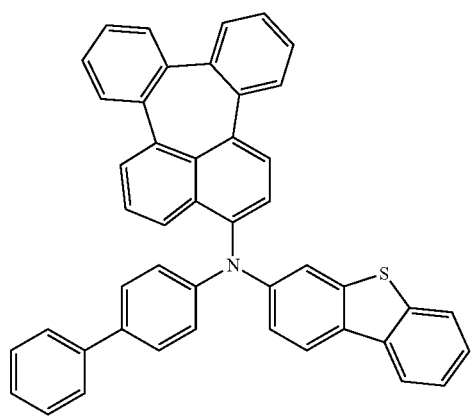
A-9
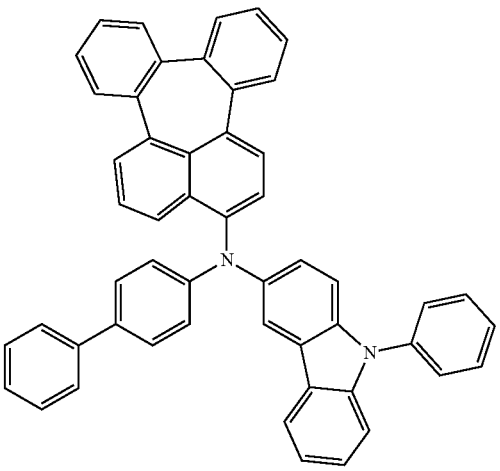
A-12
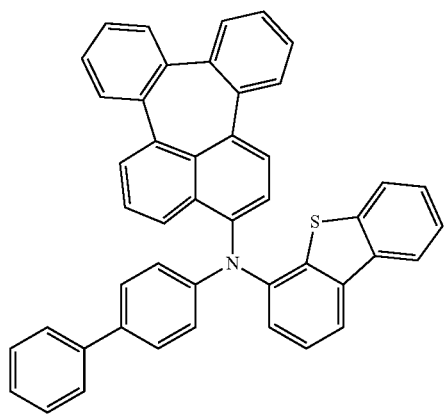
A-10
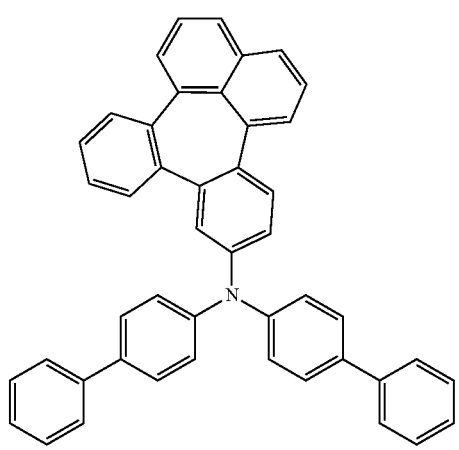
A-13
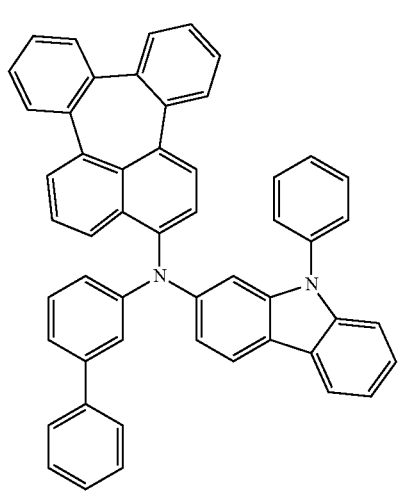
A-11
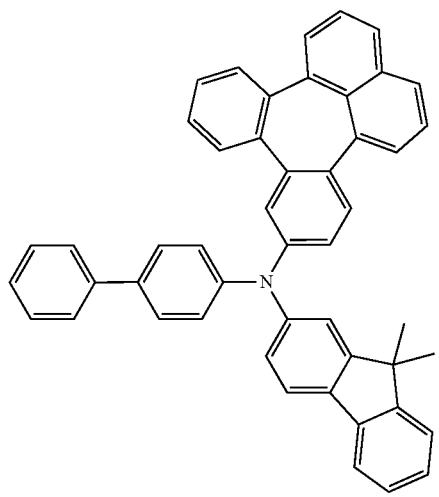
A-14

-continued
A-15
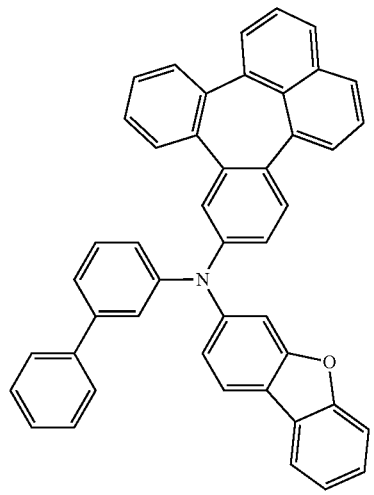
A-16
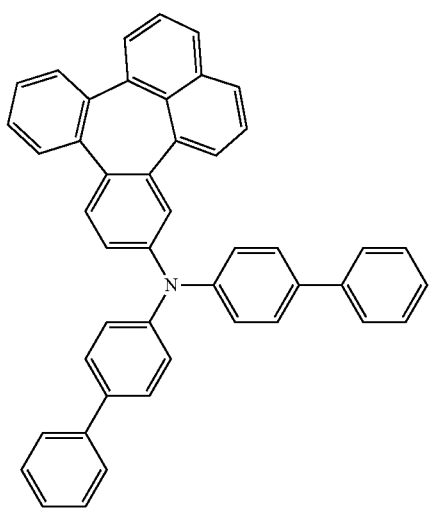
A-17
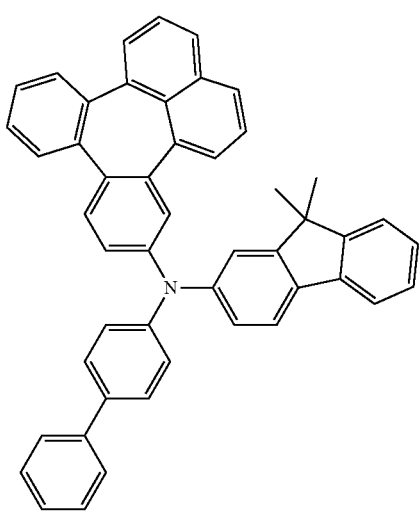
-continued
A-18
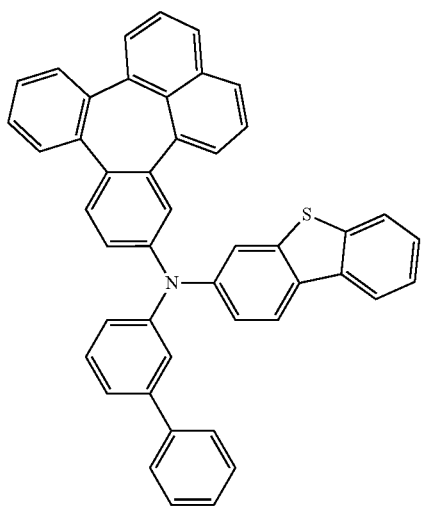
A-19
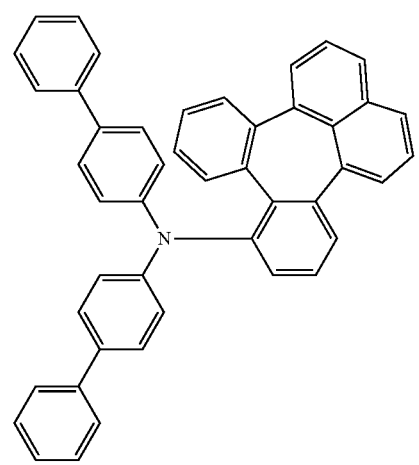
A-20
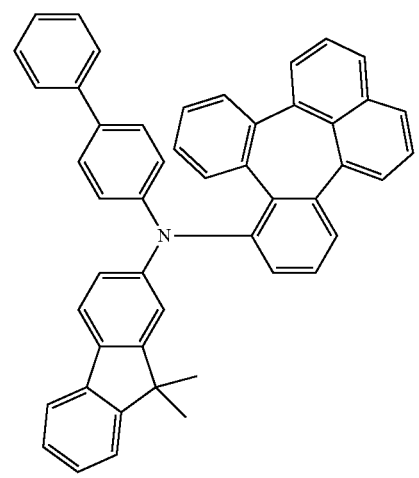

A-21
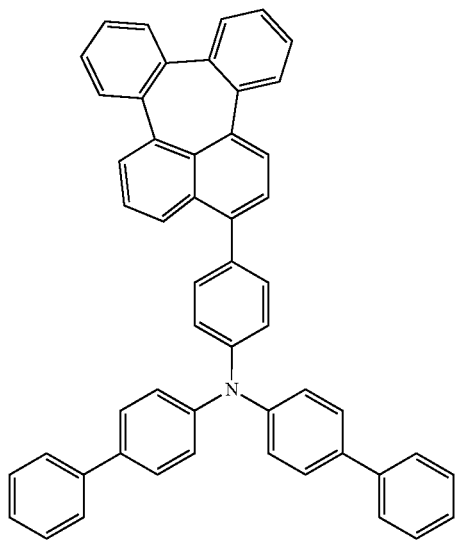
A-22
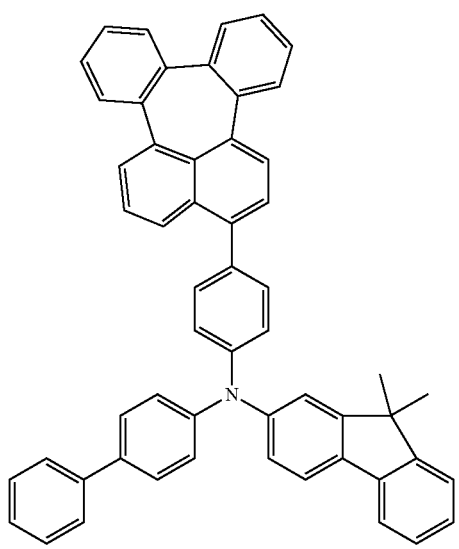
A-23
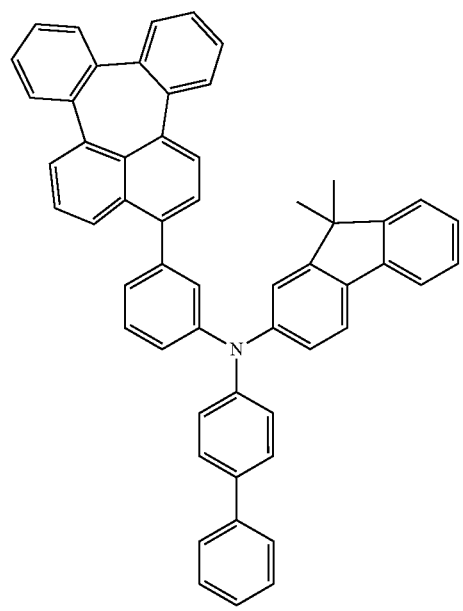
A-24
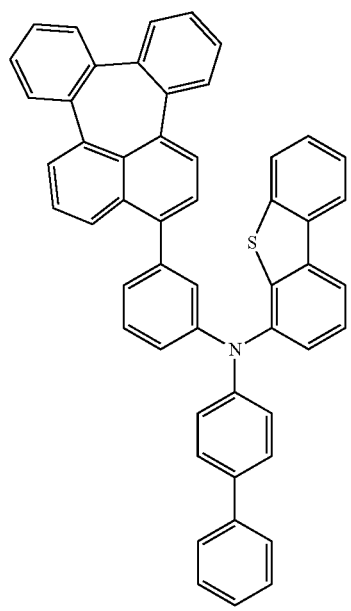
A-25
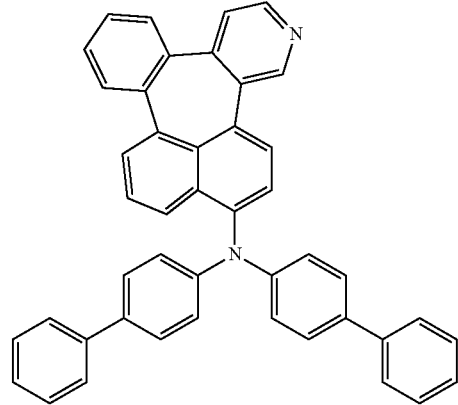

A-26 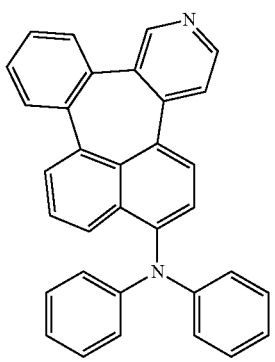
A-29 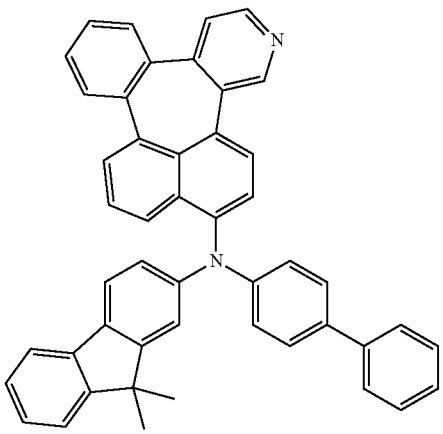
A-27 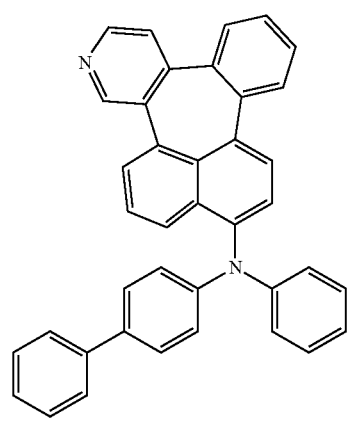
A-30 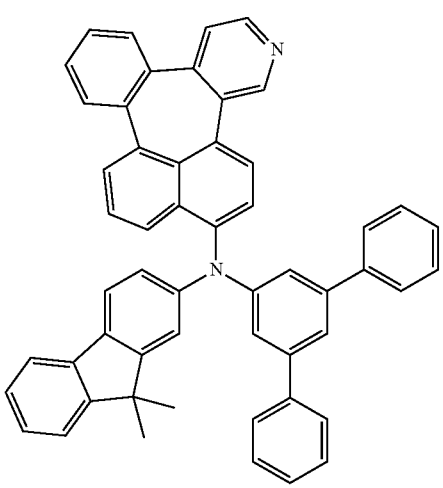
A-28 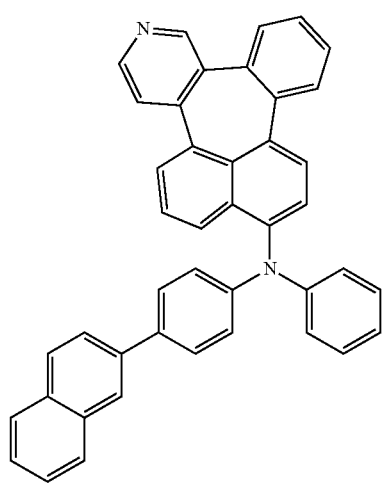
A-31 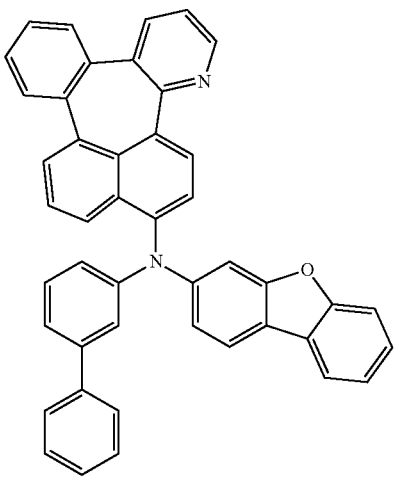

A-32
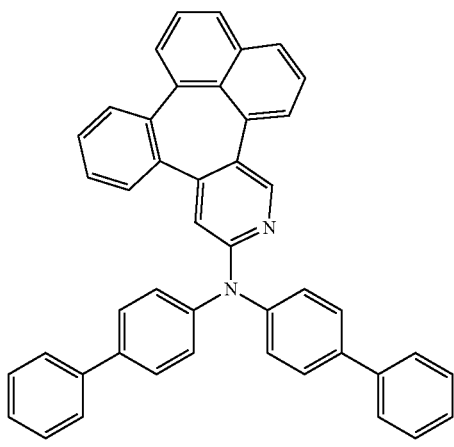
A-33
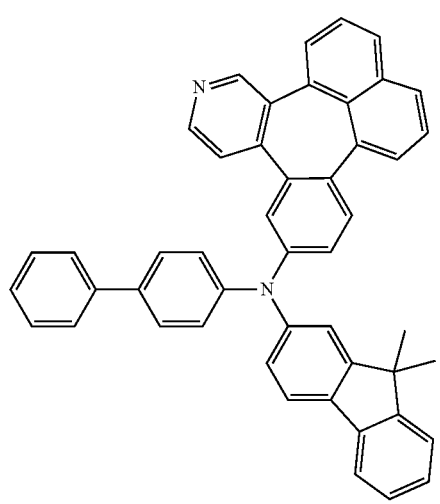
A-34
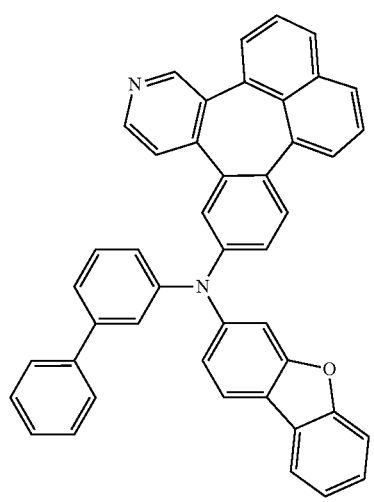
A-35
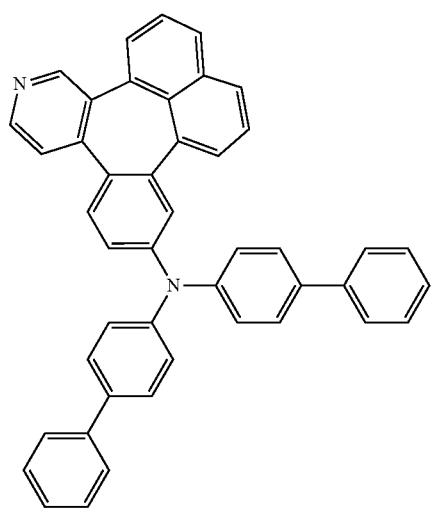
A-36
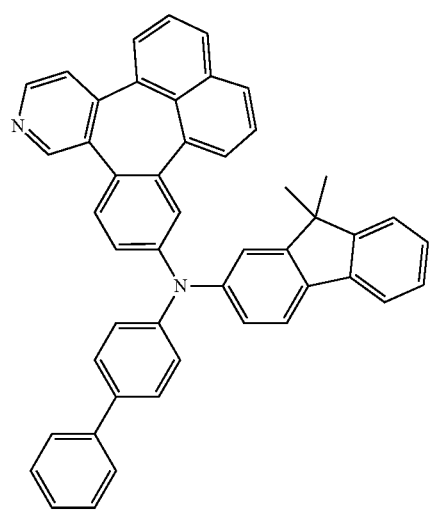
A-37
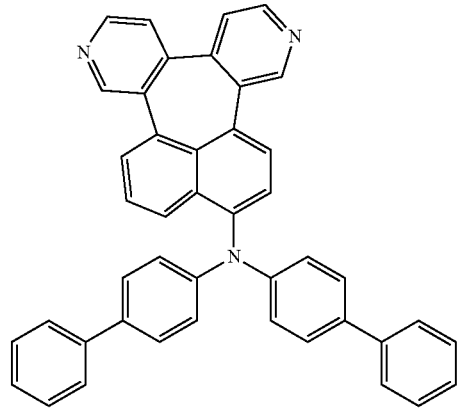

A-38
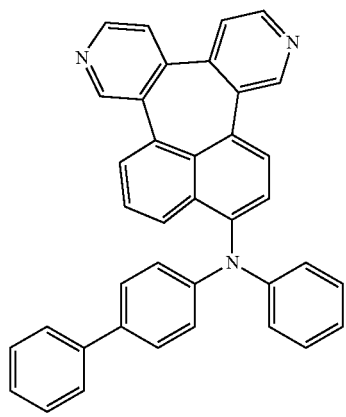
A-41
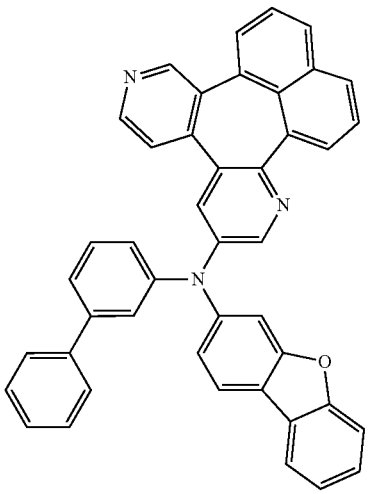
A-39
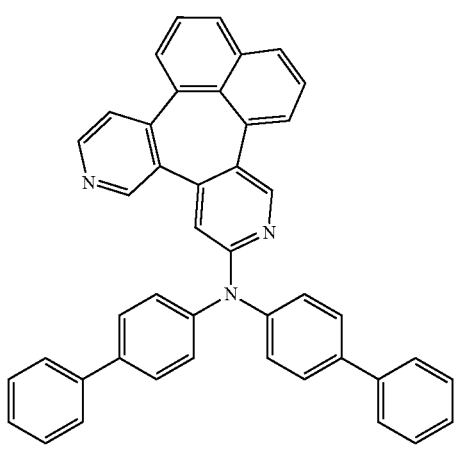
A-42
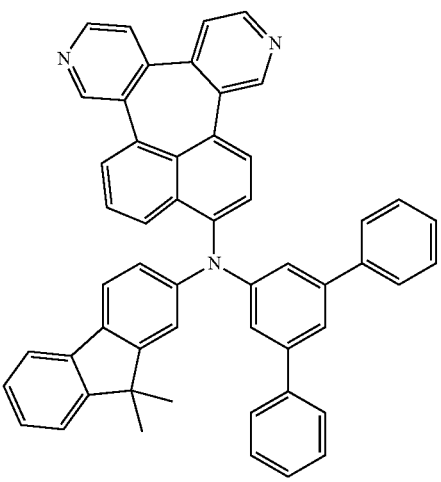
A-40
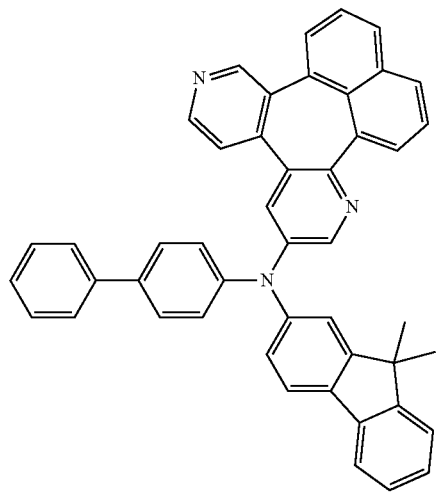
A-43
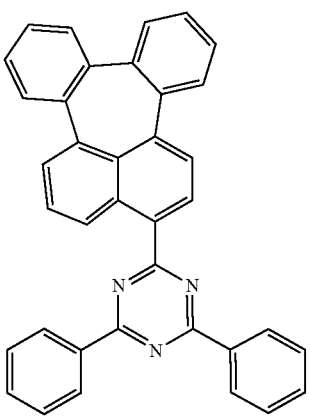

A-44
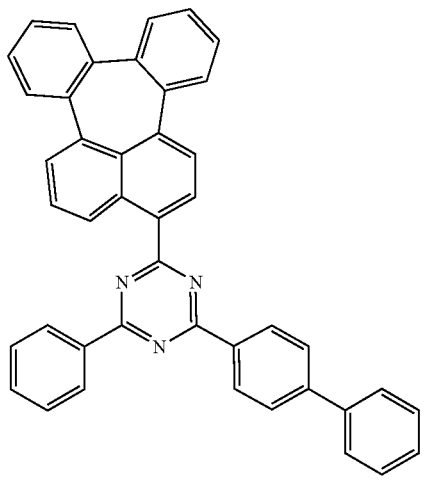
A-45
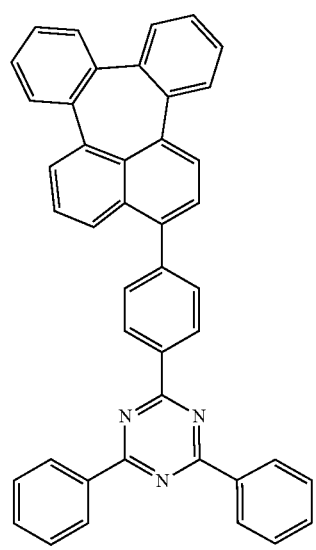
A-46
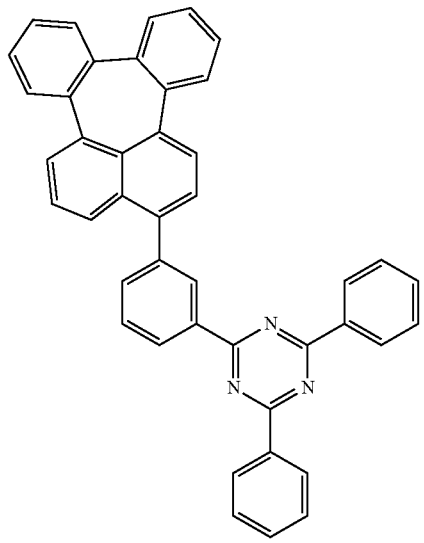
A-47
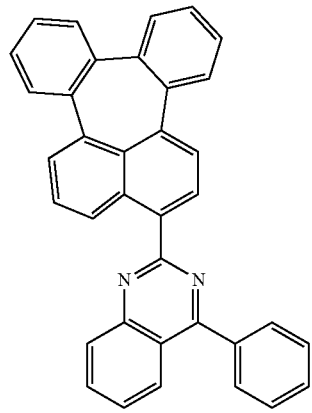
A-48
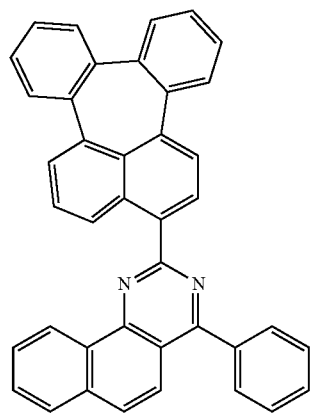
A-49
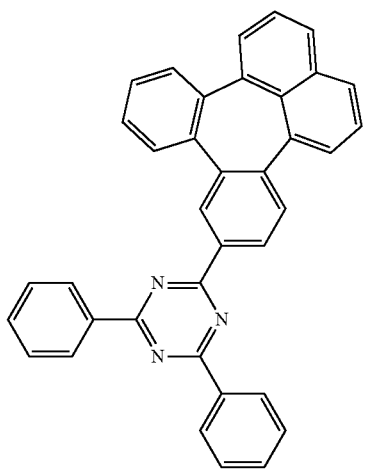

-continued
A-50
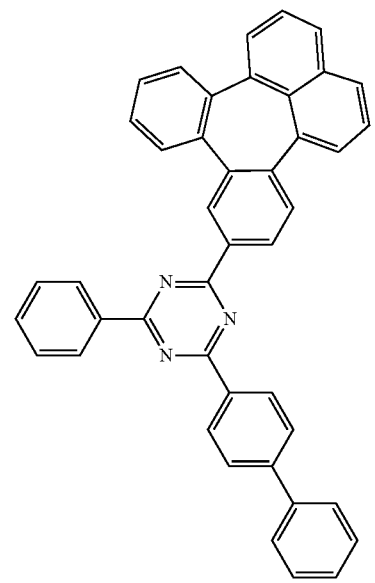
A-51
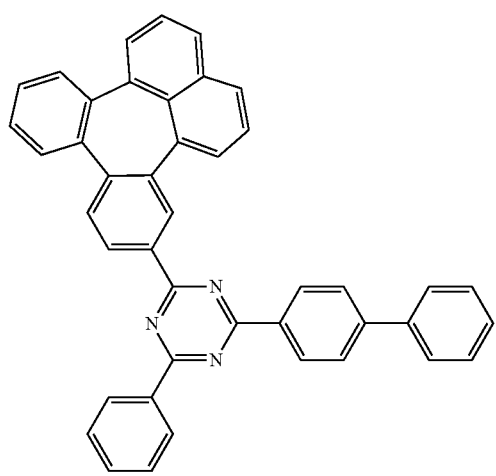
A-52
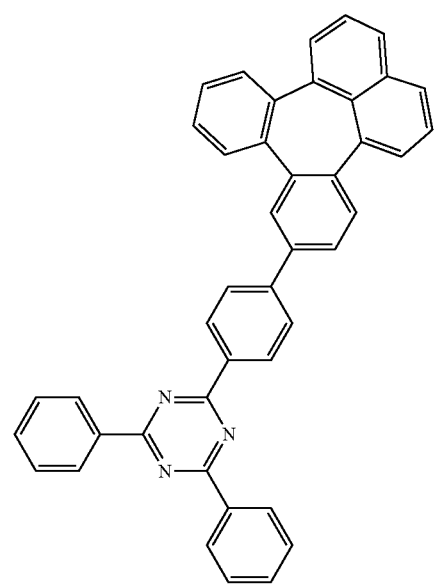
-continued
A-53
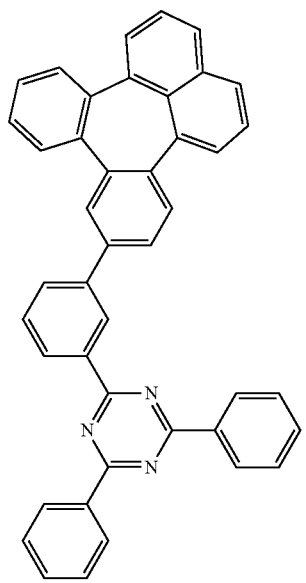
A-54
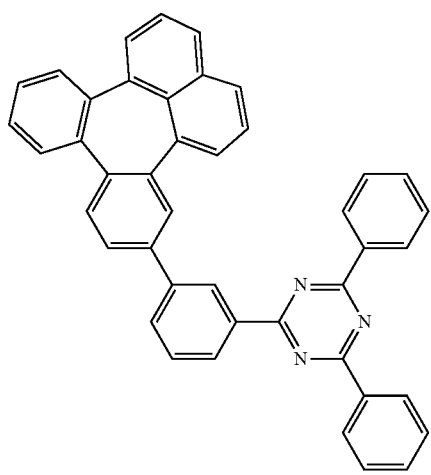
A-55
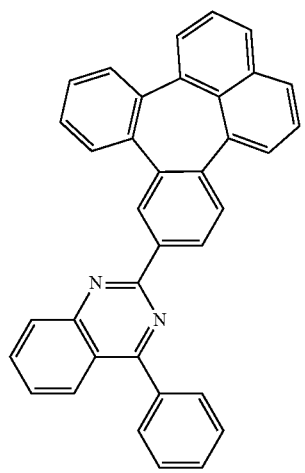

-continued
A-56
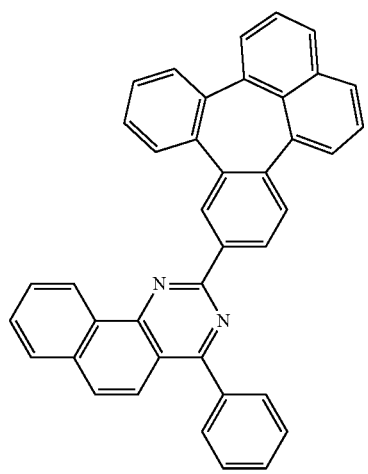
A-57
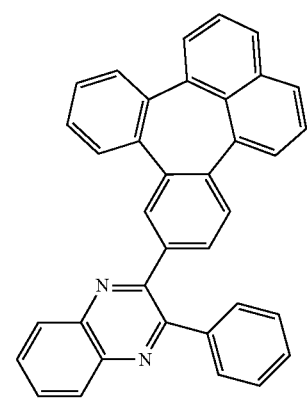
A-58
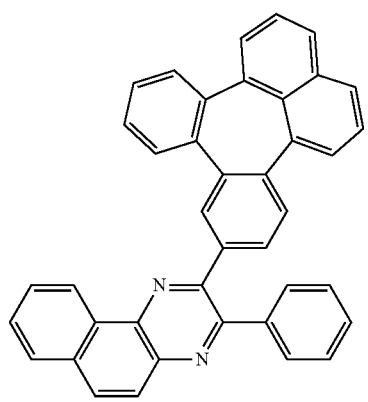
-continued
A-59
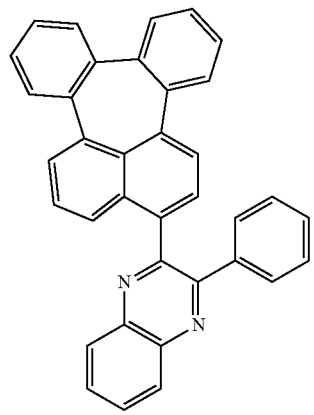
A-60
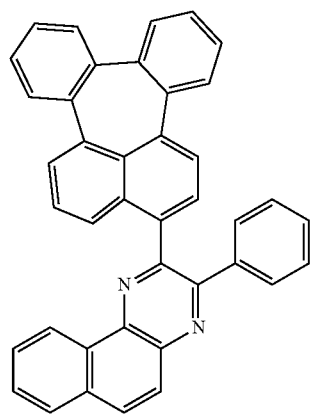
A-61
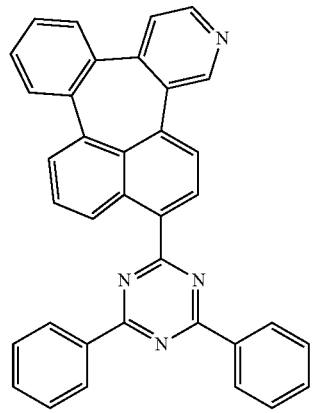

-continued
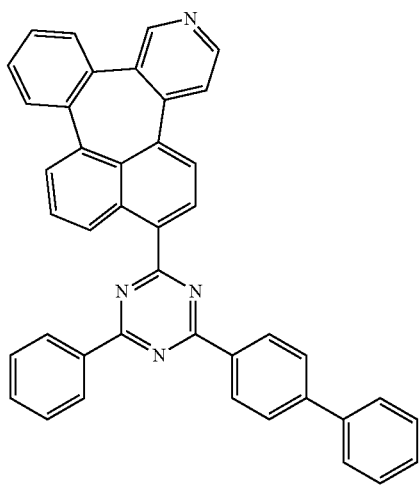
A-62
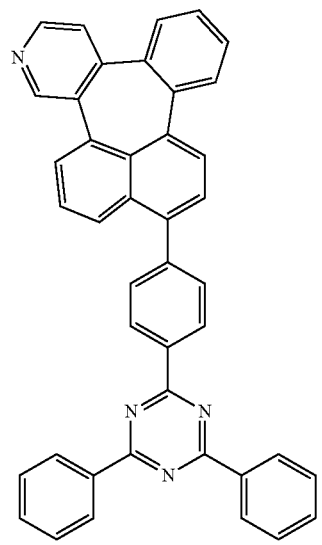
A-63
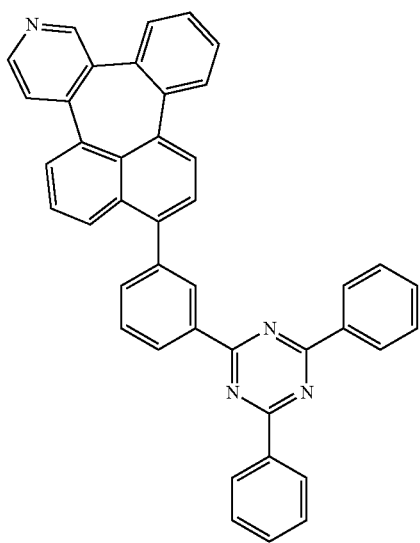
A-64
-continued
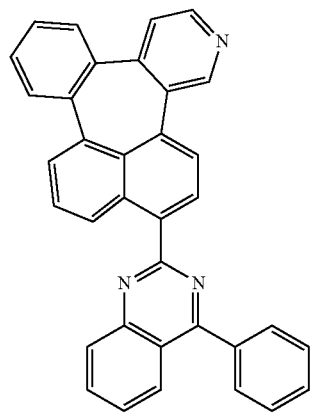
A-65
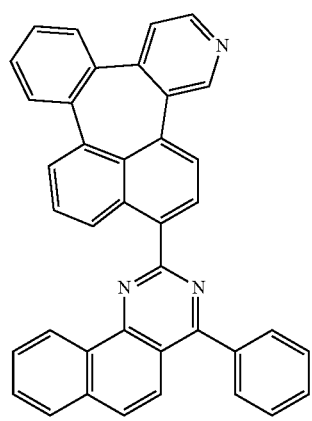
A-66
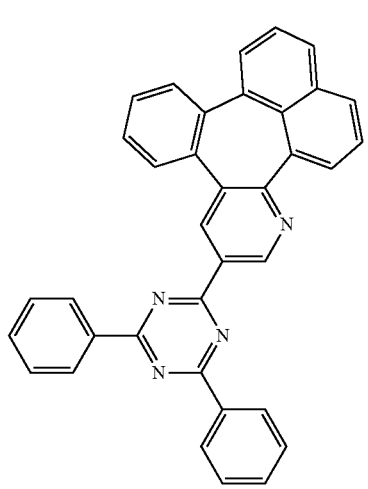
A-67

A-68
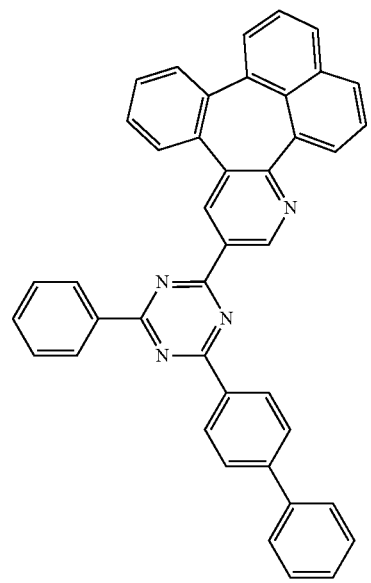
A-69
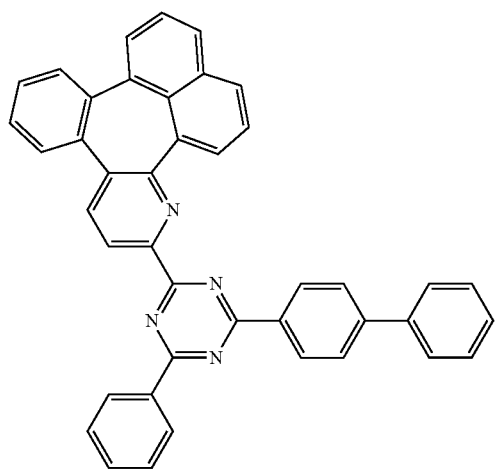
A-70
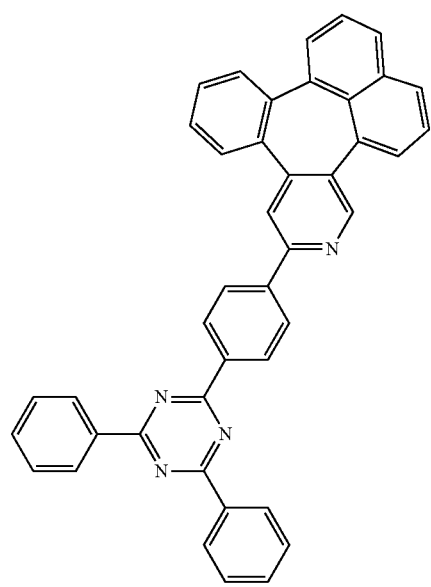
A-71
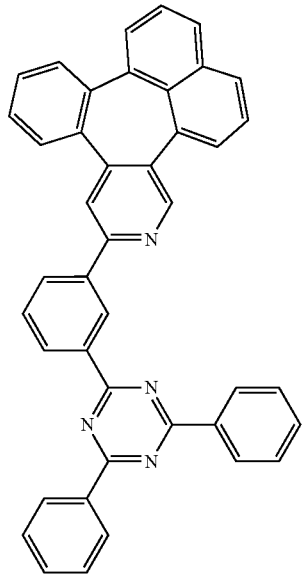
A-72
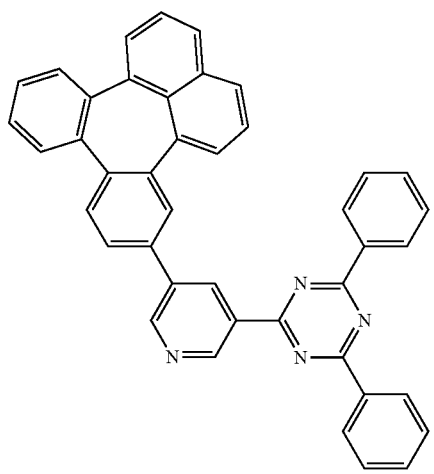
A-73
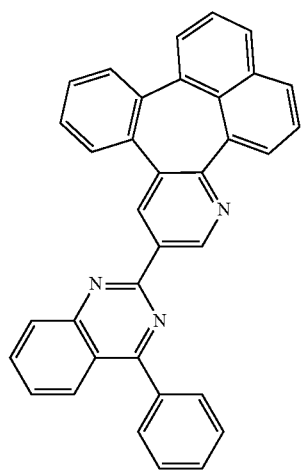

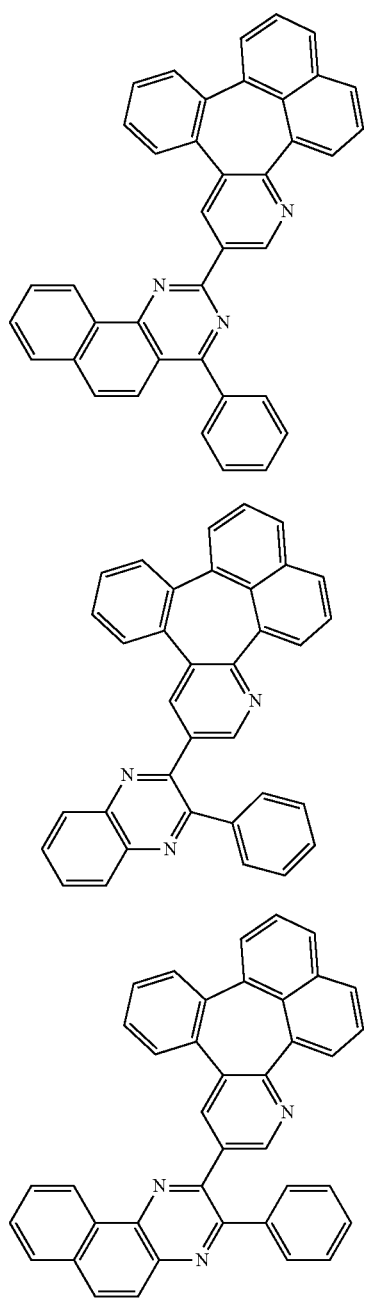

A-74

A-75

A-76

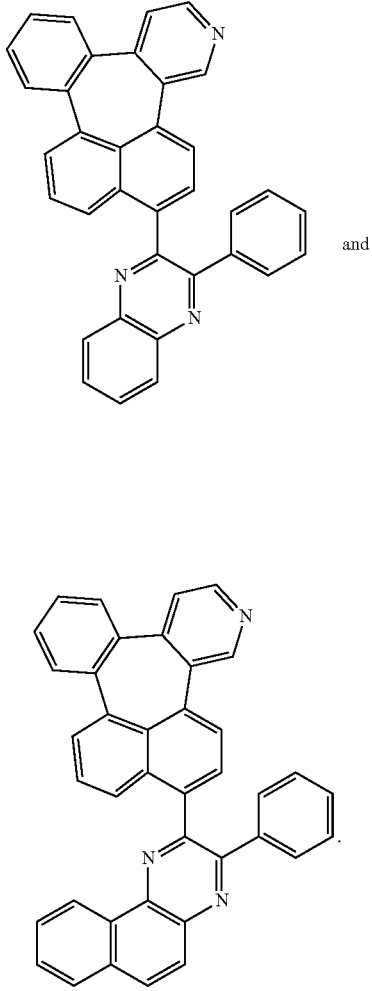

A-77 and

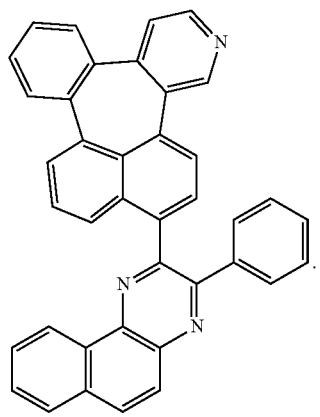

A-78

6. An organic electroluminescent material comprising the organic electroluminescent compound according to claim 1.

7. An organic electroluminescent device comprising the organic electroluminescent compound according to claim 1.

8. The organic electroluminescent device according to claim 7, wherein the organic electroluminescent compound is comprised in a hole transport zone.

9. A display device comprising the organic electroluminescent compound according to claim 1.

* * * * *

UNITED STATES PATENT AND TRADEMARK OFFICE
CERTIFICATE OF CORRECTION

PATENT NO. : 11,605,781 B2
APPLICATION NO. : 16/757778
DATED : March 14, 2023
INVENTOR(S) : Hong-Se Oh et al.

Page 1 of 5

It is certified that error appears in the above-identified patent and that said Letters Patent is hereby corrected as shown below:

In the Drawings

Fig. 1, a formula of the organic electroluminescent compound, has an inadvertent error:

" 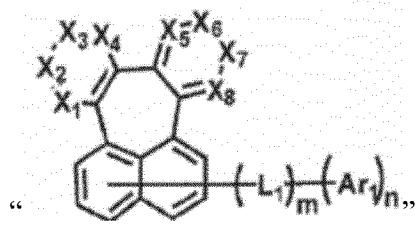 " should be " 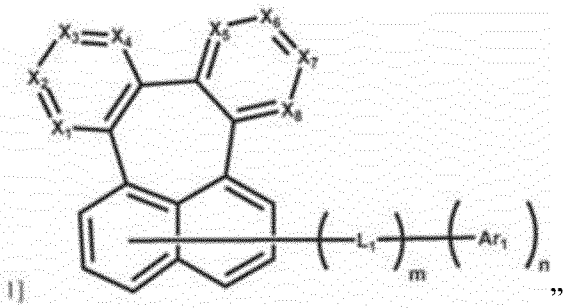 "

In the Specification

The formula 1-1, 1-2 and 1-3 have an inadvertent error. The formulas appearing from Column 7, Line 45 to Column 8, Line 13:

" 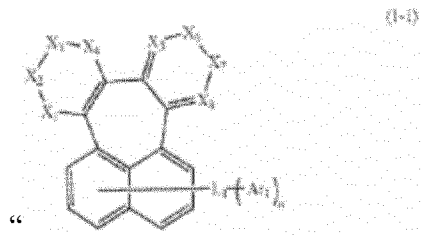 " should be " 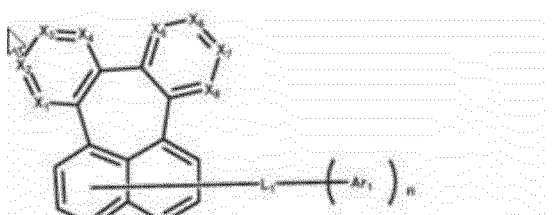 "

Signed and Sealed this
Eleventh Day of February, 2025

Coke Morgan Stewart
*Acting Director of the United States Patent and Trademark Office*

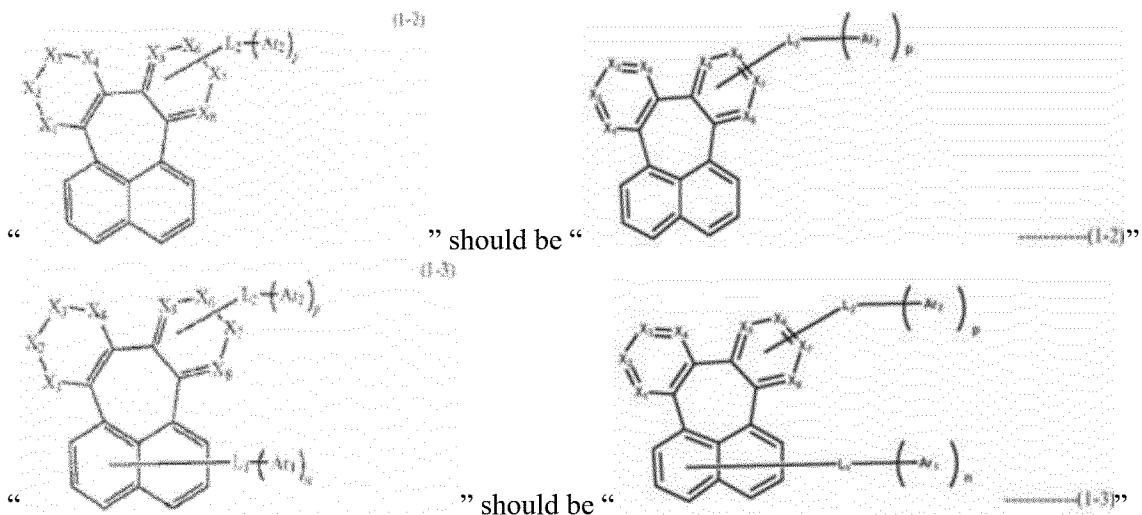
The formula 2-1 and 2-2 have an inadvertent error. The formulas appearing from Column 8, Line 20 to Column 8, Line 48:
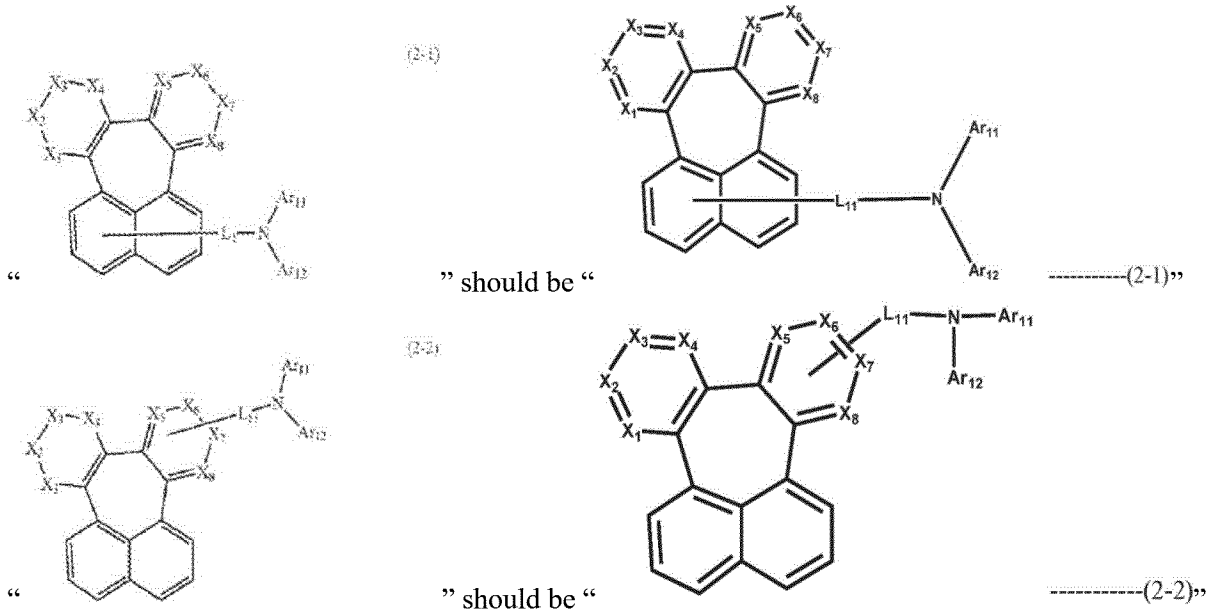
The formula 3-1 and 3-2 also have an inadvertent error. The formulas appearing from Column 8, Line 56 to Column 9, Line 12:
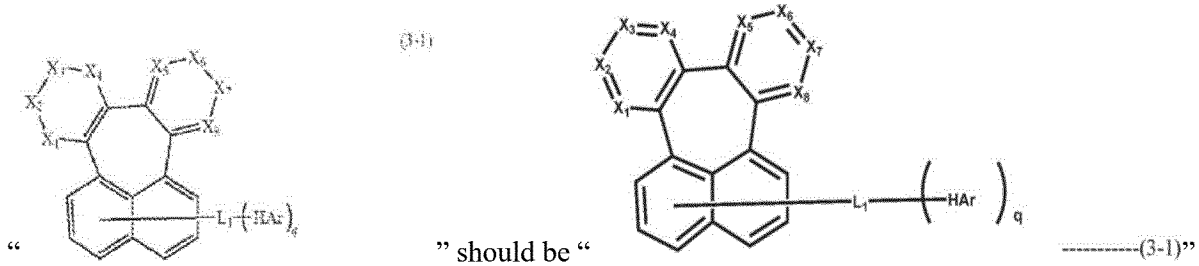

CERTIFICATE OF CORRECTION (continued)
U.S. Pat. No. 11,605,781 B2

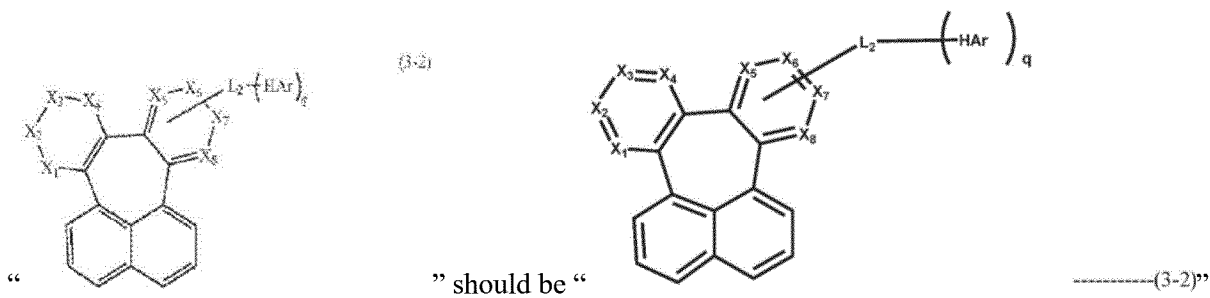

In the Claims

In Claim 1, the formula 1-1, 1-2 and 1-3 have been inadvertently omitted. The omitted formulas should appear around Line 4 in Column 157, between "by the following formula 1-1, 1-2 or 1-3" and "wherein"; so that the formulas requiring insertion are:

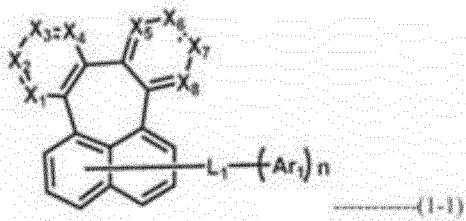

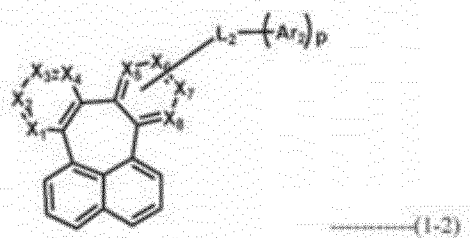

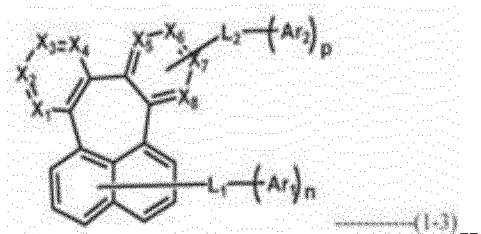

CERTIFICATE OF CORRECTION (continued)
U.S. Pat. No. 11,605,781 B2

In Claim 3, the formula 2-1 and 2-2 have been inadvertently omitted. The omitted formulas should appear around Line 3 in Column 158, between "by the following formula 2-1 or 2-2:" and "wherein"; so that the formulas requiring insertion are:

--
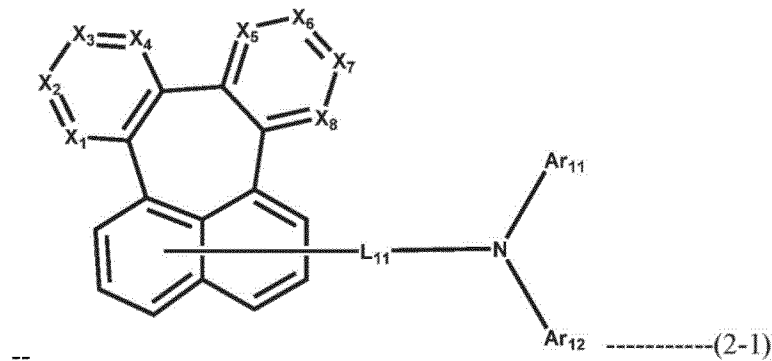
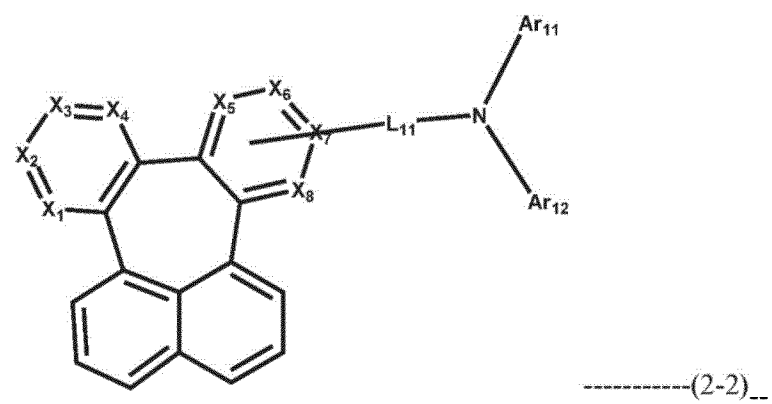
--

CERTIFICATE OF CORRECTION (continued)
U.S. Pat. No. 11,605,781 B2

In Claim 4, the formula 3-1 and 3-2 have been inadvertently omitted. The omitted formulas should appear around Line 19 in Column 158, between "by the following formula 3-2" and "wherein"; so that the formulas requiring insertion are:

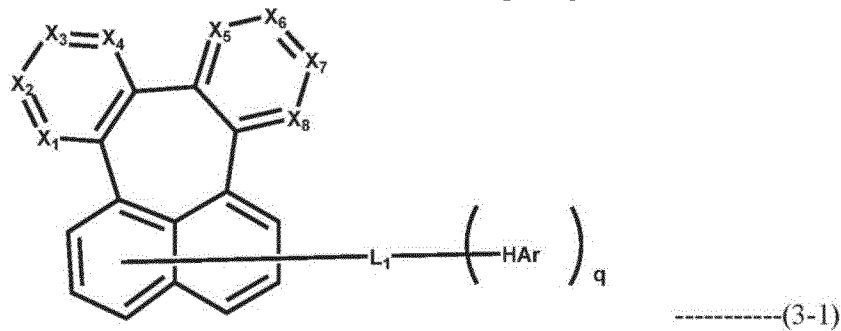

-----------(3-1)

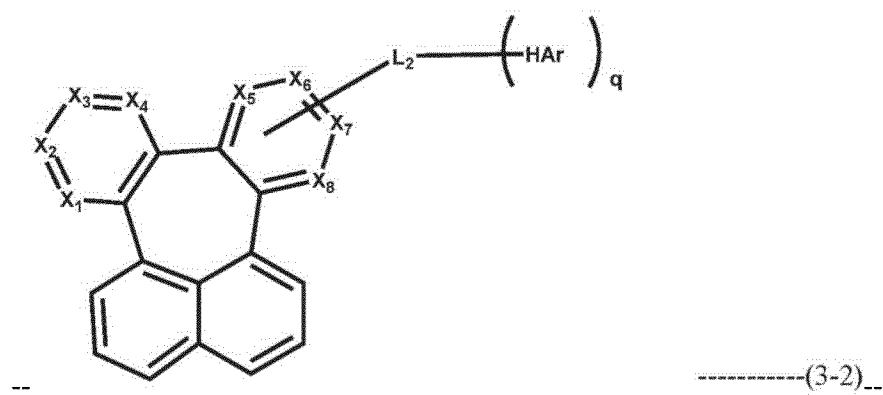

-----------(3-2)--